(12) United States Patent
Kahn et al.

(10) Patent No.: US 8,758,584 B2
(45) Date of Patent: Jun. 24, 2014

(54) ELECTROCHEMICAL SENSORS

(75) Inventors: Carolyn R. Kahn, San Francisco, CA (US); Elicia Wong, Foster City, CA (US); James A. Wilkins, San Francisco, CA (US); Vern Norviel, San Francisco, CA (US)

(73) Assignee: Sensor Innovations, Inc., Burlingame, CA (US)

( * ) Notice: Subject to any disclaimer, the term of this patent is extended or adjusted under 35 U.S.C. 154(b) by 0 days.

(21) Appl. No.: 13/329,135

(22) Filed: Dec. 16, 2011

(65) Prior Publication Data

US 2012/0187000 A1    Jul. 26, 2012

Related U.S. Application Data

(60) Provisional application No. 61/424,040, filed on Dec. 16, 2010, provisional application No. 61/550,355, filed on Oct. 21, 2011.

(51) Int. Cl.
| | |
|---|---|
| *G01N 27/333* | (2006.01) |
| *G01N 27/26* | (2006.01) |
| *G01N 27/30* | (2006.01) |
| *G01N 27/416* | (2006.01) |

(52) U.S. Cl.
CPC .......... *G01N 27/302* (2013.01); *G01N 27/4167* (2013.01); *G01N 27/3335* (2013.01)
USPC ........... 204/416; 204/433; 204/400; 324/438; 422/82.03; 422/68.1; 548/406; 428/149

(58) Field of Classification Search
USPC ........... 204/400–435; 205/775–792; 548/406; 422/68.1, 83.02, 82.03; 428/149, 1.23, 428/405; 324/438; 257/4
See application file for complete search history.

(56) References Cited

U.S. PATENT DOCUMENTS

| | | | |
|---|---|---|---|
| 3,682,160 | A | 8/1972 | Murata |
| 3,926,764 | A | 12/1975 | Ruzicka et al. |
| 3,982,960 | A | 9/1976 | Hoekje et al. |

(Continued)

FOREIGN PATENT DOCUMENTS

| | | |
|---|---|---|
| DE | 10062044 A1 | 6/2002 |
| DE | 10108539 A1 | 9/2002 |

(Continued)

OTHER PUBLICATIONS

Ward et al. (Biosensors & Bioelectronics 17, 2002, 181-189).*

(Continued)

*Primary Examiner* — Jennifer Dieterle
(74) *Attorney, Agent, or Firm* — Wilson Sonsini Goodrich & Rosati

(57) ABSTRACT

Systems and methods are provided for detecting the presence of an analyte in a sample. A solid state electrochemical sensor can include a redox active moiety having an oxidation and/or reduction potential that is sensitive to the presence of an analyte immobilized over a surface of a working electrode. A redox active moiety having an oxidation and/or reduction potential that is insensitive to the presence of the analyte can be used for reference. Voltammetric measurements made using such systems can accurately determine the presence and/or concentration of the analyte in the sample. The solid state electrochemical sensor can be robust and not require calibration or re-calibration.

23 Claims, 36 Drawing Sheets

(56) References Cited

U.S. PATENT DOCUMENTS

| | | | |
|---|---|---|---|
| 4,592,807 A | 6/1986 | Switzer | |
| 4,628,013 A | 12/1986 | Figard et al. | |
| 4,704,193 A | 11/1987 | Bowers et al. | |
| 4,752,398 A | 6/1988 | Holbein et al. | |
| 4,758,325 A | 7/1988 | Kanno et al. | |
| 4,900,424 A | 2/1990 | Birth et al. | |
| 4,914,046 A | 4/1990 | Tobin et al. | |
| 5,017,540 A | 5/1991 | Sandoval et al. | |
| 5,120,421 A | 6/1992 | Glass et al. | |
| 5,133,856 A * | 7/1992 | Yamaguchi et al. | 204/416 |
| 5,139,626 A | 8/1992 | Yamaguchi et al. | |
| 5,223,117 A | 6/1993 | Wrighton et al. | |
| 5,296,125 A | 3/1994 | Glass et al. | |
| 5,326,738 A | 7/1994 | Sandoval et al. | |
| 5,331,966 A | 7/1994 | Bennett et al. | |
| 5,364,797 A | 11/1994 | Olson et al. | |
| 5,403,462 A | 4/1995 | Lev et al. | |
| 5,503,728 A | 4/1996 | Kaneko et al. | |
| 5,525,511 A * | 6/1996 | D'Costa | 204/403.09 |
| 5,534,132 A | 7/1996 | Vreeke et al. | |
| 5,540,828 A * | 7/1996 | Yacynych | 205/198 |
| 5,557,596 A | 9/1996 | Gibson et al. | |
| 5,567,302 A | 10/1996 | Song et al. | |
| 5,676,820 A | 10/1997 | Wang et al. | |
| 5,770,453 A | 6/1998 | Beer et al. | |
| 5,786,604 A | 7/1998 | Yamashita et al. | |
| 5,866,434 A | 2/1999 | Massey et al. | |
| 6,042,788 A | 3/2000 | De Wit et al. | |
| 6,096,497 A | 8/2000 | Bauer | |
| 6,175,752 B1 | 1/2001 | Say et al. | |
| 6,221,586 B1 | 4/2001 | Barton et al. | |
| 6,224,745 B1 | 5/2001 | Baltruschat | |
| 6,262,941 B1 | 7/2001 | Naville | |
| 6,322,963 B1 | 11/2001 | Bauer | |
| 6,340,588 B1 | 1/2002 | Nova et al. | |
| 6,342,347 B1 | 1/2002 | Bauer | |
| 6,359,444 B1 | 3/2002 | Grimes | |
| 6,376,977 B1 | 4/2002 | Kawai et al. | |
| 6,391,471 B1 | 5/2002 | Hiraoka et al. | |
| 6,416,651 B1 | 7/2002 | Millar | |
| 6,444,326 B1 | 9/2002 | Smith | |
| 6,461,820 B1 | 10/2002 | Barton et al. | |
| 6,498,492 B1 | 12/2002 | Rezvani | |
| 6,503,701 B1 | 1/2003 | Bauer | |
| 6,562,210 B1 | 5/2003 | Bhullar et al. | |
| 6,620,315 B2 | 9/2003 | Martin | |
| 6,649,350 B2 | 11/2003 | Barton et al. | |
| 6,690,182 B2 | 2/2004 | Kelly et al. | |
| 6,738,670 B1 | 5/2004 | Almendinger et al. | |
| 6,770,190 B1 | 8/2004 | Milanovski et al. | |
| 6,929,636 B1 | 8/2005 | von Alten | |
| 7,038,470 B1 | 5/2006 | Johnson | |
| 7,045,054 B1 | 5/2006 | Buck et al. | |
| 7,109,271 B2 | 9/2006 | Liu et al. | |
| 7,160,678 B1 | 1/2007 | Kayyem et al. | |
| 7,202,037 B2 | 4/2007 | Barton et al. | |
| 7,399,400 B2 | 7/2008 | Soundarrajan | |
| 7,429,630 B2 | 9/2008 | Liu et al. | |
| 7,592,151 B2 | 9/2009 | Liu et al. | |
| 7,635,423 B2 | 12/2009 | Boussaad et al. | |
| 7,731,835 B2 | 6/2010 | Buck et al. | |
| 7,775,083 B2 | 8/2010 | Potyrailo et al. | |
| 7,833,805 B2 | 11/2010 | Cuppoletti | |
| 7,901,555 B2 | 3/2011 | Jiang et al. | |
| 7,947,405 B2 | 5/2011 | Mittelsteadt et al. | |
| 8,177,958 B2 | 5/2012 | Lawrence et al. | |
| 8,506,779 B2 | 8/2013 | Kahn et al. | |
| 2001/0016682 A1 | 8/2001 | Berner et al. | |
| 2002/0015963 A1 | 2/2002 | Keen | |
| 2002/0019707 A1 | 2/2002 | Cohen et al. | |
| 2002/0052076 A1 | 5/2002 | Khan et al. | |
| 2002/0090632 A1 | 7/2002 | Buck et al. | |
| 2002/0090738 A1 | 7/2002 | Cozzette et al. | |
| 2002/0116042 A1 | 8/2002 | Boling | |
| 2003/0081463 A1 | 5/2003 | Bocian et al. | |
| 2003/0148169 A1 | 8/2003 | Willner et al. | |
| 2003/0153900 A1 | 8/2003 | Aceti et al. | |
| 2003/0206026 A1 | 11/2003 | Diakonov et al. | |
| 2004/0134798 A1 | 7/2004 | Toumazou et al. | |
| 2004/0138840 A1 | 7/2004 | Wolfe | |
| 2005/0029125 A1 | 2/2005 | Jiang et al. | |
| 2005/0097941 A1 | 5/2005 | Sandvik et al. | |
| 2005/0110053 A1 | 5/2005 | Shur et al. | |
| 2005/0186333 A1 | 8/2005 | Douglas | |
| 2005/0270822 A1 | 12/2005 | Shrivastava et al. | |
| 2006/0151324 A1 | 7/2006 | Davies et al. | |
| 2007/0034530 A1 | 2/2007 | Lin et al. | |
| 2007/0272552 A1 | 11/2007 | Jiang et al. | |
| 2008/0023328 A1 | 1/2008 | Jiang et al. | |
| 2008/0035481 A1 | 2/2008 | McCormack et al. | |
| 2008/0179197 A1 * | 7/2008 | Wu | 205/775 |
| 2008/0190855 A1 | 8/2008 | Compton et al. | |
| 2008/0302660 A1 * | 12/2008 | Kahn et al. | 204/416 |
| 2009/0014329 A1 | 1/2009 | Silveri | |
| 2009/0120873 A1 * | 5/2009 | Becker et al. | 210/636 |
| 2009/0178921 A1 | 7/2009 | Lawrence et al. | |
| 2009/0218239 A1 | 9/2009 | Gooding et al. | |
| 2010/0133547 A1 | 6/2010 | Kunze et al. | |
| 2010/0179399 A1 | 7/2010 | Goode, Jr. et al. | |
| 2011/0048969 A1 * | 3/2011 | Lawrence et al. | 205/775 |

FOREIGN PATENT DOCUMENTS

| | | |
|---|---|---|
| EP | 0228969 A2 | 7/1987 |
| EP | 0228969 A3 | 3/1989 |
| EP | 0411127 A1 | 2/1991 |
| EP | 1621636 B1 | 1/2010 |
| GB | 2347746 A | 9/2000 |
| GB | 2430749 A | 4/2007 |
| GB | 2450002 B | 4/2009 |
| GB | 2451596 B | 9/2009 |
| JP | 64-41852 | 2/1989 |
| JP | 2005-257684 A | 9/2005 |
| WO | WO 98/57159 A1 | 12/1998 |
| WO | WO 00/11474 A1 | 3/2000 |
| WO | WO 02/48701 A2 | 6/2002 |
| WO | WO 02/060812 A2 | 8/2002 |
| WO | WO 02/060812 A3 | 11/2002 |
| WO | WO 02/048701 A3 | 4/2003 |
| WO | WO 03/058692 A1 | 7/2003 |
| WO | WO 2005/066618 A1 | 7/2005 |
| WO | WO 2005/074161 A1 | 8/2005 |
| WO | WO 2005/085825 * | 9/2005 |
| WO | WO 2005/085825 A1 | 9/2005 |
| WO | WO 2006/007533 A1 | 1/2006 |
| WO | WO 2006/120396 A2 | 11/2006 |
| WO | WO 2006/120396 A3 | 2/2007 |
| WO | WO 2007/017252 A1 | 2/2007 |
| WO | WO 2007/034131 A1 | 3/2007 |
| WO | WO 2007/106936 A1 | 9/2007 |
| WO | WO 2007/139574 A1 | 12/2007 |
| WO | WO 2008/154409 A1 | 12/2008 |
| WO | WO 2009/009448 A1 | 1/2009 |
| WO | WO 2009/115840 A1 | 9/2009 |
| WO | WO 2010/104962 A1 | 9/2010 |
| WO | WO 2010/111531 A2 | 9/2010 |
| WO | WO 2010/118156 A1 | 10/2010 |
| WO | WO 2010/111531 A3 | 1/2011 |

OTHER PUBLICATIONS

Ghica et al. (Analytical Letters, 38: 907-920, 2005).*
Sigma Aldrich Spec Sheet, downloaded May 16, 2013.*
Ciobanu et al. (Rev.Adv.Mater.Sci 22, Sep. 25, 2009, 89-96).*
Bruns, D. Are Meters Accurate Enough? Diabetes Forecast, Apr. 2008. Available at http://forecast.diabetes.org/print/436. Accessed Jan. 30, 2013.
International search report and written report dated Nov. 23, 2012 for PCT Application No. US2011/065652.
Office action dated Feb. 4, 2013 for U.S. Appl. No. 13/241,171.
Office action dated Apr. 13, 2011 for U.S. Appl. No. 12/049,230.
Office action dated May 8, 2012 for U.S. Appl. No. 13/241,171.
Office action dated Sep. 13, 2011 for U.S. Appl. No. 12/049,230.

(56) References Cited

OTHER PUBLICATIONS

Shinwari, et al. Microfabricated reference electrodes and their biosensing applications. Sensors. 2010; 10:1679-1715.
Dicks, et al. The application of ferrocene-modified n-type silicon in glucose biosensors. Electroanalysis. Jan. 1993; 5(1): 1-9.
U.S. Appl. No. 13/787,300, filed Mar. 6, 2013, Kahn et al.
U.S. Appl. No. 13/787,534, filed Mar. 6, 2013, Kahn et al.
U.S. Appl. No. 13/923,214, filed Jun. 20, 2013, Kahn et al.
Lim, et al. Synthesis, charaterization and catalytic performance of porous nafion resin/silica nanocomposites for esterification of lauric acid and methanol. Journal of Physical Science. 2009; 20(2):23-36.
Liu, et al. Nafion/PTFE composite membranes for fuel cell applications. Journal of Membrane Science. 2003; 212:213-223.
U.S. Appl. No. 13/241,171, filed Sep. 22, 2011, Kahn et al.
Bateman, et al. Alkylation of Porous Silicon by Direct Reaction with Alkenes and Alkynes. Angew. Chem. Int. Ed. 1998; 37(19): 2683-2685.
Bergveld. ISFET, Theory and Practice. IEEE Sensor Conference, Toronto, Oct. 2003, 1-26.
Buriak. Organometallic Chemistry on Silicon and Germanium Surfaces. Chem. Review. 2002; 102(5):1271-1308.
Buriak. Organometallic Chemistry on Silicon Surfaces: formation of functional monolayers bound through Si-C bonds. Chem. Commun. 1999; 1051-1060.
Carroll, et al. Low-Temperature Preparation of Oxygen- and Carbon-Free Silicon and Silicon-Germanium Surfaces for Silicon and Silicon-Germanium Epitaxial Growth by Rapid Thermal Chemical Vapor Deposition. J. Electrochem Soc. 2000; 147(12):4652-4659.
Casimiri, et al. Co-immobilized L-lactate oxidase and L-lactate dehydrogenase on a film mounted on oxygen electrode for highly sensitive L-lactate determination. Biosensors and Bioelectronics. 1996; 11(8):783-789.
Chou, et al. Study on the temperature effects of Al2O3 gate pH-ISFET . Sensors and Actuators B. Elsevier Sequoia S.A. Lausanne, CH. 2002; 81(2-3):152-157.
Delamar, et al. Modification of carbon fiber surfaces by electrochemical reduction to carbon epoxy composites. Carbon, Elsevier, Oxford, BG. 1997; 35(6):801-807.
Evans, R. A. The Rise of Azide—Alkyne 1,3-Dipolar 'Click' Cycloaddition and its Application to Polymer Science and Surface Modification. Australian Journal of Chemistry. 2007; 60(6) 384-395.
Fischer, et al. Derivatization of surfaces via reaction of strained silicon-carbon bonds. Characterization by photoacoustic spectroscopy. American Chemical Society. 1979; 101(22):6501-6506.
Gee, et al. Infrared spectroscopy of hydrogen-terminated gallium arsenide (100). J. Vacuum Sci. Tech. Jul./Aug. 1992; 10(4):892-896.
Hammond, et al. Synthesis N.M.R. spectra and structure of macrocyclic compounds containing Ferrocene unit. J. Chem. Soc. Perkin. Trans. 1983; I 707-715.
Heald, et al. Chemical Derivatisation of Multiwalled Carbon Nanotubes Using Diazonium Salts. Chemphyschem. Nov. 12, 2004; 5(11):1794-9.
International search report dated Sep. 11, 2008 for PCT Application No. US2008/066165.
Johnson, et al. Poly(L-cysteine) as an electrochemically modifiable ligand for trace metal chelation. Analytical chemistry. 2005; 77(1):30-35.
Kolb, et al. Click Chemistry: Diverse Chemical Function from a Few Good Reactions. Angew Chem Int Ed Engl. Jun. 1, 2001;40(11):2004-2021.
Kwon, et al. An electrochemical immunosensor using ferrocenyl-tethered dendrimer. Analyst. Mar. 2006;131(3):402-6.

Lafitte, et al. Anthraquinone—ferrocene film electrodes: Utility in pH and oxygen sensing. Electrochemistry Communications. 2008; 10(12):1831-1834.
Lawrence, et al. Triple Component Carbon Epoxy pH Probe. Electroanalysis. 2007; 19(4):424-428.
Leventis, et al. Derivatised carbon powder electrodes: reagentless pH sensors. Talanta. 2004; 63(4):1039-1051.
Maoz, et al. On the formation and structure of self-assembling monolayers. I: Comparative ATR-wettability study of Langmuir-Blodgett and adsorbed films on flat substrates and glass microbeads. Journal of colloid and interface science. 1984; 100(2):465-496.
Medina, et al. Ferrocenyldimethyl-[2.2]-cryptand: Solid State Structure of the External Hydrate and Al¬ kali and Alkaline-earth-dependent Electrochemical Behaviour. J. Chem. Soc. Chem. Commun. 1991;290-292.
Pandurangappa, et al. Homogeneous Chemical Derivatisation of Carbon Particles: A Novel Method for Functionalizing Carbon Surfaces. The Analyst. 2002; 127:1568-1571.
Pandurangappa, et al. Physical adsorption of N,N'-diphenyl-p-phenylenediamine onto carbon particles: application to the detection of sulfide. Analyst. May 2003;128(5):473-9.
Robinson, et al. Redox-sensitive copolymer: a single-component pH sensor. Anal Chem. Apr. 1, 2006;78(7):2450-5.
Robinson, et al. Vinylferrocene homopolymer and copolymers: an electrochemical comparison. Anal Sci. Mar. 2008;24(3):339-43.
Schmuki, et al. In situ characterization of anodic silicon oxide films by ac impedance measurements. Electrochem. Soc. 1995; 142(5):1705-1712.
Seymour, et al. Reaction with N,N-Diethyl-p-phenylenediamine: A Procedure for the Sensitive Square-Wave Voltammetric Detection of Chlorine. Electroanalysis. 2003; 15(8):689-694.
Shu, et al. Synthesis and Charge-Transport Properties of Polymers Derived from the Oxidation of 1-Hydro-1- '46-(pyrrol-1-yphexyl)-4,4'-bipyridinium Bis(hexa¬ fluorophosphate) and Demonstration of a pH-Sensitive Microelectrochemical Transistor Derived from the Redox Properties of a Conventional Redox Center. J. Phys. Chem. 1988; 92: 5221-5229.
Spetz et al. Current status of silicon carbide based high-temperature gas sensors. IEEE Transactions on Electron Devices. IEEE Service Center, Pisacataway, NJ, US. Mar. 1999; 46(3): p. 561, XP011016819.
Stewart, et al. Direct Covalent Grafting of Conjugated Molecules onto Si, GaAs, and Pd Surfaces from Aryldiazonium Salts. J. Am. Chem. Soc. 2004; 126:370-378.
Streeter, et al. A sensitive reagentless pH probe with a ca. 120 mV/pH unit response. Journal of Solid State Electrochemistry. 2004; 8(10):718-721.
Sun, et al. Optimized cleaning method for producing device quality InP(100) surfaces . J. Appl. Phys. 2005; 97:124902. doi:10.1063/1.1935745.
UK search report dated Jun. 24, 2008 for GB application No. 0810556.1.
Wildgoose, et al. Abrasively Immobilised Multiwalled Carbon Nanotube Agglomerates: A Novel Electrode Material Approach for the Analytical Sensing of pH. ChemPhysChem. 2004; 5:669-677. vol. 5, Issue 5, pp. 669-677, May 17, 2004.
Wildgoose, et al. Anthraquinone-derivatised carbon powder: reagentless voltammetric pH electrodes. Talanta. 2003; 60:887-893.
Wildgoose, et al. Graphite powder and multiwalled carbon nanotubes chemically modified with 4-nitrobenzylamine. Chemphyschem. Feb. 2005;6(2):352-62.
Yu, et al. Electron-transfer Characteristics of Ferrocene Attached to Single-walled Carbon Nanotubes (SWCNT) Arrays directly anchored to silicon (100). Electrochimica Acta. 2007; 52: 6206-6211.

* cited by examiner

Figure 1
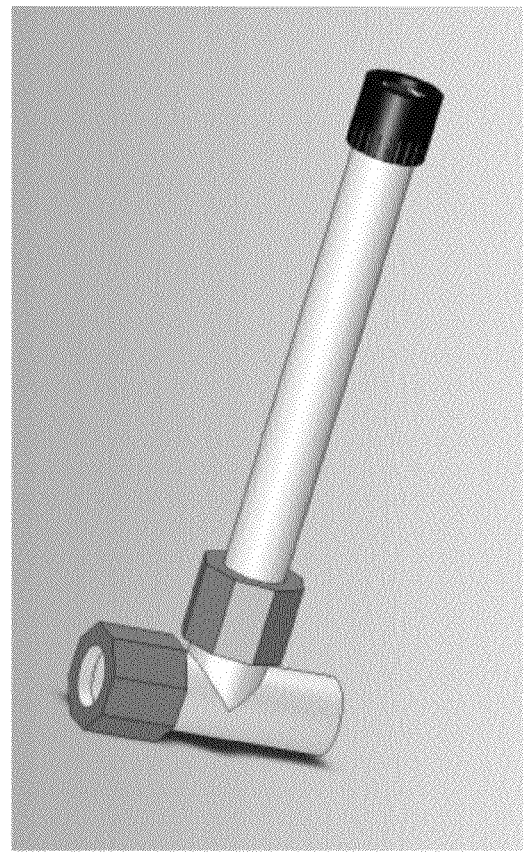
(b)
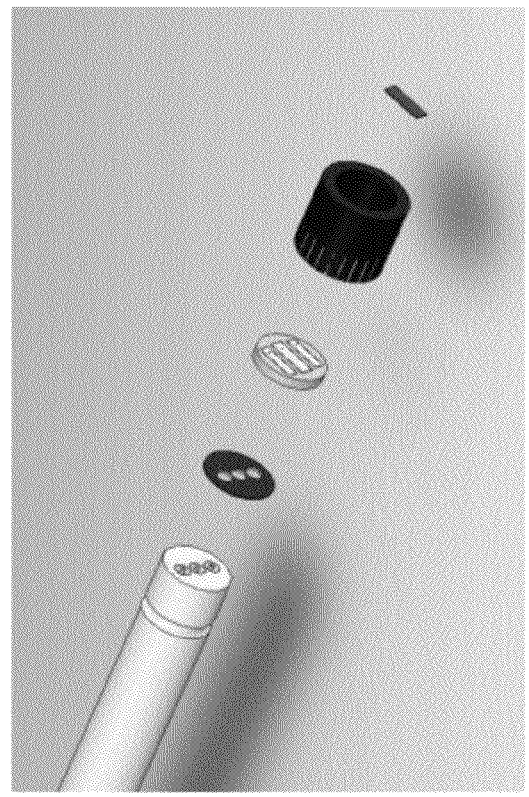
(a)

Figure 8
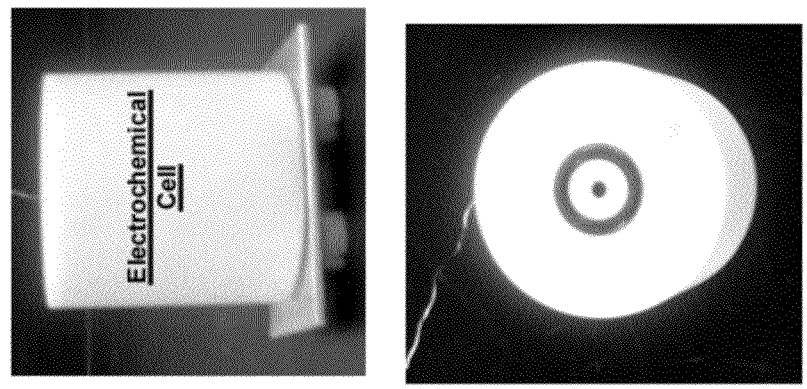
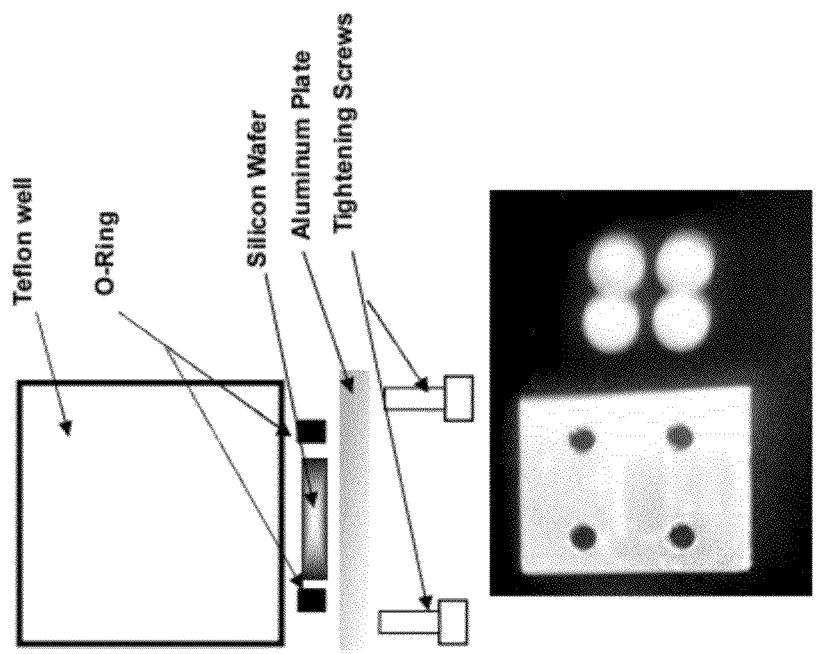

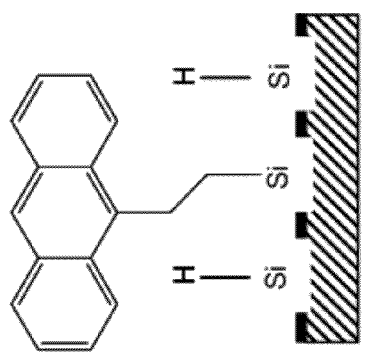
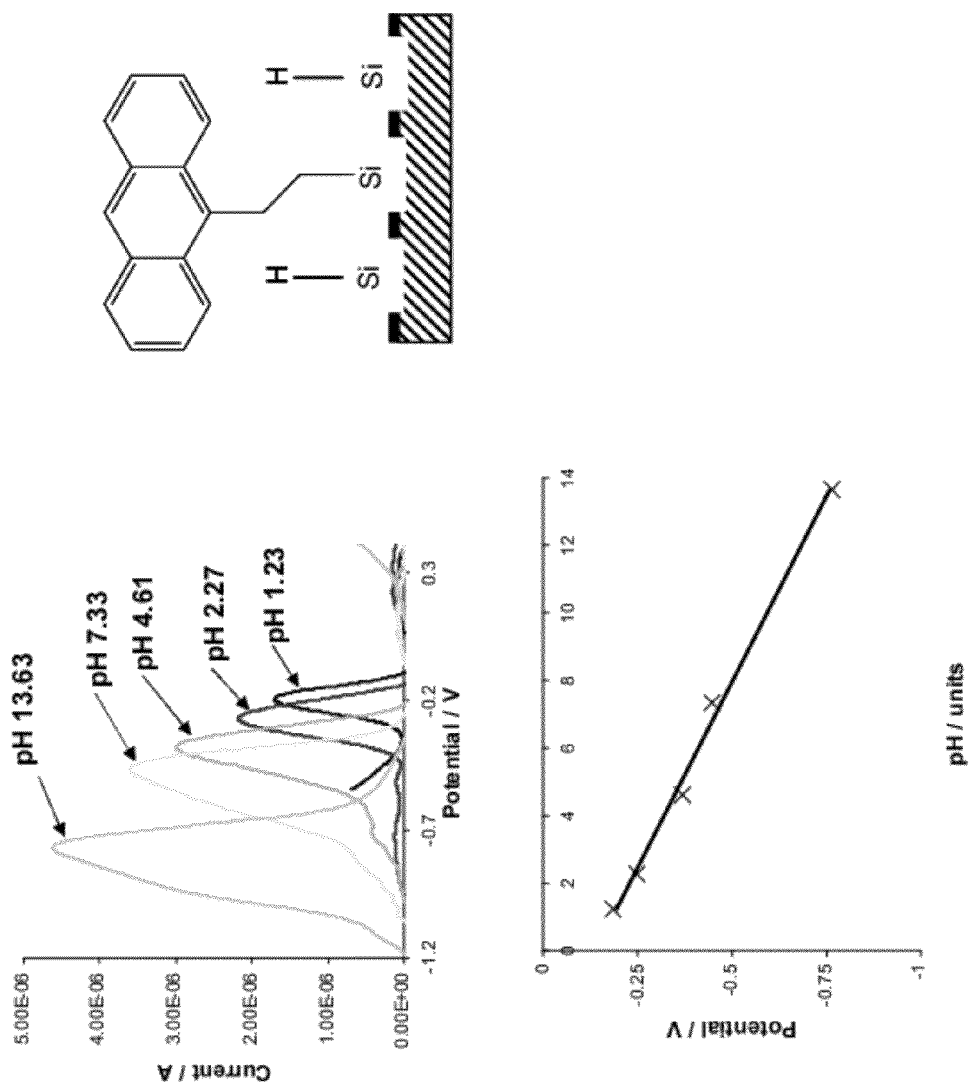
Figure 10

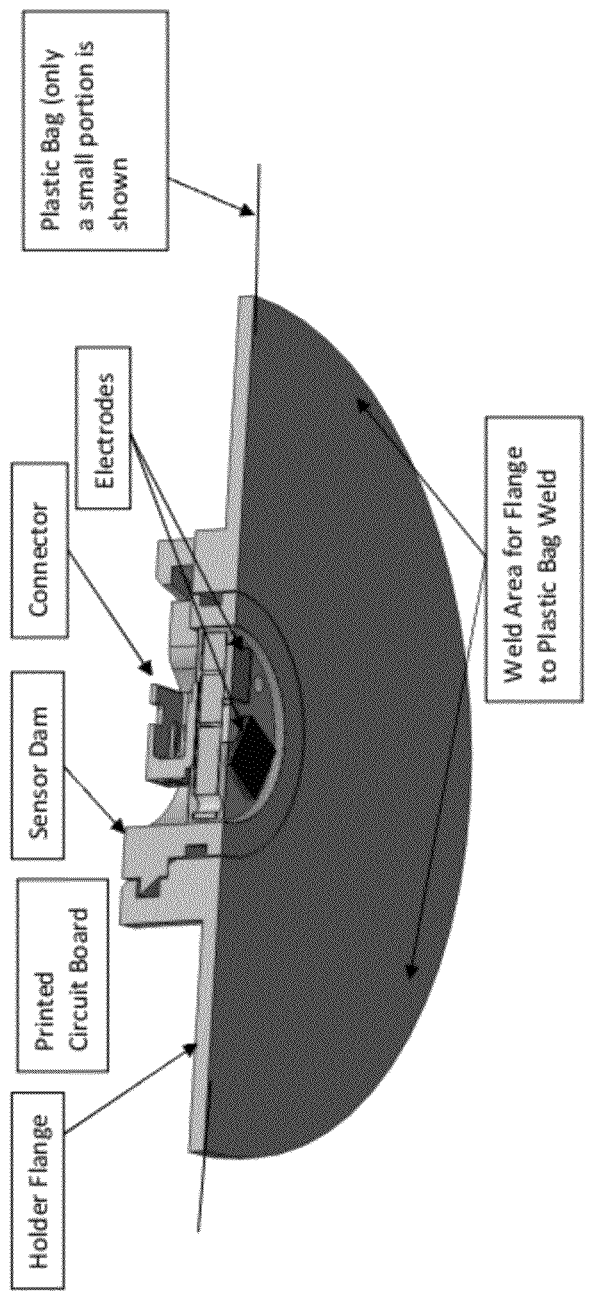

Head portion

3202

3201

ELECTROCHEMICAL SENSORS

CROSS-REFERENCE

This application claims priority to U.S. Provisional Patent Application Ser. No. 61/424,040, filed Dec. 16, 2010, and U.S. Provisional Patent Application Ser. No. 61/550,355, filed Oct. 21, 2011, which are entirely incorporated herein by reference.

BACKGROUND OF THE INVENTION

The measurement of analyte concentration, in particular, hydrogen ion concentration or pH is important in a number of research, industrial, and manufacturing processes. For instance, the measurement of pH is routinely practiced in food and beverage, biofuel, biophamaceuticals, as well as in the treatment of water and waste.

Many conventional pH sensors use a potentiometric approach which involves the use of glass electrode to measure pH. The potentiometric approach suffers from several drawbacks. One limitation of potentiometric sensors is the need for constant calibration. Potentiometric pH electrodes, like batteries, tend to run down with time and use. As the potentiometric electrode ages, its glass membrane tends to change in resistance, which in turn will alter the electrode potential. For this reason, the glass electrodes require calibration on a regular basis. The need for constant recalibration to provide an accurate pH output significantly impedes industrial applications especially where constant in-line pH measurements are required. Recalibration is particularly cumbersome in a biotech environment where pH measurement is conducted in medium containing biological materials. Another significant drawback of conventional pH sensors is that the glass electrodes have internal solutions, which in some cases can leak out into the solution being measured. The glass electrodes can also become fouled by species in the measuring solution, e.g., proteins, causing the glass electrode to foul. ISFET devices have been developed which use a field effect transistor structure on a silicon surface to measure pH (Bergveld E m et al., IEEE Sensor Conference, Toronto, October 2003, 1-26). These devices also have limitations. Thus, there remains a considerable need for reliable and consistent analyte sensors, and in particular, pH sensors.

SUMMARY OF THE INVENTION

An aspect of the invention provides a sensor for detecting the presence of an analyte comprising: a semiconductor electrode having a surface having immobilized thereon a redox-active moiety, wherein the redox-active moiety exhibits an oxidation potential and/or a reduction potential that is sensitive to the presence of the analyte. In some embodiments the analyte is hydrogen ion and the redox-active moiety is sensitive to hydrogen ion concentration. In some embodiments the sensor comprises a plurality of redox-active moieties, wherein at least one of the redox-active moieties is sensitive to the presence of an analyte, and at least one other redox-active moiety is substantially insensitive to the presence of the analyte.

In some embodiments the analyte is hydrogen ion, and the moiety that is substantially insensitive to the presence of hydrogen ion has a substituent selected from the group consisting of ferrocene, polyvinylferrocene, viologen, polyviologen, and polythiophene. In some embodiments the moiety that is substantially insensitive to the presence of hydrogen ion is ferrocene or a derivative of ferrocene.

In some embodiments the analyte is hydrogen, and the redox-active moiety that is sensitive to the presence of the hydrogen ion comprises a substituent selected from the group consisting of anthracenes, quinones, anthroquinones, phenanthroquinones, phenylene diamines, catechols, phenothiazinium dyes, monoquaternized N-alkyl-4,4'-bipyridinium, RuOx, and Ni(OH)2. In some embodiments the redox-active moiety that is sensitive to the presence of hydrogen ion comprises a substituent comprising anthracene. In some embodiments the redox-active moiety that is sensitive to the presence of hydrogen ion comprises a substituent comprising an anthraquinone or a phenanthraquinone.

In some embodiments the redox-active moiety that is sensitive to the presence of an analyte is sensitive to the concentration of the analyte. In some embodiments the oxidation potential and/or reduction potential of the redox-active moiety is sensitive to the concentration of the analyte in a range from $10^{-3}$ M to $10^{-10}$ M. In some embodiments oxidation potential and/or reduction potential of the redox-active moiety is sensitive to the concentration of the analyte in a range from $10^{-1}$ M to $10^{-14}$ M. In some embodiments the sensor detects hydrogen ion concentration from pH 3 to pH 10. In some embodiments the sensor detects hydrogen ion concentration from pH 1 to pH 14.

In some embodiments the sensor measures hydrogen ion concentration within an accuracy of plus or minus 0.1 pH unit. In some embodiments the sensor measures hydrogen ion concentration within an accuracy of plus or minus 0.01 pH units.

In some embodiments the redox-active moiety is covalently bound to the surface of the electrode. In some embodiments the redox-active moiety is bound to a polymer that is immobilized onto the surface of the electrode.

In some embodiments the semiconductor electrode is doped. In some embodiments the semiconductor electrode is P-doped. In some embodiments the semiconductor electrode comprises a silicon electrode doped with boron. In some embodiments the semiconductor electrode is N-doped. In some embodiments the semiconductor electrode comprises a silicon electrode is doped with phosphorous.

In some embodiments the semiconductor electrode comprises a monolithic piece of silicon.

In some embodiments the semiconductor electrode comprises a composite electrode, the composite electrode comprising semiconductor particles in a matrix. In some embodiments the semiconductor electrode comprises a composite electrode bound to a conductive substrate. In some embodiments the semiconductor particles are present in an amount such that a conductive path is created across the composite electrode.

In some embodiments the electrode comprises silicon. In some embodiments the electrode comprises unpolished silicon. In some embodiments the electrode comprises polished silicon.

In some embodiments the semiconductor electrode has a resistivity within the range of 0.01 to 1000 Ω-cm. In some embodiments the semiconductor electrode has a resistivity within the range of 1 to 100 Ω-cm.

In some embodiments the sensor is capable of measuring analyte concentration without calibration with an external standard. In some embodiments the sensor remains sensitive to the analyte without calibration after a first use by an end user. In some embodiments the analyte is hydrogen ion and the sensor remains sensitive to hydrogen ion after exposure to a cell culture medium for at least 6 days. In some embodiments the sensor is capable of measuring pH with an accuracy of plus or minus 0.2 pH units after exposure to the cell culture medium for at least 6 days. In some embodiments the analyte is hydrogen ion and the sensor is capable of measuring pH with an accuracy of plus or minus 0.2 pH units after autoclave treatment at 121° C. for 40 minutes. In some embodiments the sensor is capable of measuring pH with an accuracy of plus or minus 0.2 units after autoclave treatment at 121° C. for 400 minutes.

In some embodiments the semiconductor substrate has a plurality of zones wherein at least a first zone is sensitive to an analyte, and a second zone that is insensitive to an analyte.

Another aspect of the invention provides an analyte-sensing system comprising: a working electrode having a semiconductor surface that has immobilized thereon a redox-active moiety, wherein the redox-active moiety has an oxidation potential and/or reduction potential that is sensitive to the presence of the analyte; a counter electrode and optionally a reference electrode; a source for supplying a plurality of potentials to the working electrode; and a device for measuring current through the working electrode at the plurality of potentials.

In some embodiments the invention further comprises a second working electrode comprising a second semiconductor substrate comprising a second redox-active moiety having an oxidation potential and/or reduction potential that is insensitive to the presence of the analyte. In some embodiments the source for supplying a plurality of potentials is a potentiostat capable of applying square waves for square wave voltammetry.

In some embodiments the invention further comprises a computation system that communicates with the device for measuring current, and that calculates a reduction or oxidation potential from the measured current at a plurality of potentials.

In some embodiments the system is used as an in-line sensor in a process.

In some embodiments the currents measured at a plurality of potentials are used to determine analyte concentration, and the determined analyte concentration is used to control a process parameter.

In some embodiments the sensor measures hydrogen ion concentration within an accuracy of plus or minus 0.1 pH unit. In some embodiments the sensor measures hydrogen ion concentration within an accuracy of plus or minus 0.01 pH units.

In some embodiments the sensor is capable of measuring analyte concentration without calibration with an external standard. In some embodiments the sensor remains sensitive to the analyte without calibration after a first use by an end user. In some embodiments the analyte is hydrogen ion and the sensor remains sensitive to hydrogen ion after exposure to a cell culture medium for at least 6 days. In some embodiments the sensor is capable of measuring pH with an accuracy of plus or minus 0.2 units after exposure to the cell culture medium for at least 6 days. In some embodiments the analyte is hydrogen ion and the sensor is capable of measuring pH with an accuracy of plus or minus 0.2 units after autoclave treatment at 121° C. for 40 minutes. In some embodiments the sensor is capable of measuring pH with an accuracy of plus or minus 0.2 units after autoclave treatment at 121° C. for 400 minutes.

Another aspect of the invention provides a semiconductor substrate having a surface, wherein the surface comprises a redox-active moiety immobilized thereon, the redox-active moiety exhibiting an oxidation potential and/or a reduction potential that is sensitive to the presence of an analyte.

In some embodiments immobilized thereon is also a second redox-active moiety having an oxidation potential and/or a reduction potential that is substantially insensitive to the presence of the analyte.

In some embodiments the analyte is an ion. In some embodiments the analyte is hydrogen ion. In other embodiments, the analyte is a polarizable molecule. In other embodiments, the analyte is an ionizable molecule, such as upon the application of an external source of energy.

In some embodiments the semiconductor comprises an inorganic semiconductor. In some embodiments the semiconductor comprises an organic semiconductor. In some embodiments the inorganic semiconductor comprises silicon or gallium arsenide. In some embodiments the organic semiconductor comprises polyacetylene, polythiophene, or polypyrrole.

In some embodiments the semiconductor comprises silicon. In some embodiments the semiconductor comprises unpolished silicon. In some embodiments the semiconductor comprises polished silicon.

In some embodiments the redox-active moiety is directly bound to the surface. In some embodiments the redox-active moiety is covalently bound to the surface. In some embodiments the redox-active moiety is covalently bound to the surface through a linker. In some embodiments the redox-active moiety is covalently bound to a polymer that is immobilized onto the surface of the semiconductor substrate. In some embodiments the redox-active moiety is covalently bound to a polymer that is covalently bound to the surface of the semiconductor substrate In some embodiments the semiconductor is doped. In some embodiments the semiconductor is N-doped. In some embodiments the semiconductor is P-doped.

In some embodiments substrate comprises crystalline silicon wherein the surface displaying predominantly one crystalline plane.

In some embodiments the substrate has a plurality of zones wherein each zone comprises a redox-active moiety immobilized thereon, the redox-active moiety exhibiting an oxidation potential and/or a reduction potential that is sensitive to the presence of an analyte. In some embodiments a first zone comprises a redox moiety sensitive to a first analyte, and a second zone comprises a redox moiety sensitive to a second analyte. In some embodiments the invention further comprises a third redox-active moiety exhibiting an oxidation potential and/or a reduction potential that is sensitive to the presence of a second analyte. In some embodiments the second analyte is ammonia, oxygen or carbon dioxide.

Another aspect of the invention provides a method for forming an analyte-sensitive semiconductor electrode, the electrode having a surface, the method comprising immobilizing a redox-active moiety that is sensitive to the presence of an analyte onto the surface. In some embodiments immobilizing the redox-active moiety covalently binds the redox-active moiety to the surface. In some embodiments the redox-active moiety is covalently bound to the surface through a linker. In some embodiments immobilizing the redox-active moiety comprises hydrosilation, a free radical reaction, carbodiimide coupling, a Diels-Alder reaction, a Michael addition, or click chemistry.

In some embodiments the redox-active moiety is covalently bound to a polymer that is immobilized onto the surface.

In some embodiments the step of immobilizing comprises polymerization including a monomer or oligomer comprising a redox-active moiety. In some embodiments the polymerization of a monomer or oligomer comprising a redox-active moiety includes a reaction with a functional group covalently bound to the surface, whereby the polymer formed by polymerization is covalently bound to the surface. In some embodiments the monomer or oligomer is electropolymerized onto the surface.

In some embodiments the step of immobilizing comprises coating or casting the polymer onto the surface.

In some embodiments the semiconductor surface comprises a composite electrode that comprises semiconductor particles within a matrix.

Another aspect of the invention provides a method for forming a semiconductor surface derivatized with one or more redox-active moieties comprising: contacting an H-terminated semiconductor surface with the one or more redox-active moieties wherein at least one redox active moiety is sensitive to the presence of an analyte, and wherein each redox-active moiety comprises a functional group that will react with the H-terminated semiconductor surface to form a covalently bond, thereby forming a derivatized semiconductor surface.

In some embodiments the semiconductor surface comprises silicon.

In some embodiments at least two redox active moieties are used, and one of the redox active moieties is insensitive to the presence of the analyte.

In some embodiments the H-terminated semiconductor surface is formed by treatment with hydrofluoric acid.

In some embodiments the functional group is a vinyl group. In some embodiments the functional group is an aldehyde group. In some embodiments the functional group is a diazonium group.

Another aspect of the invention provides a method of determining the concentration of an analyte, comprising placing an electrode in contact with the analyte, the electrode comprising a semiconductor substrate with a semiconductor surface having immobilized thereon an analyte-sensitive redox-active moiety, the analyte-sensitive redox-active moiety exhibiting an oxidation potential and/or reduction potential that is sensitive to the concentration of the analyte; applying a plurality of potentials to the electrode; and measuring the current through the electrode at the plurality of potentials to determine a reduction and/or oxidation potential of the analyte-sensitive redox-active moiety, thereby determining the concentration of the analyte.

In some embodiments the measuring of the current at the plurality of potentials provides a peak current, and whereby the peak current is used to determine reduction and/or oxidation potential of the analyte-sensitive redox-active moiety.

In some embodiments the analyte is hydrogen ion.

In some embodiments the invention further comprises an analyte-insensitive redox-active moiety bound to a an electrode comprising a semiconductor substrate, such redox-active moiety having a reduction and/or oxidation potential that is substantially insensitive to the analyte, further comprising determining the oxidation and/or reduction potential of the analyte-insensitive redox-active moiety, and determining the concentration of the analyte from the difference in the oxidation and/or reduction potentials of the analyte-sensitive and analyte-insensitive moieties.

In some embodiments the analyte is provided in a solution.

Another aspect of the invention provides a sensor for detecting the presence of an analyte. The sensor comprises a semiconductor electrode having a surface having immobilized thereon a layer of a redox-active moiety, wherein the redox-active moiety exhibits an oxidation potential and/or a reduction potential that is sensitive or insensitive to the presence of the analyte, and a layer of composite material on, over or adjacent to the layer of the redox-active moiety. In some cases, the layer of the composite material covers the layer of the redox-active moiety.

In some embodiments, the composite material comprises Nafion. In some cases, the composite material comprises a porous material, such as a porous polymeric material (e.g., plastic), impregnated with Nafion.

In some situations, a working electrode comprises a layer of a polymeric material for shielding light-sensitive moieties on or over the working electrode from light. In some cases, the layer of the polymeric material comprises polyethersulphone (PES).

In another aspect of the invention, an electrochemical sensor comprises a solid state (e.g., a semiconductor, such as silicon, or carbon) electrode that is equipped with (or operatively coupled to) a light emitting device (also "light source" herein).

In some embodiments, a sensor comprises a light-emitting device, such as a light-emitting diode, and a layer of a semiconducting or a non-semiconducting material over the light emitting device. The layer of the semiconducting or non-semiconducting material may have a redox sensitive moiety thereon.

In some embodiments, the light-emitting diode is an organic light-emitting diode. In some embodiments, the semiconducting material is silicon. In some embodiments, the non-semiconducting material is carbon, such as activated carbon.

In another embodiment, a sensor for detecting the presence or absence of an analyte comprises an electrode having a surface having immobilized thereon a redox-active moiety, wherein the redox-active moiety exhibits an oxidation potential and/or a reduction potential that is sensitive or insensitive to the presence of the analyte. A light-emitting device is adjacent to the electrode. The light-emitting device is configured to generate light.

In some embodiments, a solid state sensor for detecting the presence or absence of an analyte, comprises a solid state electrode configured to detect the presence or absence of the analyte, and a light emitting device adjacent to the solid state electrode.

In some embodiments, a sensor for detecting the presence or absence of an analyte, comprising a working electrode having a redox active moiety formed adjacent a light emitting device, is provided.

In another aspect of the invention, a sensor for detecting the presence or absence of an analyte comprises a semiconductor electrode having a surface having immobilized thereon a layer of a redox-active moiety, wherein the redox-active moiety exhibits an oxidation potential and/or a reduction potential that is sensitive or insensitive to the presence of the analyte. A light blocking layer is adjacent to the layer of the redox-active moiety.

In some embodiments, a solid state sensor for detecting the presence or absence of an analyte, comprises a solid state electrode and a light blocking layer adjacent to the solid state electrode. The light blocking layer may be formed of a polymeric material. In some situations, the light blocking layer transmits less than 10%, 5%, or 1% of light incident on the light blocking layer.

Another aspect of the invention is a method comprising: measuring a pH value of a step in a water or waste treatment process with a voltammetric pH sensor, wherein the pH sensor comprises a redox-active moiety that is sensitive to hydrogen ion concentration, and a redox-active moiety that is substantially insensitive to hydrogen ion; and using the pH value to monitor or control the treatment process.

Another aspect of the invention provides a method comprising measuring a pH value of a reaction mixture in a biopharmaceutical process with a voltammetric pH sensor, wherein the pH sensor comprises a redox-active moiety that is sensitive to hydrogen ion concentration, and a redox-active moiety that is substantially insensitive to hydrogen ion concentration to obtain a pH value. The pH value is used to monitor the biopharmaceutical process.

In some embodiments the pH value is measured on a sample obtained from the reaction mixture.

Another aspect of the invention provides a reactor for carrying out a biopharmaceutical process wherein the reactor comprises a pH sensor having a redox-active moiety that is sensitive to hydrogen ion concentration, and a redox-active moiety that is substantially insensitive to hydrogen ion concentration.

In some embodiments the pH sensor is a voltammetric pH sensor.

In an embodiment, the pH sensor is a disposable pH sensor. In another embodiment, the pH sensor is a single-use pH sensor. In another embodiment, the pH sensor is a disposable and single-use pH sensor.

In some embodiments the reactor is a disposable bioreactor. In some embodiments the reactor is a bioprocess flexible container.

Another aspect of the invention provides a method for carrying out an industrial process comprising: measuring a pH value of a step of an industrial process with a voltammetric pH sensor having a redox-active moiety that is sensitive to hydrogen ion concentration, and a redox-active moiety that is substantially insensitive to hydrogen ion concentration; and using the pH value to carry out the industrial process.

Another aspect of the invention provides a sensor for measuring ion concentration in a bodily fluid within a body. The sensor comprises an electrode configured to be in contact with a bodily fluid, the electrode comprising a semiconductor surface that has immobilized thereon a redox-active moiety. The redox-active moiety has an oxidation potential and/or reduction potential that is sensitive to concentration of the ion.

Another aspect of the invention provides a method for measuring concentration in a bodily fluid within a body, comprising placing such a sensor in contact with the bodily fluid and operating the sensor to yield a value of the concentration of the ion present in the bodily fluid.

Another aspect of the invention provides a bioreactor comprising a reservoir for containing a reaction mixture and a pH probe wherein the pH probe comprises an electrode having a semiconductor surface, the semiconductor surface having immobilized thereon a redox active moiety having a reduction and/or oxidation potential that is sensitive to the presence of hydrogen ion.

In some embodiments the invention further comprises a semiconductor surface having immobilized thereon a redox active moiety having a reduction and/or oxidation potential that is insensitive to the presence of hydrogen ion.

In some embodiments the semiconductor surface on which the redox active moiety having a reduction and/or oxidation potential that is sensitive to the presence of hydrogen ion is immobilized is the same semiconductor surface on which the redox active moiety having a reduction and/or oxidation potential that is insensitive to the presence of hydrogen ion is immobilized on. In some embodiments the probe further comprises a counter electrode.

Another aspect of the invention provides a sensor system, comprising a redox-active moiety-containing analyte sensor for insertion into a container for use with a glass probe analyte sensor. In an embodiment, the redox-active moiety-containing analyte sensor comprises one or more redox-active moieties. In another embodiment, the redox-active moiety-containing analyte sensor comprises a redox-active moiety that is sensitive to the presence of an analyte and another redox-active moiety that is insensitive to the presence of the analyte. In another embodiment, the redox-active moiety-containing analyte sensor is disposed in a probe body having a form factor configured for insertion into a container for use with a glass probe analyte sensor.

Another aspect of the invention provides a method for detecting the presence or absence of an analyte, comprising using a sensor system, as described above, to detect the presence or absence of the analyte.

Another aspect of the invention provides a method for forming an analyte sensor, comprising inserting a sensor system as described herein into a container configured for use with a glass probe analyte sensor. In an embodiment, the method further comprises removing a glass probe analyte sensor from the container prior to inserting the sensor system into the container.

Another aspect of the invention provides a method for forming an analyte sensor, comprising inserting a sensor system as described herein into a container configured for use with a reactor, in-line flow system, or sample preparation, or analysis.

Another aspect of the invention provides a sensor for detecting the presence or absence of an analyte, comprising a semiconductor electrode having a surface having immobilized thereon a redox-active moiety, wherein the redox-active moiety exhibits an oxidation potential and/or a reduction potential that is sensitive to the presence of the analyte. The sensor includes a form factor for insertion into a container of a glass probe analyte sensor.

In an embodiment, the analyte is hydrogen ion and the redox-active moiety is sensitive to hydrogen ion concentration. In another embodiment, the sensor comprises a plurality of redox-active moieties, wherein at least one of the redox-active moieties is sensitive to the presence of an analyte, and at least one other redox-active moiety is substantially insensitive to the presence of the analyte. In another embodiment, the analyte is hydrogen ion, and the moiety that is substantially insensitive to the presence of hydrogen ion has a substituent selected from the group consisting of ferrocene, polyvinylferrocene, viologen, polyviologen, and polythiophene. In another embodiment, the moiety that is substantially insensitive to the presence of hydrogen ion is ferrocene or a derivative of ferrocene. In another embodiment, the analyte is hydrogen, and the redox-active moiety that is sensitive to the presence of the hydrogen ion comprises a substituent selected from the group consisting of anthracenes, quinones, anthroquinones, phenanthroquinones, phenylene diamines, catechols, phenothiazinium dyes, monoquaternized N-alkyl-4,4'-bipyridinium, RuOx, and $Ni(OH)_2$. In another embodiment, the redox-active moiety that is sensitive to the presence of hydrogen ion comprises a substituent comprising anthracene. In another embodiment, the redox-active moiety that is sensitive to the presence of hydrogen ion comprises a substituent comprising an anthraquinone or a phenanthraquinone. In another embodiment, the redox-active moiety that is sensitive to the presence of an analyte is sensitive to the concentration of the analyte. In another embodiment, the oxidation potential and/or reduction potential of the redox-active moiety is sensitive to the concentration of the analyte in a range from $10^{-3}$ M to $10^{-10}$ M. In another embodiment, the oxidation potential and/or reduction potential of the redox-active moiety is sensitive to the concentration of the analyte in a range from $10^{-1}$ M to $10^{-14}$ M.

In an embodiment, the sensor detects hydrogen ion concentration from pH 1 to pH 14. In another embodiment, the sensor detects hydrogen ion concentration from pH 3 to pH 10. In another embodiment, the sensor measures hydrogen ion concentration within an accuracy of plus or minus 0.1 pH units. In another embodiment, the sensor measures hydrogen ion concentration within an accuracy of plus or minus 0.01 pH units.

In an embodiment, the redox-active moiety is covalently bound to the surface of the electrode, such as through an oxygen-to-surface, carbon-to-surface or sulfur-to-surface bond. In another embodiment, the redox-active moiety is bound to a polymer that is immobilized onto the surface of the electrode.

In an embodiment, the semiconductor electrode is doped. In another embodiment, the semiconductor electrode is p-doped. In another embodiment, the semiconductor electrode is doped with boron. In another embodiment, the semiconductor electrode is n-doped. In another embodiment, the semiconductor electrode is doped with phosphorous. In another embodiment, the semiconductor electrode comprises a monolithic piece of silicon. In another embodiment, the semiconductor electrode comprises a composite electrode, the composite electrode comprising semiconductor particles in a matrix. In another embodiment, the semiconductor electrode comprises a composite electrode bound to a conductive substrate. In another embodiment, the semiconductor particles are present in an amount such that a conductive path is created across the composite electrode. In another embodiment, the electrode comprises silicon. In another embodiment, the electrode comprises unpolished silicon. In another embodiment, the electrode comprises polished silicon. In another embodiment, the semiconductor electrode has a resistivity within the range of about 0.01 to 1000 $\Omega$-cm. In another embodiment, the semiconductor electrode has a resistivity within the range of 1 to 100 $\Omega$-cm.

In an embodiment, the sensor is capable of measuring analyte concentration without calibration with an external standard. In another embodiment, the sensor remains sensitive to the analyte without calibration after a first use by an end user. In another embodiment, the analyte is hydrogen ion and the sensor remains sensitive to hydrogen ion after exposure to a cell culture medium for at least 6 days. In another embodiment, the sensor is capable of measuring pH with an accuracy of plus or minus 0.2 pH units after exposure to the cell culture medium for at least 6 days. In another embodiment, the analyte is hydrogen ion and the sensor is capable of measuring pH with an accuracy of plus or minus 0.2 pH units after autoclave treatment at 121° C. for 40 minutes. In another embodiment, the sensor is capable of measuring pH with an accuracy of plus or minus 0.2 pH units after autoclave treatment at 121° C. for 400 minutes. In another embodiment, the semiconductor substrate has a plurality of zones, wherein at least a first zone is sensitive to an analyte and a second zone is insensitive to an analyte.

In an embodiment, the container is cylindrical in shape. In another embodiment, the container has a circular cross-section. In another embodiment, the container is formed of one or more metals. In another embodiment, the one or more metals include stainless steel.

Another aspect of the invention provides a sensor comprising a solid state electrode having a surface immobilized thereon a mixed layer of hydrocarbon molecules and redox-active moieties. In an embodiment, the redox-active moieties are sensitive to an analyte, such as hydrogen. In another embodiment, the redox-active moieties are insensitive to the analyte.

Another aspect of the invention provides a sensor for detecting the presence or absence of an analyte, comprising a semiconductor electrode having a surface having immobilized thereon a layer of a redox-active moiety, wherein the redox-active moiety exhibits an oxidation potential and/or a reduction potential that is sensitive or insensitive to the presence of the analyte. The sensor further comprises a light blocking layer adjacent to the layer of the redox-active moiety. In an embodiment, the light blocking layer comprises a polymeric material. In another embodiment, the polymeric material comprises a fluoropolymer-copolymer. In another embodiment, the polymeric material comprises Nation. In another embodiment, the sensor further comprises a protective layer adjacent to the light blocking layer. In another embodiment, the protective layer comprises a polymeric material. In another embodiment, the polymeric material comprises polyethersulphone.

In an embodiment, the light blocking layer comprises a composite material. In another embodiment, the composite material comprises Nation. In another embodiment, the composite material comprises a porous plastic. In another embodiment, the composite material is a porous membrane.

Another aspect of the invention provides a redox-active moiety-containing analyte sensor for use with a glass probe analyte detection system. The redox-active moiety-containing analyte sensor can have any of the features and characteristics of sensors described above.

Another aspect of the invention provides a redox-active moiety-containing analyte sensor for use in a time period of about 1 day, or 5 days, or 10 days, or 20 days, or 25 days, or 30 days. The redox-active moiety-containing analyte sensor can have any of the features and characteristics of sensors described above.

Another aspect of the invention provides a redox-active moiety-containing analyte sensor having a sensitivity between about 20 mV per pH unit and 60 mV per pH unit. The redox-active moiety-containing analyte sensor can have any of the features and characteristics of sensors described above.

Another aspect of the invention provides a redox-active moiety-containing analyte sensor having a shelf life between about 3 months and 3 years. The redox-active moiety-containing analyte sensor can have any of the features and characteristics of sensors described above.

Another aspect of the invention provides a sensor for detecting an analyte having an accuracy to within 0.001 pH units while in use or storage for at least 2 years. The redox-active moiety-containing analyte sensor can have any of the features and characteristics of sensors described above.

Another aspect of the invention provides a sensor for detecting an analyte having an accuracy to within 0.001 pH units while in use or storage for at least 4 years. The redox-active moiety-containing analyte sensor can have any of the features and characteristics of sensors described above.

Another aspect of the invention provides a sensor for detecting an analyte having an accuracy to within 0.001 pH units while in use or storage for at least 8 years. The redox-active moiety-containing analyte sensor can have any of the features and characteristics of sensors described above.

Another aspect of the invention provides a sensor for detecting an analyte having an accuracy to within 0.001 pH units while in use or storage for at least 10 years. The redox-active moiety-containing analyte sensor can have any of the features and characteristics of sensors described above.

Another aspect of the invention provides a sensor for detecting the presence or absence of an analyte, comprising an electrode having a surface having immobilized thereon a redox-active moiety, wherein the redox-active moiety exhibits an oxidation potential and/or a reduction potential that is sensitive or insensitive to the presence of the analyte, and a light-emitting device adjacent to the electrode, the light-emitting device configured to generate light. In an embodiment, the light-emitting device is configured to generate light that is i) incident on the surface, ii) incident on another surface of the electrode, the another surface opposite from the surface, and/or iii) directed through the electrode. In another embodiment, the electrode is formed of a solid state material. In another embodiment, the electrode is formed of a semiconductor material. In another embodiment, the semiconductor material includes silicon. In another embodiment, the electrode is formed of a non-semiconductor material. In another embodiment, the non-semiconductor material includes carbon. In another embodiment, the light-emitting device is a light-emitting diode having an active region configured to generate light upon the recombination of electrons and holes. In another embodiment, the light-emitting diode is an organic light-emitting diode. In another embodiment, during use, light from the light-emitting device is incident on the surface.

Another aspect of the invention provides a sensor for detecting the presence or absence of an analyte, comprising a working electrode having a redox active moiety formed adjacent a light emitting device. The sensor can have any of the features and characteristics of sensors described above.

Another aspect of the invention provides a solid state sensor for detecting the presence or absence of an analyte, comprising a solid state electrode and a light blocking layer adjacent to the solid state electrode. In an embodiment, the light blocking layer is formed of a polymeric material. In another embodiment, the light blocking layer transmits less than 10% of light incident on the light blocking layer. In another embodiment, the light blocking layer transmits less than 5% of light incident on the light blocking layer. In another embodiment, the light blocking layer transmits less than 1% of light incident on the light blocking layer.

Another aspect of the invention provides a solid state sensor for detecting the presence or absence of an analyte, comprising a solid state electrode configured to detect the presence or absence of the analyte, and a light emitting device adjacent to the solid state electrode. The sensor can have any of the features and characteristics of sensors described above.

Another aspect of the invention provides a sensor for detecting the presence or absence of an analyte, comprising a working electrode having a redox active moiety formed adjacent a light emitting device. The sensor can have any of the features and characteristics of sensors described above.

Another aspect of the invention provides a method for detecting the presence or absence of an analyte, comprising bringing an analyte sensor in contact with a sample, the analyte sensor having an electrode having immobilized thereon a redox-active moiety. The redox-active moiety exhibits an oxidation potential and/or a reduction potential that is sensitive to the presence of the analyte. Next, with the aid of the analyte sensor, the analyte is detected at an accuracy within at least about 5% without re-calibration for a period of at least about 1 day. In an embodiment, the accuracy is within at least about 1%. In another embodiment, the accuracy is within at least about 0.1%. In another embodiment, the period is at least about 7 days. In another embodiment, the period is at least about 1 month. In another embodiment, the period is at least about 1 year. In another embodiment, the period is at least about 2 years.

Another aspect of the invention provides a method for detecting the presence or absence of an analyte, comprising using a sensor, as described above, to detect the presence or absence of the analyte. In some embodiments, the analyte is hydrogen ion.

Another aspect of the invention provides a sensor having a solid state working electrode having disposed thereon a redox-active moiety exhibiting an oxidation potential and/or a reduction potential that is sensitive to the presence of an analyte. The working electrode has a size and shape for use in glass probe sensor, a reactor, a flow system, or a sample separation system. In an embodiment, the reactor is a bioreactor. In another embodiment, the sensor further comprises an additional working electrode having disposed thereon a redox-active moiety exhibiting an oxidation potential and/or reduction potential that is insensitive to the presence of the analyte. In another embodiment, the working electrode is doped p-type and the additional working electrode is doped n-type or p-type. In another embodiment, the working electrode has a resistivity is greater than or equal to about 1 $\Omega$-cm and the additional working electrode has a resistivity greater than or equal to about 5 $\mu\Omega$-cm.

Another aspect of the invention provides an analyte sensor, comprising a first solid state working electrode and a second solid state working electrode. The first solid state working electrode has disposed thereon a redox-active moiety exhibiting an oxidation potential and/or a reduction potential that is sensitive to the presence of an analyte, the first solid state working electrode doped p-type. The second solid state working electrode has disposed thereon a redox-active moiety exhibiting an oxidation potential and/or a reduction potential that is insensitive to the presence of the analyte, the second solid state working electrode doped n-type or p-type. In an embodiment, the first solid state working electrode is disposed adjacent to the second solid state working electrode. In another embodiment, the first solid state working electrode is electrically isolated from the second solid state working electrode. In another embodiment, the first solid state working electrode has a resistivity greater than or equal to 1 $\Omega$-cm (also "$\Omega$cm" herein). In another embodiment, the second solid state working electrode has a resistivity greater than or equal to about 5 $\mu\Omega$-cm. In another embodiment, the first and second solid state working electrodes are formed of a semiconductor. In another embodiment, the semiconductor is silicon. In another embodiment, the second solid state working electrode is doped n-type and has a resistivity greater than or equal to about 1 $\Omega$-cm. In another embodiment, the resistivity of the second solid state working electrode is between about 1 $\Omega$-cm and 90 $\Omega$-cm. In another embodiment, the solid state working electrodes are disposed on a substantially flat surface of the analyte sensor.

Another aspect of the invention provides a method for forming an analyte sensor, comprising inserting a sensor as described herein into a container that is for use with a glass probe analyte sensor. In an embodiment, the method further comprises removing a glass probe analyte sensor from the container prior to inserting the sensor into the container.

Another aspect of the invention provides a method for forming an analyte sensor, comprising inserting a sensor as described herein into a container that is for use with a reactor, in-line flow system, or sample preparation, or analysis.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The features and advantages of the invention may be further explained by reference to the following detailed description and accompanying drawings (or figures, also "Fig." and "FIG." herein) that sets forth illustrative embodiments.

FIG. 1(a) shows a blow up drawing illustrating an embodiment of the invention comprising a semiconductor electrode sensor in a housing assembly, in accordance with an embodiment of the invention. FIG. 1(b) shows an exemplary housing assembly comprising the semiconductor electrode sensor, in accordance with an embodiment of the invention;

FIG. 8 depicts a schematic diagram and picture of an exemplary electrochemical cell, in accordance with an embodiment of the invention;

FIG. 10(a) depicts square wave voltammograms showing the effect of pH on VA derivatized silicon sample at pH solutions of 1.23, 4.61, 7.33 (not shown; peak maximum between −0.4 and −0.6 V, to the left of the pH 4.61 peak and to the right of the pH 13.63 peak) and 13.63, in accordance with an embodiment of the invention. FIG. 10(b) depicts a plot of peak potential against pH using the VA derivatized silicon sample, in accordance with an embodiment of the invention;

FIG. 21(a) is a shaded drawing, and FIG. 21(b) is a line drawing;

FIG. 25A schematically illustrates an electrochemical sensor mounted on a wall of a disposable container, in accordance with an embodiment of the invention.

DETAILED DESCRIPTION OF THE INVENTION

Figure 2:
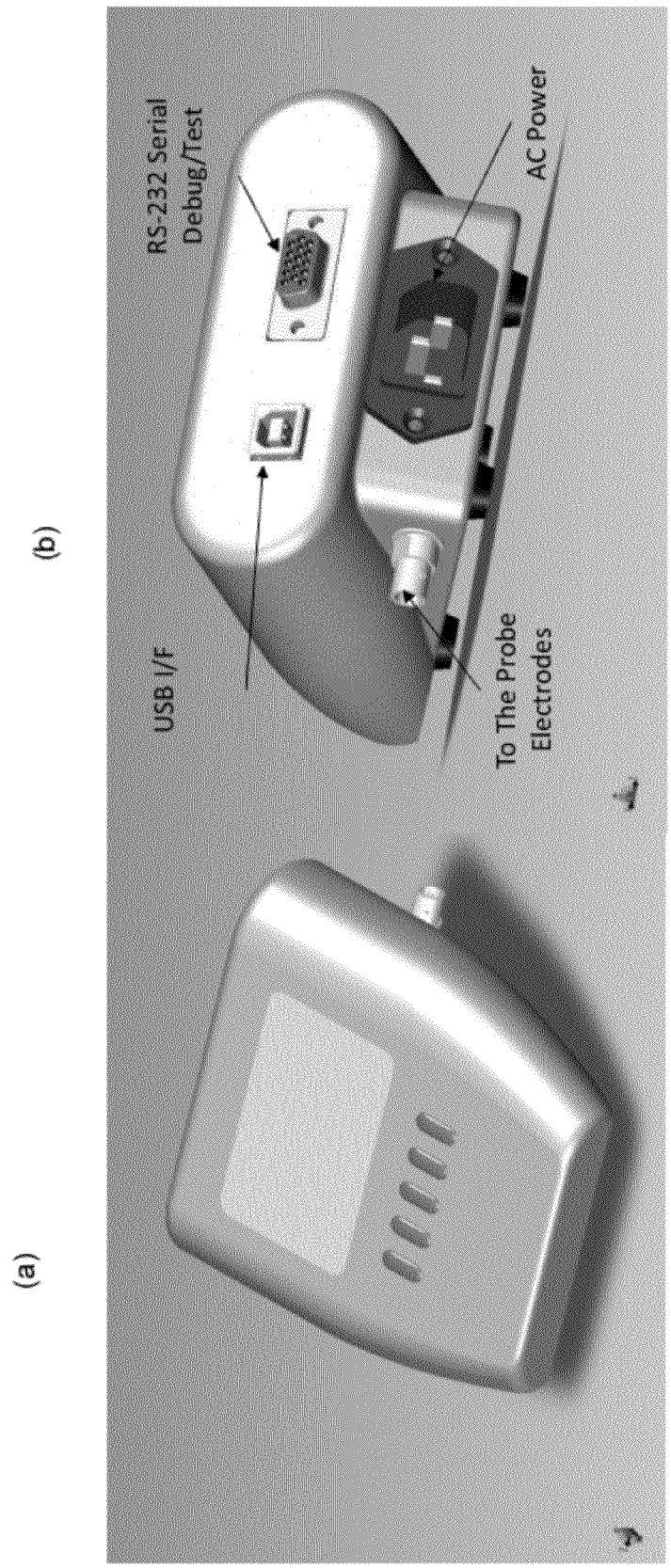
FIG. 2 depicts an embodiment of the invention comprising a unit that electrically connects to the semiconductor electrode sensor and comprising a source for supplying a plurality of potentials and a current measuring device, in accordance with an embodiment of the invention

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention relates to compositions, devices, systems, and methods for producing and using solid state electrodes modified with redox-active agents as sensors. The subject devices and systems are particularly useful for voltammetrically measuring concentrations of an analyte of interest. The sensors of the present invention utilize a solid state electrode comprising redox-active species on its surface. At least one redox-active species on the solid sate (e.g., semiconductor) surface has a redox potential (reduction potential or oxidation potential) that is sensitive to the presence and or amount of an analyte of interest. Voltammetry can be performed on the solid state electrode and used to measure the redox potential of the analyte-sensitive redox groups on the surface of the electrode. The measured value of the redox potential can then be used to determine the concentration of an analyte, for example an analyte in solution. In some embodiments, the solid state electrode of the present invention has more than one redox-active species. In an embodiment, at least one redox-active species is sensitive to the presence of an analyte (e.g., protons) and another redox-active species is insensitive to the presence of the analyte. Another aspect of the invention relates to the measurement of the concentration of hydrogen ion, or pH using the subject devices or systems. The surface modified solid state sensors of the present invention can be used to measure the pH of a variety of solutions. The surface modified sensors of the present invention are robust, reliable, accurate, and/or can be made such that they do not require calibration.

In some embodiments, solid state electrodes are formed of semiconductors. Semiconductors have advantages as substrates and sensors for the methods of the present invention. Semiconductors have band gaps that may be modified with the aid of chemical dopants, which can aid in preparing sensitive and accurate sensors. In addition, semiconductors can be less prone to fouling and degradation than other substrates.

Semiconductor surfaces, for example, inorganic semiconductors such as silicon and organic semiconductors, can be amenable to surface modification, e.g., covalent modification. Semiconductors generally have electronic band structures, the characteristics of which can be modified, for example, by doping. In some cases, the semiconductor that is used is silicon. An advantage of using silicon as a substrate and as an electrode is that silicon is amenable to mass production. In particular, semiconductor processing techniques are readily available for producing silicon electrodes in large quantities at low cost. In addition, existing semiconductor processing techniques make it feasible to integrate electronic functionality into the material comprising the silicon electrode. Another advantage of silicon is that it can form strong covalent bonds, for example with carbon, nitrogen, oxygen, thus allowing for the facile and robust modification of the surface in a manner required for its intended uses. For instance, a silicon surface can be modified to attachment of any suitable redox-active agent. Silicon is also an advantageous surface for carrying out voltammetry in that it is stable to a wide range of electrical potential without undergoing degradation.

An aspect of the invention is a surface modified solid state (e.g., semiconductor) redox sensor that can measure analyte concentration reliably and consistently with minimal intervention, such as re-calibration. Another aspect of the invention is a semiconductor redox sensor that does not require calibration or re-calibration. The ability to sense analytes, such as hydrogen ion without calibration has a number of advantages for analyte measurements, for example, for in-line monitoring. For example, it allows for ease of operator handling for single point measurements. In some embodiments, the sensors of the present invention are included in in-line operator-independent control measurements. Such in-line measurements can be made independent of the operator and can be used for process control, for example for pH measurements for process control. The subject sensors can be set to provide real-time measurements of an analyte, including, but not limited to real time-measurements of hydrogen ion concentration.

Semiconductor Substrates

An aspect of the invention provides an electrochemical sensor having a working electrode formed of a semiconductor substrate. The semiconductor substrate can comprise any suitable semiconductor material including those known in the art and those described herein. The semiconductor substrate can be an inorganic semiconductor or an organic semiconductor. The semiconductor substrate can be doped or undoped. In some embodiments the semiconductor substrate comprises silicon.

A semiconductor substrate of the invention is generally a solid material that has electrical conductivity in between that of a conductor and that of an insulator. The conductivity can vary over that wide range either permanently or dynamically.

Inorganic semiconductor substrates of the invention can comprise, for example, Group IV elemental semiconductors, such as diamond (C), silicon (Si), germanium (Ge); Group IV compound semiconductors, such as silicon carbide (SiC), silicon nitride (SiN), silicon germanide (SiGe), Group III-V semiconductors, such as aluminum antimonide (AlSb), aluminum arsenide (AlAs), aluminum nitride (AlN), aluminum phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP); Group III-V ternary semiconductor alloys, such as aluminum gallium arsenide (AlGaAs, AlxGal-xAs), indium gallium arsenide (InGaAs, InxGal-xAs), indium gallium phosphide (InGaP), aluminum indium arsenide (AlInAs), aluminum indium antimonide (AlInSb), gallium arsenide nitride (GaAsN), gallium arsenide phosphide (GaAsP), aluminum gallium nitride (AlGaN), aluminum gallium phosphide (AlGaP), indium gallium nitride (InGaN), indium arsenide antimonide (InAsSb), indium gallium antimonide (InGaSb), Group III-V quaternary semiconductor alloys, such as aluminum gallium indium phosphide (AlGaInP, also InAlGaP, InGaAlP, AlInGaP), aluminum gallium arsenide phosphide (AlGaAsP), indium gallium arsenide phosphide (InGaAsP), Aluminum indium arsenide phosphide (AlInAsP), aluminum gallium arsenide nitride (AlGaAsN), indium gallium arsenide nitride (InGaAsN), indium aluminum arsenide nitride (InAlAsN), gallium arsenide antimonide nitride (GaAsSbN), Group III-V quinary semiconductor alloys, such as gallium indium nitride arsenide antimonide (GaInNAsSb), gallium indium arsenide antimonide phosphide (GaInAsSbP), II-VI semiconductors, cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), Group II-VI ternary alloy semiconductors, such as cadmium zinc telluride (CdZnTe, CZT), mercury cadmium telluride (HgCdTe), mercury zinc telluride (HgZnTe), mercury zinc selenide (HgZnSe), Group I-VII semiconductors, such as cuprous chloride (CuCl), Group IV-VI semiconductors, such as lead selenide (PbSe), lead sulfide (PbS), lead telluride (PbTe), tin sulfide (SnS), tin telluride (SnTe), Group IV-VI ternary semiconductors, such as lead tin telluride (PbSnTe), Thallium tin telluride (Tl2SnTe5), thallium germanium telluride (Tl2GeTe5), Group V-VI semiconductors, such as bismuth telluride (Bi2Te3), and Group II-V semiconductors, such as cadmium phosphide (Cd3P2), cadmium arsenide (Cd3As2), cadmium antimonide (Cd3Sb2), zinc phosphide (Zn3P2), zinc arsenide (Zn3As2), and zinc antimonide (Zn3Sb2).

The inorganic semiconductor substrates of the invention can also comprise layered semiconductors, such as lead(II) iodide (PbI2), molybdenum disulfide (MoS2), gallium selenide (GaSe), tin sulfide (SnS), bismuth sulfide (Bi2S3), other semiconductors, such as copper indium gallium selenide (CIGS), platinum silicide (PtSi), bismuth(III) iodide (BiI3), mercury(II) iodide (Hg12), thallium(I) bromide (TlBr), and miscellaneous oxides, such as titanium dioxide: anatase (TiO2), copper(I) oxide (Cu2O), copper(II) oxide (CuO), uranium dioxide (UO2), and uranium trioxide (UO3).

In some embodiments of the invention, the semiconductor substrate can comprise an organic semiconductor. The organic semiconductor is any suitable organic material that has semiconductor properties. The organic semiconductor substrates of the invention can comprise, for example, small molecules, short chain (oligomers) and long chain (polymers). Examples of semiconducting small molecules (e.g., unsaturated and aromatic hydrocarbons) are pentacene, anthracene, rubrene, tetracene, chrysene, pyrene, perylene, coronene, metal complexes of porphine and phthalocyanine, compounds such as zinc 1,10,15,20-tetraphenyl-21H, 23H-porphine, copper phthalocyanine, lutetium bisphthalocyanine, and aluminum phthalocyanine chloride can be used. Suitable derivatives of these small molecules can also be used. In some embodiments, the organic semiconductor substrates of the invention can comprise thin films.

Examples of semiconducting polymers or oligomers include suitable conjugated hydrocarbon or heterocyclic polymers or oligomers. Suitable polymers or oligomers include: polyaniline, polypyrrole, and polythiophene, poly(3-hexylthiophene), poly(p-phenylene vinylene), F8BT, polyacetylene, polydiacetylene, polyacene, polyphenylene, poly(phenylene vinylene), polyfuran, polypyridine, poly(thienylene vinylene), poly(ferrocenyl vinylene phenylene vinylene), poly(fluorine), and poly(carbazole), and combinations thereof. Derivatives of these polymers, for instance derivatives having functional side chains amenable to the attachment of redox active species, can be used.

Other examples of semiconducting polymers are poly(anilinesulfonic acid), poly(ferrocenyl vinylene phenylene vinylene), poly(fluorine), and poly(carbazole). The organic semiconductor substrates of the invention can comprise, for example, organic charge-transfer complexes, and "linear backbone" polymers derived from polyacetylene, such as polyacetylene itself, polypyrrole, and polyaniline. Charge-transfer complexes can exhibit similar conduction mechanisms to inorganic semiconductors. This includes the presence of a hole and electron conduction layer and a band gap. The materials can exhibit tunneling, localized states, mobility gaps, and phonon-assisted hopping. Organic semiconductors can be doped. In some embodiments, the invention can utilize highly doped organic semiconductors, for example Polyaniline (Ormecon) and PEDOT:PSS. In some cases organic semiconductors can be produced such that they are transparent and/or flexible, which can be useful in some embodiments.

The semiconductors of the invention can typically be characterized as having a band gap, the band gap representing the amount of energy separating the valence and conduction bands of the semiconductor. The addition of dopants makes the band gap smaller, tending to allow more facile promotion of electrons from the valence band to the conduction band. A smaller band gap can result in higher conductivity for the semiconductor substrate. The band gap and conductivity characteristics of the semiconductor substrates can be controlled in some cases by the introduction of dopants. In some cases upon the addition of a sufficiently large proportion of dopants, the semiconductor substrates of the invention can conduct electricity nearly as well as metals. Depending on the kind of dopant or impurity, a doped region of semiconductor can have more electrons or holes, and is named N-type or P-type (herein also "n-type" and "p-type") semiconductor material, respectively. Junctions between regions of N- and P-type semiconductors create electric fields, which cause electrons and holes to be available to move away from them, and this effect is critical to semiconductor device operation. Also, a density difference in the amount of impurities produces a small electric field in the region which is used to accelerate non-equilibrium electrons or holes.

In some embodiments the presence of the band gap can be advantageous. For example, when performing electrochemistry, when the Fermi energy of a doped semiconductor lies at the same energy as the solution/molecular redox potential at a certain potential, generally no net transfer of charge/current will flow from the redox species (immobilized on the surface or in the solution) to the substrate or from the substrate to the redox species. This potential is sometimes referred to as the flatband potential. The location of the flatband potential can be influenced by dopant densities. The Mott-Schottky equation (see P. Schmuki, H. Bohni and J. A. Bardwell, J. Electrochem. Soc., 1995, 142, 1705) can be used to estimate the flat band potential.

A conductor electrode generally does not have a flatband potential thus has a broad potential window where current can flow from the redox species to the substrate. For example, when the conductor electrode is exposed to an aqueous solution containing a mixture of several redox active species, currents corresponding to these redox species (i.e., non-specific adsorption) may be recorded unless additional efforts are made to screen off these non-specific interactions, e.g., putting a diluent layer onto the conductor electrode. The non-specific interactions can be reduced or eliminated by using a semiconductor electrode wherein the semiconductor has a the band gap that has a limited potential window, such that the semiconductor can only conduct current for the electrochemical reaction occurring within that limited window. For example, the limited window can be between −1.0 to 0 V. Thus, in some embodiments, non-specific interactions in the solution can be reduced or eliminated by using a semiconductor electrode of the invention with the appropriate dopant density (which can be estimated using the Mott-Schottky equation).

One useful aspect of the semiconductors of the invention is that their conductivity can be modified by introducing impurities (dopants) into their crystalline lattice or amorphous regions. The process of adding controlled impurities to a semiconductor can be referred to as doping. The amount of impurity, or dopant, added to an intrinsic (pure) semiconductor alters its level of conductivity. Doped semiconductors may be referred to as extrinsic. The semiconductors of the present invention can be either intrinsic or extrinsic semiconductors.

Suitable dopants can be chosen, as is known in the art, on the atomic properties of the dopant and the material to be doped. In general, dopants that produce the desired controlled changes are classified as either electron acceptors or donors. A donor atom that activates (e.g., becomes incorporated into the crystal lattice) donates weakly-bound valence electrons to the material, creating excess negative charge carriers. These weakly-bound electrons can move about in the semiconductor relatively freely and thus can facilitate electrical conduction in the presence of an electric field. In some cases, the donor atoms introduce some states below, but very close to, the conduction band edge. Electrons at these states can be thermally excited to conduction band, becoming free electrons, in some cases, at room temperature. In some embodiments an activated acceptor dopant is utilized. The activated acceptor can produce a hole. Semiconductors doped with donor impurities are typically called N-type, while those doped with acceptor impurities are typically known as P-type. In some embodiments of the invention, the semiconductor of the invention can have both donor and acceptor dopants. In some embodiments the semiconductor can have both n type and p type charge carriers. The n or p type designation generally indicates which charge carrier acts as the material's majority carrier. The opposite carrier is generally called the minority carrier, which, in some cases, exists due to thermal excitation at a lower concentration than the majority carrier.

As described herein, where the semiconductor is a Group IV semiconductor such as silicon or germanium, suitable electron donors include, for example, phosphorous, arsenic, antimony, and bismuth. In some embodiments the dopant is phosphorous. In some embodiments the dopant is antimony. Where the semiconductor is a Group IV semiconductor such as silicon or germanium, suitable electron acceptors include boron, aluminum, gallium, and the like. In some embodiments, the dopant is boron. Where the semiconductor comprises an element in another group than Group IV, as is known in the art, elements that are outside of that group can act as either n type of p type dopants.

In addition to modification through doping, the resistance of semiconductors can in some cases, for example, be modified dynamically by applying electric fields. The ability to control resistance/conductivity in semiconductor substrate or within regions of semiconductor substrate dynamically through the application of electric fields can be useful in some embodiments.

The semiconductor substrate can be in any form that is amenable to the production of a semiconductor electrode. The semiconductor substrate can comprise a monolithic piece of the semiconductor, a coating of the semiconductor deposited onto another material, or a powder of semiconductor particles. The semiconductor substrate can be a monolithic form such as a chip, wafer, rod, needle, block, ingot, or the like. The semiconductor substrate can alternately be in particulate form, for example in the form of powder comprised of particles. The particles can be of arbitrary shape or can be in the form of fibers, sheets, beads, discs, or balls. Where the substrate is in the form of a powder made up of particles, it will generally be formed into a composite electrode as described in more detail below.

The semiconductor substrate of the present invention can be a thin layer of semiconductor that is formed upon another material, for example a thin layer of semiconductor formed on glass would constitute a semiconductor substrate.

In an embodiment, the semiconductor substrate can include a layer of semiconductor material having a thickness of about 0.1 nanometers ("nm") and 5000 nm, or between about 1 nm and 1000 nm, or between about 10 nm and 500 nm. In another embodiment, the semiconductor substrate can include a layer of silicon having a thickness of about 0.1 nanometers ("nm") and 5000 nm, or between about 1 nm and 1000 nm, or between about 10 nm and 500 nm.

In some embodiments the semiconductor substrate used to make the electrode is a composite material comprising semiconductor particles dispersed in a matrix or binder. The semiconductor substrate can be made of a composite material comprising a powder of semiconductor dispersed in a binder to make a composite semiconductor substrate. The semiconductor powder can be in the form of spheres, crystallites, rods, fibers, or any other arbitrary shape. In an embodiment the composite electrode is made of semiconductor crystallites dispersed in a polymeric matrix. The matrix or binder can be an organic, inorganic, or organometallic polymer. Non-limiting examples of useful inorganic polymeric materials include polyphosphazenes, polysilanes, polysiloxane, polygermanes, polymeric sulfur, polymeric selenium, silicones, and mixtures of any of the foregoing.

In some embodiments the polymer can be an organic polymer. Non-limiting examples of suitable organic polymeric materials include, but are not limited to, thermoset materials and thermoplastic materials. Non-limiting examples of polymers useful in the invention include polyesters such as polyethylene terephthalate, polybutylene terephthalate, and polyethylene naphthalate, polycarbonates, polyolefins such as polyethylene, polypropylene, and polyisobutene, acrylic polymers such as copolymers of styrene and an acrylic acid monomer, and polymers containing methacrylate, polyamides, thermoplastic polyurethanes, vinyl polymers, polyimides, polyamides, polytetrafluoroethelene and other fluoropolymers, and mixtures of any of the foregoing.

The binder can be insulating, semiconductive, or conductive. In an embodiment, the binder is a material, such as a polymer, which is an insulating material. Where an insulating binder is used, the current will tend to only flow through the dispersed semiconductor powder. In some embodiments, the binder includes conductive components. In some embodiments, the binder comprises a conductive polymer such as polyaniline, polyacetylene, poly(alkylthiophene), poly(alkylpyrrole), and the like. In some embodiments, the conductive component can comprise conductive particles such as metal particles, such as nickel particles other conductive particles including carbon particles. In some embodiments, the conductive component is chosen such that the conductive component such as the conductive polymer exhibits reduction and/or oxidation potentials that are outside of the reduction and/or oxidation potentials of the redox active moieties.

The composite semiconductor substrate can be formed by mixing the semiconductor powder with a monomer, oligomer, or prepolymer and curing the monomer, oligomer or prepolymer to form a polymeric matrix. The polymerization can be initiated in any manner known in the art or disclosed herein. The polymerization can be initiated, for example, thermally or photochemically in the presence of an initiator. The polymerization can be carried out with one or more crosslinkers. The cross-linkers can be chosen to adjust the physical properties of the polymeric matrix and thus adjust the properties of the composite semiconductor substrate. The composite semiconductor substrate can be formed by mixing the semiconductor powder with a molten thermoplastic polymer, forming the substrate, and allowing the mixture to cool. The composite semiconductor substrate can be formed by mixing the semiconductor powder with a polymer or prepolymer in a solvent, and allowing the solvent to evaporate to form the composite. Combinations of any of the above methods can be used.

The electrical properties of the composite semiconductor substrate can be affected by the amount of semiconductor, the particle size, and the particle shape. In general, the amount of semiconductor in the composite is high enough to create conductive pathways throughout the material. This amount of material necessary to provide conductive paths across the material is sometimes called the percolation threshold. The amount of semiconductor particles for conductivity can also depend on the processing conditions such as the viscosity of the binder and the amount of mixing. The amount of semiconductor is generally set at a level at which the physical properties of the material, such as mechanical strength and flexibility will not suffer to the point that the material is not useful. The amount of semiconductor will generally be from 0.1 volume percent to 70 volume percent of the composite material. In some embodiments the amount of semiconductor may be from 1 volume percent to 50 volume percent. In some embodiments the amount of semiconductor may be from 10 volume percent to 40 volume percent. The amount of semiconductor can be from 1% to 5%, 5% to 10%, 10% to 15%, 10% to 20%, 20% to 30%, 30% to 40%, 40% to 50% or 50% to 60%.

The composite semiconductor substrate can be formed by methods used for shaping polymeric materials such as coating, molding, and casting into shapes that are useful as electrodes. The composite semiconductor substrate electrode will generally be connected to an electrically conductive wire to apply current and potential. The material can be cast, coated, and/or molded onto a conductive substrate such as a metal to form a conductive junction for connecting conductors for transfer of current to and from the composite electrode.

The semiconductor substrates of the invention generally have a high enough electrically conductivity to act as electrodes, to transmit current for the oxidation and/or reduction of the bound redox-active moieties. To make the semiconductor substrate more conductive, the semiconductor substrate can include impurities or dopants to increase electrical conductivity and reduce the resistivity.

The electrical resistivity (reciprocal of conductivity) can be for example 0.1 (ohm-centimeters), 1 (ohm-centimeters), 10 (ohm-centimeters), 100 (ohm-centimeters), to in excess of 1000 or even 10,000 (ohm-centimeters) or even higher which is comparable to graphite and conventional metallic conductors.

In some embodiments the resistivity of the semiconductor substrate is the range of 0.0001 to 100,000 $\Omega$-cm (or ohm-centimeters). In some embodiments the resistivity of the semiconductor substrate is the range of 0.001 to 10,000 $\Omega$-cm. In some embodiments the resistivity of the semiconductor substrate is the range of 0.01 to 1000 $\Omega$-cm. In some embodiments the resistivity of the semiconductor substrate is the range of 0.1 to 100 $\Omega$-cm. In some embodiments the resistivity of the semiconductor substrate is within the range of 1 to 100 $\Omega$-cm. In some embodiments the resistivity of the semiconductor substrate is within the range of 10 to 90 $\Omega$-cm. In some embodiments the semiconductor substrate is single crystal semiconductor is Si(100) that is P-type with a resistivity of 10 to 90 $\Omega$-cm. In some cases several semiconductor substrates with different resistivities may be used. For example, a system of the invention may comprise one lightly doped semiconductor substrate having one redox active species bound to it, and also a more highly doped semiconductor surface having another redox active species bound to it. For example, a system of the invention may comprise one lightly doped semiconductor surface having a pH sensitive redox active moiety such as anthraquinone bound thereto, and a second semiconductor surface that is more highly doped having a hydrogen ion insensitive redox active moiety such as ferrocene bound to it.

In some cases different regions of the semiconductor substrate can be doped at different levels. For example, it is well known in the semiconductor processing art that a mask can be used to cover some regions of the semiconductor, while leaving other regions exposed. The exposed regions can be treated selectively with dopants resulting in a semiconductor surface wherein some regions are doped differently than other regions. By using multiple steps with various masks, the conductivity properties of different regions of the semiconductor surface can be controlled. Thus, some regions can have high conductivity, some low, some regions can have a large band gap, and other regions can have small band gaps, some regions can have N-doping, some P-doping, and some no doping. In addition, the various regions can be connected with conducting regions, for example deposited metal, e.g., gold in to be able to electrically address the various regions.

Silicon Substrates

Another aspect of the invention provides an electrochemical sensor having a semiconductor substrate that includes silicon. The silicon substrate can have a surface onto which are attached redox-active moieties. The silicon substrate can comprise amorphous silicon or silicon comprising a variety of crystalline forms. The silicon substrate can also be polycrystalline. In some embodiments the silicon substrate can have both amorphous and crystalline regions. In some embodiments, the silicon can be nanocrystalline or microcrystalline silicon. Nanocrystalline silicon and microcrystalline silicon can be used to describe an allotropic form of silicon with paracrystalline structure having small grains of crystalline silicon within the amorphous phase. Where the silicon substrate is crystalline, the surface of the silicon substrate can have various crystalline faces on the surface. Crystalline silicon is generally in a face centered cubic (fcc) form. In some embodiments, such as where a polycrystalline silicon is used, the surface may have multiple crystalline planes exposed. Where single crystal silicon is used, in some cases, the silicon substrate can be made to have one or more crystal planes represented or predominantly represented on the surface. In some embodiments, the surface of the silicon substrate will comprise one or more crystal planes having a crystalline lattice of (xxx) wherein x is an integer corresponding to the lattice defining the crystal plane. In some embodiments the crystal planes (100), (010), (001), (110), (101), or (112) may be predominantly represented at the surface. In some embodiments a silicon substrate has the (100) plane predominantly represented at the surface.

The silicon electrode of the present invention can comprise a polished or an unpolished silicon substrate. Silicon is generally polished prior to silicon processing, for example, building features such as transistors. In some embodiments, such as those embodiments where electronic functionality is incorporated into a silicon sensor, a polished silicon surface may be desirable. In other embodiments, an unpolished silicon substrate can be used. An unpolished silicon substrate can be less expensive than a silicon substrate that has gone through a polishing step. In addition, an unpolished silicon substrate can have a higher surface area for a given area of silicon than a polished silicon substrate.

The silicon electrode of the present invention can comprise porous silicon. An advantage of porous silicon is an increase of the effective surface area. An increased surface area can be advantageous for providing a higher signal from the oxidation and reduction of the surface bound redox moieties due to a higher number of such moieties in contact with the sample. As is known in the art, if the surface is too porous, it can become less robust. Therefore the level of porosity can be controlled to maximize important properties for the particular applications. The porous silicon can be prepared by, for example, galvanostatic, chemical, or photochemical etches from silicon wafers. In some embodiments, chemical etching with hydrofluoric acid (HF) can be used to produce a porous silicon substrate. In some embodiments, the average pore size of the silicon substrate ranges from 1 nm to 500 nm. Pore size can be measured by, for example, nitrogen gas adsorption or Hg porosimetry. In some embodiments, the amount of porosity ranges between 1% and 98%. In some embodiments, the amount of porosity ranges between 5% and 75%. In some embodiments, the amount of porosity ranges between 10% and 50%. In some embodiments, the amount of porosity ranges between 20% and 40%. In some embodiments the porosity is between 1% to 5%, 5% to 10%, 10% to 30%, 20% to 40%, 30% to 50%, or 40% to 60%. The porosity measurement can be made on an area percent basis or a volume percent basis.

In addition, porous silicon could be readily integrated with existing silicon-based integrated circuit (IC) manufacturing processes.

The silicon substrate can be in any form that is amenable to the production of a silicon electrode. The silicon substrate can comprise a monolithic piece of silicon, a coating of silicon deposited onto another material, or a powder of silicon particles. The silicon substrate can be a monolithic form such as a chip, wafer, rod, needle, block, ingot, or the like. The silicon substrate can alternately be in particulate form, for example in the form of powder comprised of particles. The particles can be of arbitrary shape or can be in the form of fibers, sheets, beads, discs, polyhedra, or balls. Where the substrate is in the form of a powder made up of particles, it will generally be formed into a composite electrode as described in more detail below.

In some embodiments the semiconductor electrode is made from single crystal silicon. The single crystal silicon can be made by zone melting, also called zone refining, a process in which rods of metallurgical grade silicon are first heated to melt at one end. Then, the heater is typically slowly moved down the length of the rod, keeping a small length of the rod molten as the silicon cools and re-solidifies behind it. Since most impurities tend to remain in the molten region rather than re-solidify, when the process is complete, most of the impurities in the rod will typically have been moved into the end that was the last to be melted. This end is then cut off and discarded, and the process repeated if a still higher purity is desired. The single crystal silicon of the invention can also be produced via the Czochralski process, (CZ—Si) which tends to be inexpensive and is capable of producing large size crystals.

In some embodiments the silicon electrode is polycrystalline. As used herein, the term "polysilicon" is used interchangeably with the term "polycrystalline silicon". In some embodiments, the polysilicon is deposited. The polycrystalline silicon can be deposited by low pressure chemical vapor deposition (LPCVD), plasma-enhanced chemical vapor deposition (PECVD), or solid-phase crystallization (SPC) of amorphous silicon in certain processing regimes These processes can require relatively high temperatures, for example, above 300° C. The polycrystalline silicon electrodes can also be made, for example on polymeric substrates, using laser crystallization to crystallize a precursor amorphous silicon (a-Si) material on a plastic substrate without melting or damaging the plastic. In some cases, the for example, short, high-intensity ultraviolet laser pulses are used to heat the deposited a-Si material to above the melting point of silicon, without melting the entire substrate. By controlling the temperature gradients, the crystal size on the electrodes can be controlled. Grain sizes can be, for instance from 10 nanometer to 1 micrometer. Another method to produce polysilicon at low temperatures for the electrodes of the present invention is a metal-induced crystallization in which an amorphous silicon thin film is crystallized, for example at temperatures at or above 150° C., while in contact of a metal film such as aluminum, gold, or silver. The polycrystalline silicon electrodes can also be formed onto a metal structure such as a wire. For example, the end of a cylindrical wire can be coated with polysilicon, which can be derivatized with redox active species as described herein. The structure can be used as an electrode or portion of an electrode with silicon portion accessible to the medium containing the analyte, and the wire acting to connect the silicon electrode to the parts of the system providing voltage and allowing for the flow of current.

An advantage of polysilicon over amorphous silicon (a-Si) is that the mobility of the charge carriers can be orders of magnitude larger than in single crystal silicon and the material also can show greater stability under electric field and light-induced stress.

The silicon substrate of the present invention can be a thin layer of silicon that is formed upon another material, for example a thin layer of silicon formed on glass would constitute a silicon substrate.

In some embodiments the silicon substrate used to make the electrode is a composite material comprising silicon particles dispersed in a matrix or binder. The silicon substrate can be made of a composite material comprising a powder of silicon dispersed in a binder to make a composite silicon substrate. The silicon powder can be in the form of spheres, crystallites, rods, fibers, or any other arbitrary shape. In an embodiment the composite electrode is made of silicon crystallites dispersed in a polymeric matrix. The matrix or binder can be an organic, inorganic, or organometallic polymer. Non-limiting examples of useful inorganic polymeric materials include polyphosphazenes, polysilanes, polysiloxane, polygermanes, polymeric sulfur, polymeric selenium, silicones, and mixtures of any of the foregoing.

In some embodiments the polymer can be an organic polymer. Non-limiting examples of suitable organic polymeric materials include, but are not limited to, thermoset materials and thermoplastic materials. Non-limiting examples of polymers useful in the invention include polyesters such as polyethylene terephthalate, polybutylene terephthalate, and polyethylene naphthalate, polycarbonates, polyolefins such as polyethylene, polypropylene, and polyisobutene, acrylic polymers such as copolymers of styrene and an acrylic acid monomer, and polymers containing methacrylate, polyamides, thermoplastic polyurethanes, vinyl polymers, polyimides, polyamides, polytetrafluoroethelene and other fluoropolymers, and mixtures of any of the foregoing.

The binder can be insulating, semiconductive, or conductive. In an embodiment, the binder is a material, such as a polymer, that is an insulating material. Where an insulating binder is used, the current will tend to only flow through the dispersed silicon powder. In some embodiments, the binder includes conductive components. In some embodiments, the binder comprises a conductive polymer such as polyaniline, polyacetylene, poly(alkylthiophene), poly(alkylpyrrole), and the like. In some embodiments, the conductive component can comprise conductive particles such as metal particles, such as nickel particles other conductive particles including carbon particles. In some embodiments, the conductive component is chosen such that the conductive component such as the conductive polymer exhibits reduction and/or oxidation potentials that are outside of the reduction and/or oxidation potentials of the redox active moieties.

The composite silicon substrate can be formed by mixing the silicon powder with a monomer, oligomer, or prepolymer and curing the monomer, oligomer or prepolymer to form a polymeric matrix. The polymerization can be initiated in any manner known in the art or disclosed herein. The polymerization can be initiated, for example, thermally or photochemically in the presence of an initiator. The polymerization can be carried out with one or more crosslinkers. The crosslinkers can be chosen to adjust the physical properties of the polymeric matrix and thus adjust the properties of the composite silicon substrate. The composite silicon substrate can be formed by mixing the silicon powder with a molten thermoplastic polymer, forming the substrate, and allowing the mixture to cool. The composite silicon substrate can be formed by mixing the silicon powder with a polymer or prepolymer in a solvent, and allowing the solvent to evaporate to form the composite. Combinations of any of the above methods can be used.

The electrical properties of the composite silicon substrate can be affected by the amount of silicon, the particle size, and the particle shape. In general, the amount of silicon in the composite is high enough to create conductive pathways throughout the material. This amount of material necessary to provide conductive paths across the material is sometimes called the percolation threshold. The amount of silicon particles required for conduction can also depend on the processing conditions such as the viscosity of the binder and the amount of mixing. The amount of silicon is generally set at level at which the physical properties of the material, such as mechanical strength and flexibility will not suffer to the point that the material is not useful. The amount of silicon will generally be from 0.1 volume percent to 70 volume percent of the composite material. In some embodiments the amount of silicon may be from 1 volume percent to 50 volume percent. In some embodiments the amount of silicon may be from 10 volume percent to 40 volume percent. The amount of silicon can be from 1% to 5%, 5% to 10%, 10% to 15%, 10% to 20%, 20% to 30%, 30% to 40%, 40% to 50% or 50% to 60%.

The composite silicon substrate can be formed by methods used for shaping polymeric materials such as coating, molding, and casting into shapes that are useful as electrodes. The composite silicon substrate electrode will generally be connected to an electrically conductive wire to apply current and potential. The material can be cast, coated, and/or molded onto a conductive substrate such as a metal to form a conductive junction for connecting conductors for transfer of current to and from the composite electrode.

The silicon substrates of the invention generally have a high enough electrically conductivity to act as electrodes, and to transmit current for the oxidation and/or reduction of the bound redox-active moieties. To make the silicon substrate more conductive, the silicon substrate will generally include impurities or dopants to increase electrical conductivity. Where polycrystalline silicon is used, the polycrystalline silicon electrode can either be deposited as doped polycrystalline silicon (in situ doped) or can be deposited undoped and subsequently doped with an impurity dopant such as phosphorus or boron by ion implantation or a thermal diffusion process. Dopant impurities, such as phosphorus and boron, tend to diffuse much more rapidly along the grain boundaries than they do through the silicon itself.

The dopant for a type IV semiconductor such as silicon, can be, for example, either an electron donor or an electron acceptor. Suitable electron donors are phosphorous, arsenic, antimony, and bismuth. In some embodiments the dopant is phosphorous. In some embodiments the dopant is antimony. Suitable electron acceptors are boron, aluminum, gallium, and the like. In some embodiments, the dopant is boron. In some embodiments, electron acceptors can impart a chemical resistance to the silicon electrode.

Where the silicon substrate is a monolithic material such as a wafer, the dopant can be either distributed throughout the bulk of the silicon, or can be limited to the surface region of the silicon wafer. In some embodiments, for example where the silicon substrate comprises multiple zones with different redox active moieties, the dopant can be distributed such that isolated regions of the surface of the silicon substrate are conductive.

The dopant is generally present in an amount greater than 0.01 weight percent of the silicon, and generally in an excess of 0.1 percent of the silicon. Generally, the dopant is less than 3 weight percent of the silicon, and almost always less than 6 weight percent of the silicon. The presence of small amounts of the dopant can increase the electrical conductivity. The dopant may not be homogenously distributed throughout the silicon, and the local concentration may vary between different regions of the silicon material.

The electrical resistivity (reciprocal of conductivity) can be for example 0.1 (ohm-centimeters), 1 (ohm-centimeters), 10 (ohm-centimeters), 100 (ohm-centimeters), to in excess of 1000 or even 10,000 (ohm-centimeters) or even higher which is comparable to graphite and conventional metallic conductors.

In some embodiments the resistivity of the silicon substrate is the range of 0.0001 to 100,000 Ω-cm. In some embodiments the resistivity of the silicon substrate is the range of 0.001 to 10,000 Ω-cm. In some embodiments the resistivity of the silicon substrate is the range of 0.01 to 1000 Ω-cm. In some embodiments the resistivity of the silicon substrate is the range of 0.1 to 100 Ω-cm. In some embodiments the resistivity of the silicon substrate is within the range of 1 to 100 Ω-cm. In some embodiments the resistivity of the silicon substrate is within the range of 10 to 90 Ω-cm. In some embodiments the silicon substrate is single crystal silicon is Si(100) that is P-type with a resistivity of 10 to 90 Ω-cm. In some cases several silicon substrates with different resistivities may be used. For example, a system of the invention may comprise a one lightly doped silicon substrate having one redox active species bound to it, and also a more highly doped silicon surface having another redox active species bound to it. For example, a system of the invention may comprise one lightly doped silicon surface having a pH sensitive redox active moiety such as anthraquinone bound thereto, and a second silicon surface that is more highly doped having a hydrogen ion insensitive redox active moiety such as ferrocene bound to it.

In some cases different regions of the silicon substrate can be doped at different levels. For example, it is well known in the semiconductor processing art that a mask can be used to cover some regions of the silicon, while leaving other regions exposed. The exposed regions can be treated selectively with dopants resulting in a silicon surface wherein some regions are doped differently than other regions. By using multiple steps with various masks, the conductivity properties of different regions of the silicon surface can be controlled. Thus, some regions can have high conductivity, some low, some regions can have a large band gap, and other regions can have small band gaps, some regions can have N-doping, some P-doping, and some no doping. In addition, the various regions can be connected with conducting regions, for example deposited metal, e.g., gold to be able to electrically address the various regions.

In some embodiments, Nisil is used. Nisil is an alloy of nickel and silicon. In some embodiments Nisil with 4%-5% silicon is used. In some embodiments Nisil with 4.4% silicon is used. In some embodiments Nicrosil is used. Nicrosil is a nickel alloy. In some cases Nicrosil comprising 14.4% chromium, 1.4% silicon, and 0.1% magnesium is used.

In some cases, for example, where the silicon substrate is cast silicon, the silicon substrate will include, for example, a silicide of a transition metal to provide castability. The silicide of the transition metal can provide favorable mechanical properties to the cast alloy. Typical metals useful in providing the transition metal silicide present in the silicon electrode of the secondary cell of this invention include titanium, zirconium, hafnium, vanadium, columbium, chromium, molybdenum, tungsten, manganese, iron, cobalt, nickel, copper, ruthenium, rhodium, palladium, osmium, iridium, platinum, gold, and silver. Most commonly, the transition metal present as the silicide in the silicon alloy may be a silicide of manganese, chromium, iron, cobalt, nickel, or molybdenum. The amount of the silicide may be sufficient to provide satisfactory castability but not great enough to deleteriously effect the properties of the silicon, i.e., from 2 percent or more up to as high as 30 percent transition metal, elemental basis.

Redox-Active Moieties

In some embodiments, an electrochemical sensor comprises a solid state (e.g., semiconductor) surface that is modified with redox-active functional groups. At least one redox-active functional group on the surface is sensitive to the presence and or the level of a substance in the solution. In some embodiments, the semiconductor surface can have at least one redox-active functional group sensitive to an analyte, and at least one redox-active functional group that is substantially insensitive to the analyte to be tested. When used in this manner, the substantially insensitive group can act as a reference, allowing for greater accuracy and reproducibility of the measurements.

In some situations, an electrochemical sensor can include a layer of a nitride, such as silicon nitride, having immobilized thereon a redox-active moiety that is sensitive to the presence of an analyte, such as H+, and/or a redox-active moiety that is insensitive to the presence of the analyte.

In some situations, redox active moieties that are sensitive and/or insensitive to the presence or absence of an analyte are bound to a surface of a solid state working electrode, such as a semiconductor (e.g., silicon) surface, through a surface-to-carbon interaction, such as, e.g., a silicon-to-carbon bond in cases in which the working electrode is formed of silicon. The silicon-to-carbon interaction can be a covalent interaction. The carbon atom in such a case is a carbon atom of a redox active moiety. In other situations, redox active moieties can be bound to a surface of a working electrode through surface-to-oxygen, surface-to-sulfur, and/or surface-to-carbon interactions, which can be covalent interactions.

The redox groups can be chemically or physically bound to the surface. The redox groups can be attached to the semiconductor covalently (e.g., via Si—C, Si—O, or Si—S bonds), can be adsorbed to the semiconductor, or can be attached to polymers that are either covalently or non-covalently bound to the surface. Covalent binding of either the redox group or the polymer to which the redox group is a part can be beneficial in improving the lifetime and stability of the electrode. Semiconductor materials such as silicon and germanium can form covalent bonds with carbon, and thus is a desirable substrate for functionalizing with carbon based molecules. The covalent binding to the surface can be through a bond between the semiconductor, e.g., silicon, and carbon, oxygen, nitrogen, sulfur, or other atom. In some embodiments the bond is between silicon and carbon. In some embodiments the bond is between silicon and oxygen. The physical bonding can occur through adsorption, and can include, for example, spontaneous self assembly onto the semiconductor surface of molecules such as those derived from fatty acids which comprise redox active moieties.

Where a linker group is used, the linker can be small, for example one to 3 atoms, or can be longer, e.g., 20 to 100 atoms, or can be any size between large and a small linker. Where a short linker is used, the redox-active moiety is held close to the surface. Where a longer group is used, the redox active moiety may be able to move away from the surface, for example into the solution. Linker groups can comprise hydrophilic, hydrophobic groups, or mixtures thereof. Linker groups can comprise, for example, hydrocarbons, esters, ethers, amides, amines, carbonyls, thiols, olefins, silicones, or other organic, inorganic or organometallic groups. The linker groups can be formed by polymerization or oligomerization reactions such as free radical, cationic, or anionic polymerization. The linker group can comprise, for example, ethylene oxide, propylene oxide, vinyl ether, or acrylamide repeat units. Linkers can have ring structures including aromatic rings. The variation in the linker structure can be used to vary the mobility of the redox-active moiety in the solution.

As used herein, the term moiety generally refers to a portion of a molecule or substituent. A redox-active moiety may be highly substituted, and can still act as a redox-active moiety. As used herein, the terms "redox active moiety", "redox active group", "redox active functional group", and "redox group" are used interchangeably. Thus, for example, the redox-active moiety ferrocene includes substituted ferrocenes, ferrocene polymers, and ferrocene covalently attached to the surface with or without linker molecules.

In some embodiments, the redox-active moiety can be incorporated into a polymer, and the polymer comprising the redox active moiety can be immobilized onto the semiconductor surface. The immobilization of the polymer can be either chemical or physical. The immobilization of the polymer can be through covalent bonds, or through adsorption of the polymer to the semiconductor surface.

In some embodiments, the redox-active moiety is bound to a particle that is bound to semiconductor. The particle is generally an electrically conductive particle. The particle attached to the semiconductor surface in a manner that allow for current to flow between the semiconductor surface and the particle. The particles can be attached chemically or physically to the surface. For example, the redox-active moiety can be attached to a carbon particle, and the carbon particle attached to the semiconductor surface. In some embodiments, the carbon particle can be a carbon nanotube. In some embodiments of the invention, carbon nanotubes can be attached to the surface of the semiconductor, where there are redox-active groups attached to the carbon nanotubes. For instance, attachment of well-aligned single-walled carbon nanotubes architecture to a single-crystal silicon surface can be used. In some embodiments, for example, ferrocenemethanol molecules are attached to single walled carbon nanotube (SWCNT) arrays that are directly anchored to the silicon surface, for example, a (100) surface. For example, single wall carbon nanotubes can be coupled to the surface using this method as described in Yu et al., Electrochimica Acta 52 (2007) 6206-6211.

The redox-active moieties generally have reversible redox activity with well-defined cyclic voltammetry oxidation and/or reduction peaks. A suitable reference redox reagent can vary from application to application or medium to medium depending on the intended use.

The position of the reduction and/or oxidation potentials of the redox active moiety can be chosen to improve the accuracy and quality of the measurement of redox potential. In some cases, the reduction and or oxidation potential can be chosen to be away from other redox active species. The silicon surface, for example, generally has a wide window in which to perform measurement of reduction or oxidation potential without interfering with the measurement of the reduction and or oxidation of the redox active moieties bound to the surface. The silicon surface can generally be used to measure oxidation and/or reduction potentials from between negative 2 V to positive 2 V. In some cases, for example where the medium is an aqueous medium, the reduction and/or oxidation potential of the redox-active moiety can be chosen so as not to fall within the reduction or oxidation potential of the medium to minimize interference. This can be useful where cyclic voltammetry is used, and is less important when square wave voltammetry is used.

Figure 5:
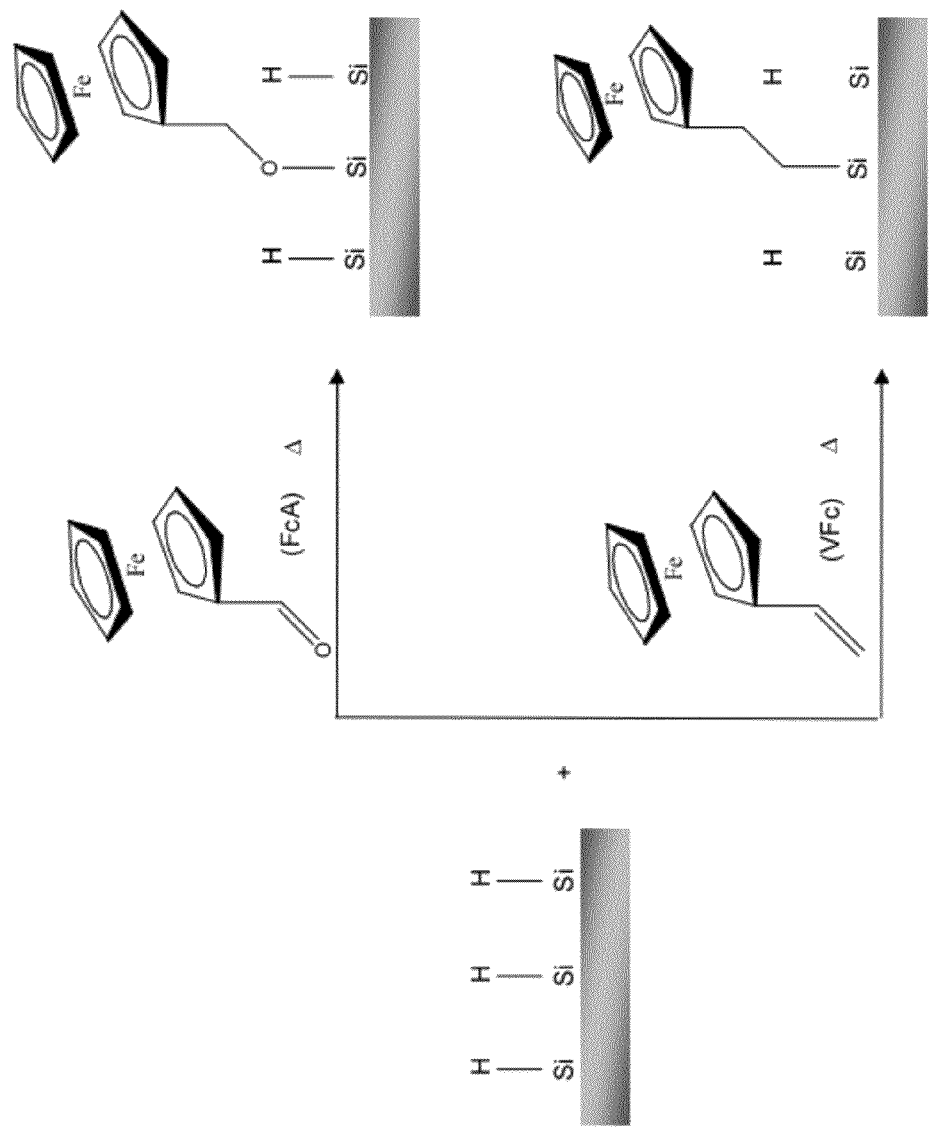
FIG. 5 illustrates a silicon surface derivatization with ferrocene moieties, vinyl-ferrocene (VFc) and ferrocene carboxaldehyde (FcA) by covalent attachment, in accordance with an embodiment of the invention.

Redox-active moieties that are insensitive to the presence of analytes should show little or no change in their oxidation and/or reduction potentials in the presence or absence of such analytes. Redox-active moieties that are generally insensitive to the presence of analytes, and in particular are insensitive to the presence of hydrogen ion include: ferrocene, polyvinylferrocene, $Os(bpy)_2Cl_2$, $Ru(bpy)_2Cl_2$, viologen, polyviologen, and polythiophene. Redox reagents having a high degree of electrochemical reversibility are generally preferred. FIG. 5 shows examples of the hydrogen ion insensitive redox-active moiety ferrocene bound to a silicon surface.

Figure 6:
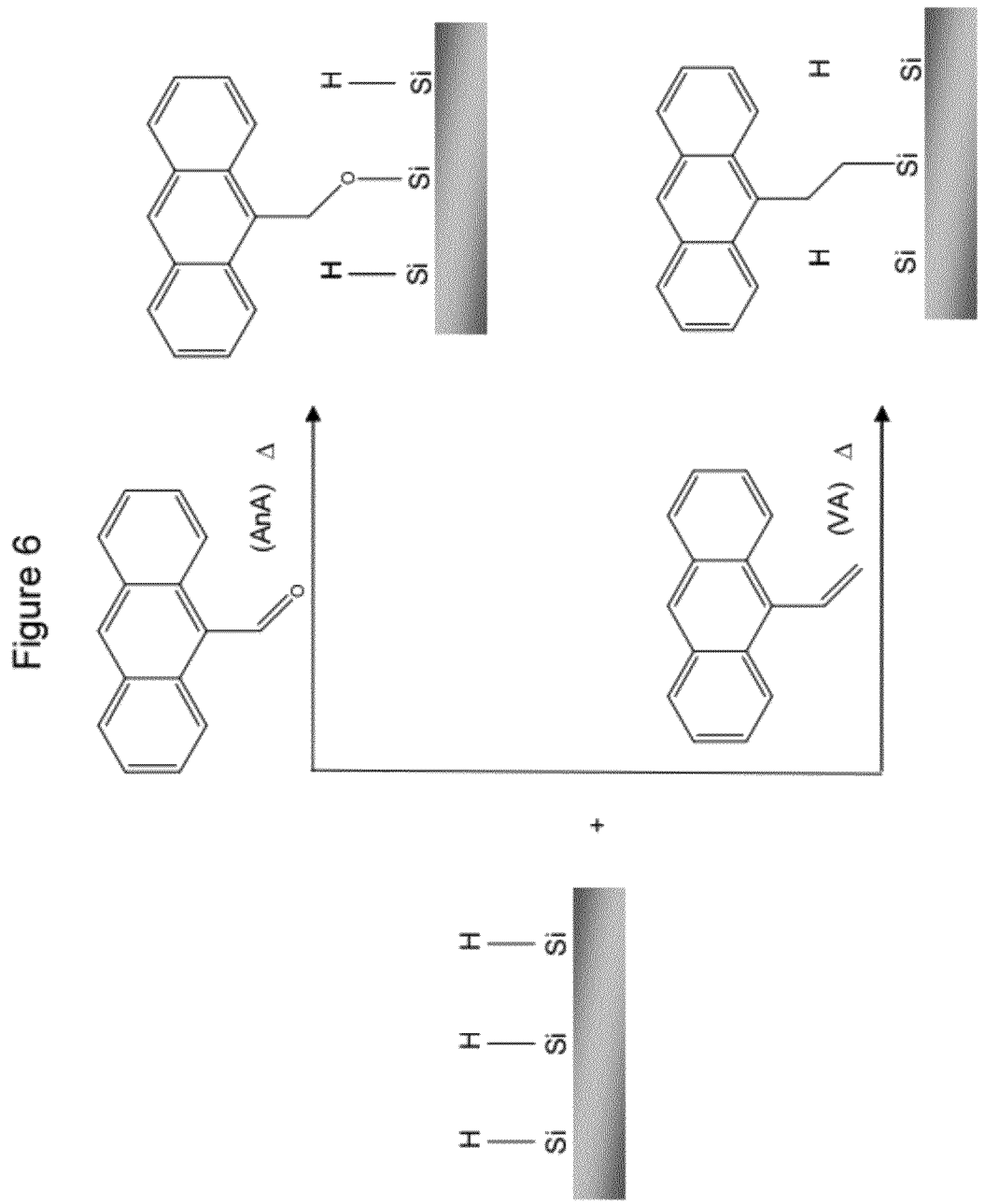
FIG. 6 illustrates a silicon surface derivatized with anthracene moieties, vinyl anthracene (VA) and anthraldehyde (AnA) by covalent attachment, in accordance with an embodiment of the invention.
Figure 7:
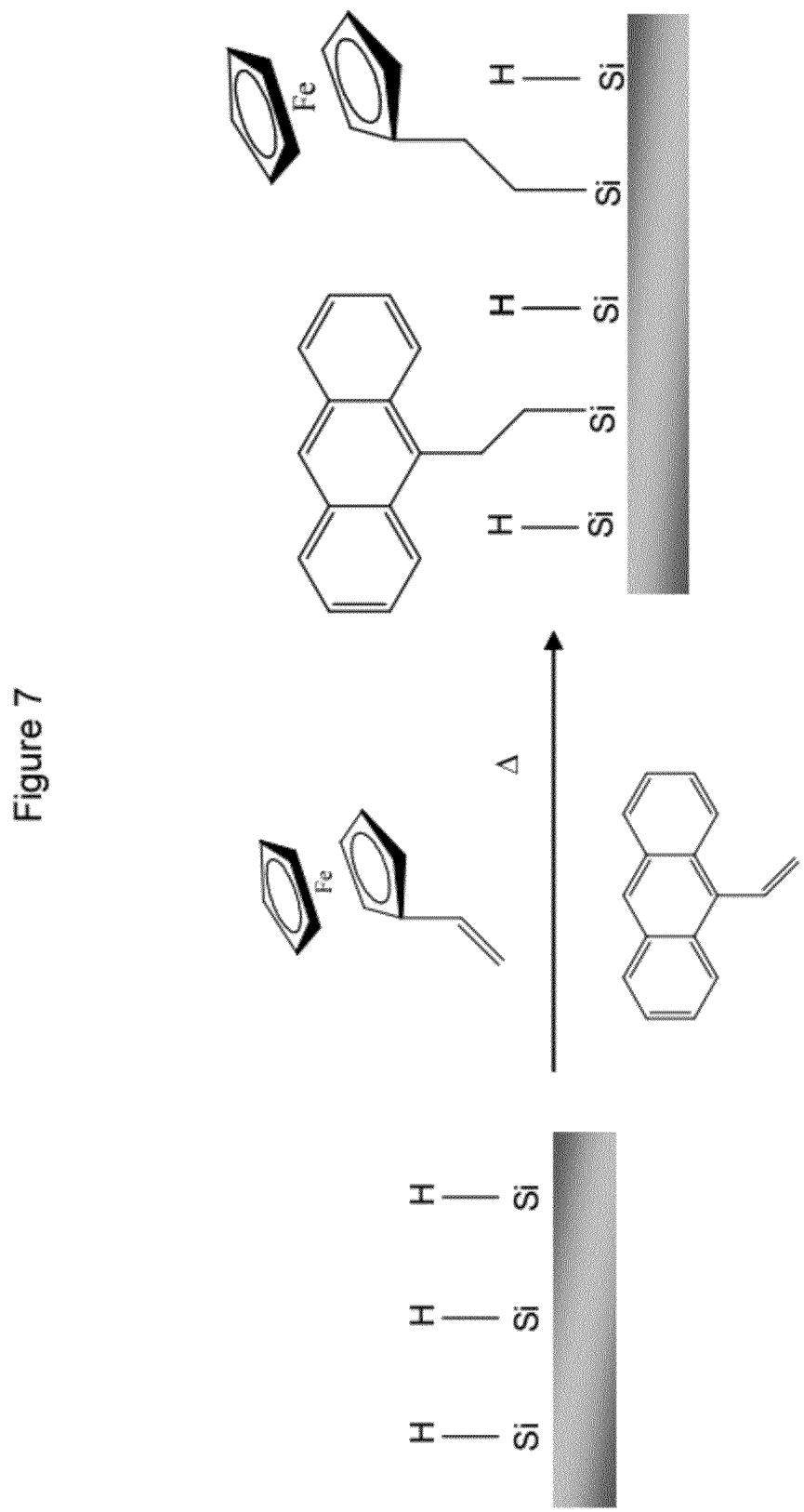
FIG. 7 illustrates a silicon surface derivatized with both the anthracene (VA) and ferrocene (VFc) moieties by covalent attachment, in accordance with an embodiment of the invention.

Non-limiting redox-active moieties that are sensitive to hydrogen ion include: quinones, anthroquinones, phenanthroquinones, phenylene diamines, catechols, phenothiazinium dyes, and monoquaternized N-alkyl-4,4'-bipyridinium. In some embodiments the redox-active moiety that is sensitive to the presence of hydrogen ion can include inorganic materials and metal oxides. Hydrogen ion sensitive inorganic redox-active inorganic moieties include Prussian Blue, $Ni(OH)_2$, and $RuO_x$. FIG. 6 shows examples of the hydrogen ion sensitive redox-active moiety anthracene covalently bound to a silicon surface. FIG. 7 shows an example of a silicon surface having covalently bound thereto both the hydrogen ion sensitive redox-active moiety ferrocene and the hydrogen ion insensitive redox-active agent anthracene.

In some embodiments the analyte is carbon monoxide (CO). An example of a CO sensitive redox-active agent is ferrocenyl ferrazetine disulfide or ferrazetine-ferrazetine disulfide. A CO insensitive redox-active agent can be, for example, ferrocene.

In some embodiments the analyte is an alkali metal. Alkali metal sensitive redox-active agents include, for example: 1,1'-(1,4,10,13-tetraoxa-7,16-diazacyclooctadecane-7,16-diyl dimethyl), ferrocenyl thiol, and other ferrocene derivatives containing covalently attached cryptands. These materials are described, for example, Hammond, et al., J. Chem. Soc. Perkin. Trans. 1707 (1983); Medina, et al., J. Chem. Soc. Chem. Commun. 290 (1991); Shu and Wrighton, J. Phys. Chem. 92, 5221 (1988). Included are examples such as the above ferrocenyl ferrazetine and ferrocenyl cryptand, in which an ordinarily chemically insensitive redox center (ferrocene) is covalently linked to a chemical recognition site in such a way as to make the redox center chemically sensitive. Also suitable are molecules or polymers in which the sensor and reference functionalities are covalently linked such as 1-hydro-1'-(6-(pyrrol-1-yl)hexyl)-4,4'-bipyridinium bis(hexafluorophosphate), as described by Shu and Wrighton, J. Phys. Chem. 92, 5221 (1988).

In some cases, more than one analyte-sensitive redox-active moiety can be used. For example, there can be one redox-active moiety that is sensitive to hydrogen ion, and another that is sensitive to a second analyte such as CO, oxygen, ammonia, or an alkali metal. This approach allows for the simultaneous measurement of several analytes. In some cases redox-active agents sensitive to 3 or more analytes can be used. Where there are redox agents sensitive to multiple analytes, in many cases, it is also desired to have one or more analyte-insensitive redox-active moieties bound to the semiconductor surface as well to provide a reference, to improve accuracy, and to minimize or avoid calibration.

Where more than one redox-active moiety is used it can be important to ensure there is not significant interference between the peaks. This can be desirable especially when the multiple redox-active moieties are on the same electrically addressable zone on the semiconductor substrate. This can be achieved, for example, by ensuring that there is sufficient separation of the oxidation and reduction potentials, or by physically separating the redox moieties.

In some embodiments, the semiconductor substrate has a plurality of isolated separately electrically addressable zones. In some embodiments, the different zones will comprise different redox-active moieties. The use of separate zones can be beneficial in that the voltammetric measurements can be carried out separately, allowing for the use of multiple redox-active agents with that have similar reduction and/or oxidation potentials.

The separately electrically addressable zones can be made by conventional semiconductor processing methods, for example masking to create structures in specific areas on the surface, for example specific areas on the surface having certain levels of doping. Conventional semiconductor processing can also be used to incorporate conductive interconnects allowing the zones to be separately addressable. Masking can also be used during the attachment of the redox-active moieties to the semiconductor surface to attach specific redox active moieties to different regions of the surface.

The semiconductor substrate with separately addressable zones can effectively create an electrochemical sensor array. Another aspect of the invention provides a semiconductor electrochemical sensor array wherein a plurality of zones, each zone comprising a redox active moiety. The array can have multiple zones with analyte-sensitive redox-active moieties, and one or more zones with analyte-insensitive redox active moieties. A zone can have a single redox-active moiety, or multiple redox active moieties. The array can be constructed, for example, to measure both pH and $O_2$, wherein one zone comprises a redox-active moiety sensitive to hydrogen ion, another zone has a redox active moiety sensitive to $O_2$, and a third zone with a redox-active moiety that is insensitive to both hydrogen ion and $O_2$.

In some embodiments, an array of separately addressable zones or an array of electrodes is used where there are a plurality of zones or electrodes that are each constructed to measure the same analyte and used in a redundant matter, wherein another zone capable of measuring the same analyte is used either simultaneously or in place of the other zone or electrode. In some cases, more than one zone or electrode, for example in an array, is used simultaneously to improve the quality of the measurement. In some cases, more than one zone or electrode, for example in an array, is used sequentially, wherein if one zone or electrode shows degraded performance, the measurement of that analyte is performed on another zone or electrode constructed to have similar characteristics. The sequential use of similar zones or electrodes can provide reliability of measurement over time. While the electrodes of the present invention can be prepared to be robust and to resist fouling, in some circumstances, degradation of the measurement over time may occur. In some embodiments, the maximum current ($I_{max}$) can be monitored over time. A system can be configured, for example, such that when the maximum current drops below a certain level, a switch is made to a redundant zone or electrode for further measurement of that analyte. There can be multiple redundant elements, e.g., 1, 2, 3, 4, 5, 10, 20 or more redundant elements.

The semiconductor substrate of the invention can also comprise circuitry. The circuitry can be used, for example for controlling the current and potential provide to the redox-active moiety. The circuitry can also be used for analyzing signals or for processing data related to the voltammetric measurement. The circuitry can also have other functionality, such as the ability to measure other parameters such as temperature, the ability to store date, or the ability to send data and receive instructions from a remote location. The circuitry can contain, for example, an amplifier such as an operational amplifier. The circuitry can contain, for example, an analog to digital converter (ADC). In some cases having the amplifying and ADC functions incorporated into the semiconductor substrate can provider higher quality and reliability of the transmission of the signal from the sensor. The use of circuitry on the semiconductor substrate can be particularly useful when an array of zones is utilized. The circuitry can assist in managing the passage of current in and out of the semiconductor substrate. In some cases, the circuits can allow for schemes to simultaneously or sequentially address the zones, for example, by mutiplexing (MUX).

Solid State Electrode Sensors

Another aspect of the invention provides a solid state sensor having a solid state working electrode formed of a solid state (e.g., semiconductor) substrate. The solid state electrode sensor comprising the solid state substrate can be used for the measurement of the presence or absence of one or more analytes, or can be used to accurately measure the concentration of analyte in a sample.

In some embodiments, a solid state electrode sensor is formed of a semiconductor, such as silicon. The semiconductor electrode sensor can be used to detect the presence or absence and/or the measure the concentration of analytes, including hydrogen ion, alkali metals, CO, or $O_2$. In some embodiments, the semiconductor electrode sensor is used to measure the concentration of hydrogen ion, or pH.

The semiconductor electrode sensor comprises a semiconductor substrate as described above comprising a redox-active moiety that is sensitive to the presence of an analyte. The semiconductor electrode sensor may also comprise a redox active moiety that is insensitive to the presence of an analyte. The semiconductor electrode sensor can comprise more than one semiconductor substrate. For example, the sensor may comprise one semiconductor substrate that has an analyte sensitive redox active moiety and another semiconductor substrate having an analyte insensitive redox active moiety.

The semiconductor electrode sensor is configured to be incorporated into a system that will supply voltage, and can drive current to the sensor to perform voltammetry. Thus, the semiconductor substrate or substrates within the sensor may be electrically connected in a manner which will allow for connection to a device for supplying and measuring current and voltage.

The semiconductor electrode sensor is generally the working electrode in an electrochemical system that will also comprise a counter electrode, and in some embodiments, a reference electrode.

The sensor may be put into contact with a sample having the analyte to be detected. The sample is generally a liquid sample. In some cases the sample can be a gel, suspension, molten, or semi-solid medium. The sample can be, for example, a foodstuff. The sample can be any type of liquid including hydrocarbons, oils, fluorocarbons, silicones, and aqueous solutions. Where the analyte is hydrogen ion, an aqueous medium is generally used, but in some case a polar protic medium or polar aprotic medium can be used. The sensor is useful for measuring pH in aqueous solutions.

In some embodiments, the sensor of the invention can accurately measure analyte concentrations where the analyte is present in a concentration range from $10^{-1}$ M to $10^{-14}$ M. In some embodiments, the sensor of the invention can accurately measure analyte concentrations where the analyte is present in a concentration range from $10^{-3}$ M to $10^{-10}$ M. In some embodiments, the sensor of the invention can measure the concentration to an accuracy of plus or minus 100%, 50%, 30%, 20%, 10%, 5%, 2% or 1%. In some embodiments, the sensor of the invention can measure the concentration within a range of $10^{-3}$ M to $10^{-10}$ M to an accuracy of plus or minus 100%, 50%, 30%, 20%, 10%, 5%, 2% or 1%.

In some embodiments, the analyte is hydrogen ion, and the sensor of the invention can accurately measure the pH in a range from pH 1 to pH 14. In some embodiments, the analyte is hydrogen ion, and the sensor of the invention can accurately measure the pH in a range from pH 3 to pH 10. In some embodiments, the sensor of the invention can accurately measure pH to an accuracy of plus or minus 0.5, 0.3, 0.2, 0.1, 0.07, 0.05, 0.03, 0.02, or 0.01 pH units. In some embodiments, the sensor of the invention can accurately measure pH in a range from pH 3 to pH 10 to an accuracy of plus or minus 0.5, 0.3, 0.2, 0.1, 0.07, 0.05, 0.03, 0.02, or 0.01 pH units.

The semiconductor electrode sensors of the invention can accurately measure analyte concentration in a wide variety of sample types. The sensors can be made to be robust, and resistant to fouling, and therefore reliable for long-term measurements.

Another aspect of the invention is a sensor which does not require routine calibration (or re-calibration), or in some cases any calibration at all. Conventional potentiometric sensors rely on a glass membrane to sense, for example, hydrogen ion. These types of sensors generally need to be calibrated on a regular basis, usually by placing the sensor into standards of known analyte concentration. These types of sensors generally need calibration when going from one solution to another solution, and will also need calibration with time, even if kept within the same solution and upon standing outside of a solution. The situation is made worse if there is a change in the composition of the medium over the time that the sensor is monitoring the medium, for example, when monitoring a chemical reaction, biochemical reaction, or fermentation. In these cases, potentiometric sensors may drift and need calibration due to the accumulation of some species in the reaction, or due to fouling of the sensor by species present.

In some embodiments, the sensors of the present invention do not need to be calibrated under any of these situations. In some embodiments, the sensors of the invention do not need to be calibrated over time in solution. In some embodiments, the sensors of the invention do not need to be calibrated after an hour, 10 hours, 1 day, 2 days, 5 days, a week, two weeks, a month, 6 months, 1 year, 2 years or longer while in a solution or in storage. In some embodiments the sensors or the present invention are accurate at measuring analyte concentration to 50%, 40%, 20%, 10%, 5%, 2%, 1%, 0.5%, 0.2% or 0.1% after the times above. In some embodiments where the sensors measure pH, the sensors are accurate to 1, 0.8, 0.5, 0.3, 0.2, 0.1, 0.08, 0.05, 0.03, 0.02, or 0.01 pH units after the times above. In some embodiments where the sensors measure pH, the sensors are accurate to within 0.1 pH units after one week in solution or in storage.

In some embodiments, the sensor is capable of measuring analyte concentration without any calibration with an external standard. In some embodiments, the sensor remains sensitive to the analyte without calibration after a first use by an end user.

In some embodiments the analyte is hydrogen ion and the sensor remains sensitive to hydrogen ion after exposure to a cell culture medium for at least 1, 3, 6, 9, 12, 18, or 24 hours or 2, 3, 4, 6, 8, 12, 24, 48, 60, 90, or more days. In some embodiments the analyte is hydrogen ion and the sensor remains sensitive to hydrogen ion after exposure to a cell culture medium for at least 3 days. In some embodiments the analyte is hydrogen ion and the sensor remains sensitive to hydrogen ion after exposure to a cell culture medium for at least 6 days. In some embodiments, the sensor is capable of measuring pH with an accuracy of 0.2 units after exposure to the cell culture medium.

In some embodiments, the analyte is hydrogen ion and the sensor is capable of measuring pH with an accuracy of 0.2 units after autoclave treatment at 121° C. for 10, 20, 40, 80, 100, 200, 400, or 800 minutes. In some embodiments, the analyte is hydrogen ion and the sensor is capable of measuring pH with an accuracy of 0.2 units after autoclave treatment at 121° C. for 40 minutes. In some embodiments, the analyte is hydrogen ion and the sensor is capable of measuring pH with an accuracy of 0.2 units after autoclave treatment at 121° C. for 400 minutes.

A subject sensor that does not require calibration over long periods of time in a medium that can change characteristics is useful, for example, as an implantable sensor. The implantable sensor can be placed under the skin or within the body in contact with a bodily fluid such as blood, saliva, breast milk, amniotic fluid, lymph, sweat, tears, or urine. The sensor can measure the concentration of analytes such as hydrogen ion, sodium, potassium, calcium, or oxygen.

The implantable sensor has an electrode configured to be in contact with a bodily fluid, said electrode comprising a semiconductor surface that has immobilized thereon a redox active moiety, wherein the redox active moiety has an oxidation potential and/or reduction potential that is sensitive to concentration of said ion. The implantable sensor can be included in an implantable medical device such as described in U.S. Pat. No. 6,738,670. For example, the implantable medical device in which the sensor resides could include pacemakers, defibrillators, drug delivery pumps, diagnostic recorders, cochlear implants, and the like. The implantable medical device is typically programmed with a therapy and then implanted in the body typically in a subcutaneous pocket at a site selected after considering clinician and patient preferences. In some embodiments the implanted device is in a form which can be swallowed, allowing the measurement of the properties of the regions encountered as it passes through the body such as the digestive tract including the stomach, the upper and lower intestines, and the colon. The information obtained by the sensor in the implanted device can either be accessed in real time, for example, by wireless communication, or can be retrieved from the device after passage through the body. A wide variety of programmers, also known as downlink transmitters, can be used to transmit data to and receive data from the implantable medical device. Examples of downlink transmitters include devices such as physician programmers, patient programmers, programming wands, telemetry access units, and the like. The clinician, for example, can periodically use a physician programmer to communicate with the implantable medical device to manage the patient's therapy and collect implantable medical device data. The semiconductor electrode sensor can be incorporated into or attached to the implantable medical device and can provide data on analyte concentration within the region of the body into which it is implanted. The patient can use the patient programmer to communicate with the implanted device to make therapy adjustments that have been programmed by the clinician. Both the physician programmer and patient programmer can have an antenna locator that indicates when a telemetry head is aligned closely enough with the implanted device for adequate telemetry.

Another aspect of the invention is a method for measuring concentration in a bodily fluid within a body, the method comprising placing a semiconductor electrode sensor comprising a redox active moiety in contact with the bodily fluid, and operating the sensor to yield a value of the concentration of the analyte present in said bodily fluid.

Systems for Measuring the Concentration and/or Presence or Absence of an Analyte Another aspect of the invention provides a system for measuring analyte concentration. In some embodiments, the system comprises a working electrode having a solid state (e.g., semiconductor) surface that has immobilized thereon a redox active moiety, wherein the redox active moiety has an oxidation potential and/or reduction potential that is sensitive to the presence of an analyte; a counter electrode and optionally a reference electrode. The system further comprises a source for supplying a plurality of potentials to the working electrode, and a device for measuring current through the working electrode at the plurality of potentials. The working electrode referred to herein can comprise the solid state electrochemical sensor described above. It is desirable in some embodiments that the solid state surface also has immobilized thereon a second redox active moiety having an oxidation potential and/or reduction potential that is insensitive to the presence of said analyte. The redox active moiety that is insensitive to the presence of the analyte can be on the same solid state surface, or can be on another solid state surface in electrical communication with the system and in contact with the sample. In some embodiments, the redox active moiety that is sensitive to the presence of the analyte is on first solid state (e.g., semiconductor) working electrode, and the redox active moiety that is insensitive to the presence of the analyte is on a second solid state working electrode that is electrically isolated (or electrically insulated) from the first working electrode. The system is configured such that the working electrode(s), the counter electrode, and optionally the reference electrode are in contact with the sample. In many embodiments, the sample is a liquid sample, and the electrodes are each in contact with the liquid. In some cases, the sample will not be a liquid, but may be a solid, generally comprising a solid electrolyte, a semi-solid (e.g., solid-liquid mixture), or a gas, or a sample having a viscosity characteristic of a gas or liquid. In some embodiments, the first solid state working electrode is separately and independently addressable from the second solid state working electrode, enabling a reading from the first working electrode independently from the second working electrode.

In some embodiments, the system will have two or more working electrodes. For example, in some embodiments, the system will have one working electrode comprising a semiconductor surface that has immobilized thereon a redox active moiety whose oxidation potential and/or reduction potential is sensitive to the presence of said analyte, and a second working electrode comprising redox active moiety whose oxidation potential and/or reduction potential is insensitive to the presence of said analyte. An example of a system with two working electrodes is a system having two semiconductor wafers or chips, one of which has a redox active moiety which is sensitive to pH, such as anthracene, and another redox active moiety which is insensitive to pH, such as a ferrocene. In some cases the semiconductor wafer or chip on which each redox active species is immobilized may be a different type of semiconductor wafer or chip. For instance, the semiconductor wafer or chip to which the pH sensitive moiety is bound may have one doping level, and the semiconductor wafer or chip on which the pH insensitive moiety is bound may have a different doping level. This type of construction can be beneficial because, in some cases, one type of redox active species will perform better in terms of amplitude, sensitivity or stability with one type of doping, while another redox active species will perform better on a semiconductor wafer or chip with a different type of doping. In some embodiments, the pH sensitive moiety, e.g., anthracene, is bound to a semiconductor wafer that has a low level of doping, and the pH insensitive moiety, e.g., ferrocene is bound to a silicon wafer that has a higher level of doping. In some embodiments the semiconductor wafer onto which the pH sensitive moiety, e.g., anthracene is bound has a resistivity between 1 $\Omega$-cm an 1000 $\Omega$-cm, or between 10 $\Omega$-cm and 90 $\Omega$-cm, or between 10 $\Omega$-cm and 40 $\Omega$-cm, while semiconductor wafer onto which the pH insensitive moiety, e.g., ferrocene, is bound has a resistivity between 1 milliohm-cm and 1000 $\Omega$-cm, or 1 $\Omega$-cm and 90 $\Omega$-cm, or 10 $\Omega$-cm and 40 $\Omega$-cm. In some embodiments, an N-type semiconductor (e.g., silicon wafer) is used for a working electrode having an H+ insensitive moiety (e.g., ferrocene). In some situations, an undoped or lightly doped p-type semiconductor (e.g., silicon wafer) is used for a working electrode having an H+ sensitive moiety (e.g., anthracene). In other embodiments, a P-type semiconductor (e.g., silicon wafer) may be used for both the pH sensitive and the pH insensitive moieties.

In some embodiments, the system will have 3 or more working electrodes. For example, in some embodiments, the system will have one working electrode comprising a semiconductor surface that has immobilized thereon a redox active moiety that is sensitive to the presence of a first analyte, a second working electrode comprising a semiconductor surface that has immobilized thereon a redox active moiety that is sensitive to the presence of a second analyte, and a third working electrode comprising a semiconductor surface that has immobilized thereon a redox active moiety that is insensitive to the presence of either the first analyte nor the second analyte. The system can also have more than 3 working electrodes, for example having 4, 5, 6, 7, 8, 9, 10, 12, 20, 50 or more working electrodes, each having redox active moieties sensitive to and analyte. These systems can also have one or more than one semiconductor working electrode having a redox species that is insensitive to the analytes, for example to provide a reference. In some cases more than one redox species that is insensitive to the analyte can be used.

Figure 21:
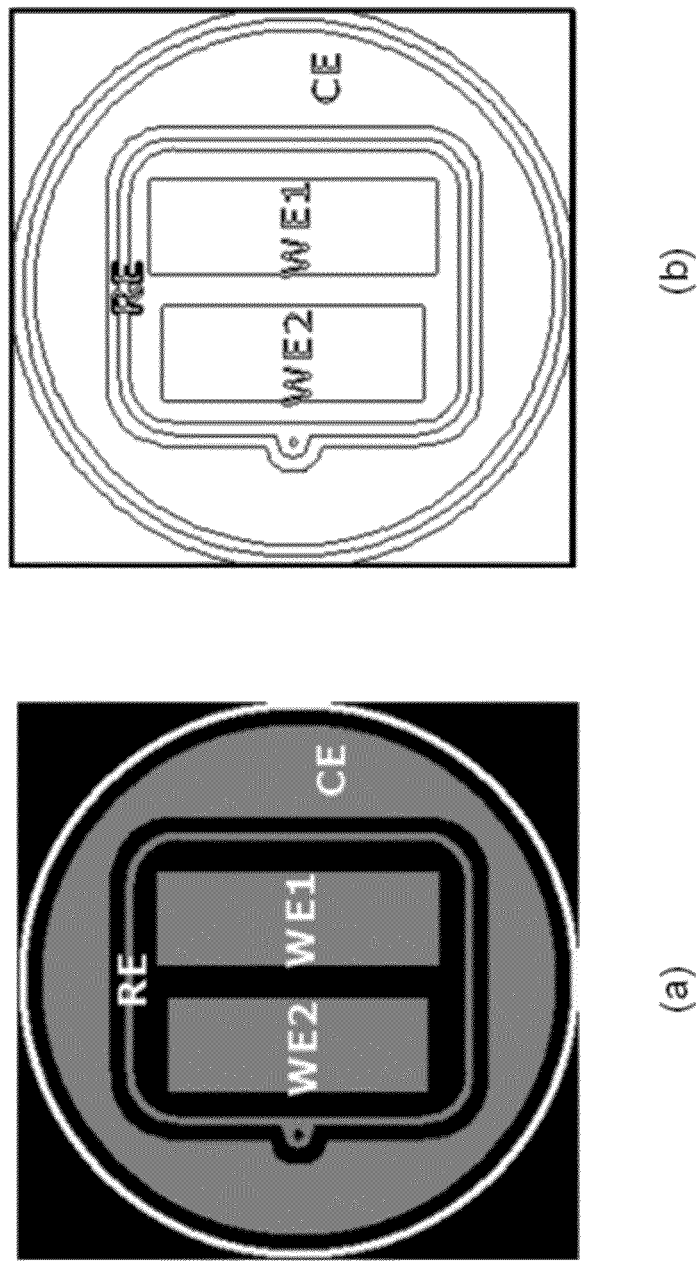
FIG. 21 depicts an exemplary embodiment of a probe of the present invention having a four electrode configuration with a ring reference electrode (RE) and a ring counter electrode (CE), in accordance with an embodiment of the invention.

In some embodiments the system of the present invention comprises a probe that comprises the 2 or more electrodes. The probe can physically hold the electrodes such that the electrodes can be brought into contact with the sample. The probe allows the working electrodes to be held close to the reference and/or counter electrode. FIG. 21 shows an exemplary embodiment of a probe of a system of the present invention having 4 electrodes: a first working electrode (WE1), a second working electrode (WE2), a reference electrode (RE), and a counter electrode (CE). WE1 and WE2 can each be formed of a solid state material, such as a semiconductor. FIG. 21(a) shows a shaded drawing of the probe. FIG. 21(b) shows a line drawing of the probe. As shown in FIG. 21, in some cases it can be beneficial in the present invention for the reference electrode and the counter electrode to have a ring configuration. In other embodiments, only one of the reference electrode or counter electrode will have a ring configuration. A ring electrode can in some cases provide signal stability. While this embodiment shows one configuration, there are other ring electrode configurations that can be used with the present invention.

In some embodiments it is useful to use undoped or lightly doped semiconductor (e.g., silicon) substrates for a moiety such as anthracene. While not being bound by theory, the band gap of the semiconductor, e.g., silicon can be influenced by the level of doping of the semiconductor, and it is believed that in some cases, the use of a semiconductor with the appropriate level of doping can be useful to tailor the appropriate redox active moiety with the appropriate band gap. Thus in some cases it is desirable to use lightly doped semiconductor, e.g., silicon with a moiety such as anthracene. Thus in some embodiments it is useful to use two semiconductor working electrodes: one optimized for ferrocene moieties and the other optimized for the anthracene moieties. When two working electrodes are used, in some embodiments, two sequential electrochemical measurements (e.g., with square wave voltammetry) may be carried out using the same counter and reference electrode. For instance, the first measurement can be conducted using reference, counter and working electrode 1 (e.g., anthracene derivatized) between −1.2 to −0.5 V, followed by the second measurement which may be conducted using reference, counter and working electrode 2 (e.g., ferrocene derivatized) between 0 to 0.5 V. The peaks potential detected in the first and second measurements can then be stored and processed to get a pH reading. This type of system and method can be accomplished through the use of a bipotentiostat or a two-channel multiplexer. A similar approach can be applied to multiple working electrodes with a mutipotentiostat or a multi-channel multiplexer.

The system is configured to carry out voltammetric measurements on the sample. Some embodiments provide a method which includes the measurement of pH with a voltammetric pH sensing system comprising the semiconductor electrode sensor described above, a potentiostat for providing voltage to the electrodes, and a meter for detecting the current as a function of voltage.

The counter electrode typically is needed to complete the electrochemical circuit to make the measurements described herein. The counter electrode is generally made of a material which is electrochemically inert to the medium so that current overloading does not occur during the course of measurement. Suitable materials in many applications include platinum, silver, gold, stainless steel, and carbon.

A reference electrode is optional and is used as a third electrode in some embodiments of the invention. In the case of a three-electrode system, the counter electrode generally completes the circuit, allowing current to flow through the cell, while the reference electrode maintains a constant interfacial potential difference regardless of the current. In the case where the system comprises an analyte sensitive redox active moiety and an analyte insensitive redox active moiety, the analyte insensitive redox active moiety can act as a reference, allowing the potential difference to be used to determine analyte concentration. Even where the system comprises an analyte insensitive moiety, in some embodiments, a reference electrode will still be used. In some embodiments, pseudo-reference electrodes can also be utilized. Reference electrodes that can be employed include: Standard hydrogen electrode (SHE), also known as "normal hydrogen electrode" (NHE), saturated calomel electrode (SCE), copper-copper(II) sulfate electrode, and silver/silver chloride (Ag/AgCl) electrode. In some embodiments a silver electrode or a polyurethane coated silver electrode can act as a silver/silver chloride electrode where sufficient chloride is present at or near the silver electrode. In some cases, e.g., in non-aqueous medium, a metal electrode such as a platinum or a silver electrode, or a polyurethane coated silver electrode can be used as the reference electrode.

To carry out voltammetry, the system generally has a source for supplying a plurality of potentials. The voltammetry can be, for example cyclic voltammetry, pulse voltammetry, normal pulse voltammetry, square wave voltammetry, differential pulse voltammetry, linear voltammetry, or square wave voltammetry. The source for supplying a plurality of potentials can be a potentiostat, for example, a potentiostat capable of applying square waves for square wave voltammetry.

Generally, the analyte concentration is determined by using voltammetry to identify the position of current peaks, which current peaks indicate the reduction or oxidation potential of a redox active moiety. In some embodiments, the position of the reduction and/or oxidation potential of the analyte sensitive redox active moiety is used to determine the concentration of the analyte. This method can be used, for example, where no analyte insensitive redox active moiety is employed.

Where an analyte insensitive redox active moiety is used, detection is generally accomplished by measuring the potential difference, delta E, associated with current peaks for oxidation (or reduction) of the immobilized redox active moieties, where the magnitude of delta E can be related to the concentration of analyte, e.g., hydrogen ion (H+) in solution. The analyte insensitive redox active moiety has an electrochemical response that is insensitive to variations in the medium and serves as the reference. Current peaks for oxidation or reduction of the reference and indicator are determined from a voltammogram using a counter electrode.

In some embodiments, the system further comprises a computation system that communicates with the device for measuring current. The computation system can have algorithms for calculating reduction or oxidation potential from the measured current at a plurality of potentials from the voltammetry measurements. The computing systems can be part of the sensing system, in some cases allowing the sensing system to be self-contained. The computing system can comprise memory for storing raw and/or processed data from the sensors. The computing system can be connected to a transmission device that will wirelessly, by wire, fiber or other means, transmit processed data to an external device. The computing system can provide signals and measurements which can be transmitted in some cases in real time, allowing the system to alert end users of conditions which may require attention. The transmitted signals and measurements can, for example, provide the information required for adjusting a manufacturing process such as a chemical or biochemical process.

In some embodiments the system is made up of a housing that holds the semiconductor electrode sensor that is electrically connected to a unit comprising the source for supplying a plurality of potentials and the current measuring device. In some embodiments the unit also comprises the computing system described above for at least partially analyzing the data. The unit can be self powered, e.g., with a battery, or can have a connection to an outside power source. The unit can have a display and input buttons to allow the user to control the measurement and to read the output from the sensor. The unit can have transmission capability for sending out data, and for receiving instructions or to be tested by an external device.

FIG. 1 shows drawings of an embodiment of the connection of a semiconductor sensor electrode into a sensor housing for use in measuring analytes in a fluid such as the fluid in a biochemical reactor. FIG. 1(a) shows a blow up drawing of an assembly that holds the semiconductor electrode sensor and provides electrical connections to the semiconductor electrode sensor for voltammetry measurements. In FIG. 1(a) the semiconductor electrode sensor (I), is held in place by the end cap (II), in contact with the metallized ceramic disk (III). The ceramic disk can be metallized in specific areas on both the front and the back of the disk, with vias connecting the specific metallized areas. On one side of the ceramic disk, the semiconductor working electrodes as well as the counter and optionally reference electrodes can be present. For example, electrodes such as the semiconductor working electrodes can each being mounted to a specific metallized area. The disk is then mounted into the housing such that the side of the disk having the electrodes is exposed to the medium into which the probe is immersed, and the other side of the disk is away from the medium, allowing for electrical connection to the metallized areas on the disk such that voltage can be applied and current can flow to and from the electrodes. The sealing gasket (IV) provides sealing from the fluid in which the sensor is immersed while allowing electrical contact with the pin contacts (V) on the shaft of the housing (VI). FIG. 1(b) shows the housing assembled for insertion into the fluid to be measured. Pipe fittings are used to seal the wires that provide electrical connection to the semiconductor electrode for voltammetric measurements.

FIG. 2 shows a drawing of an embodiment of the unit comprising the source for supplying a plurality of potentials and the current measuring device. FIG. 2(a) shows a top view and FIG. 2(b) shows a back side view. The unit has an electrical input/output connector for connecting to the electrodes for carrying out voltammetry. The unit has a connection for AC power. The unit has a universal serial bus interface (USB I/F) and an RS-232 Serial port for transmitting data, for receiving instructions, and for testing and debugging by an external device. The unit also comprises a liquid crystal display (LCD) and has user interface buttons to allow the user to control the measurements and to read the output from the sensor.

Figure 3:
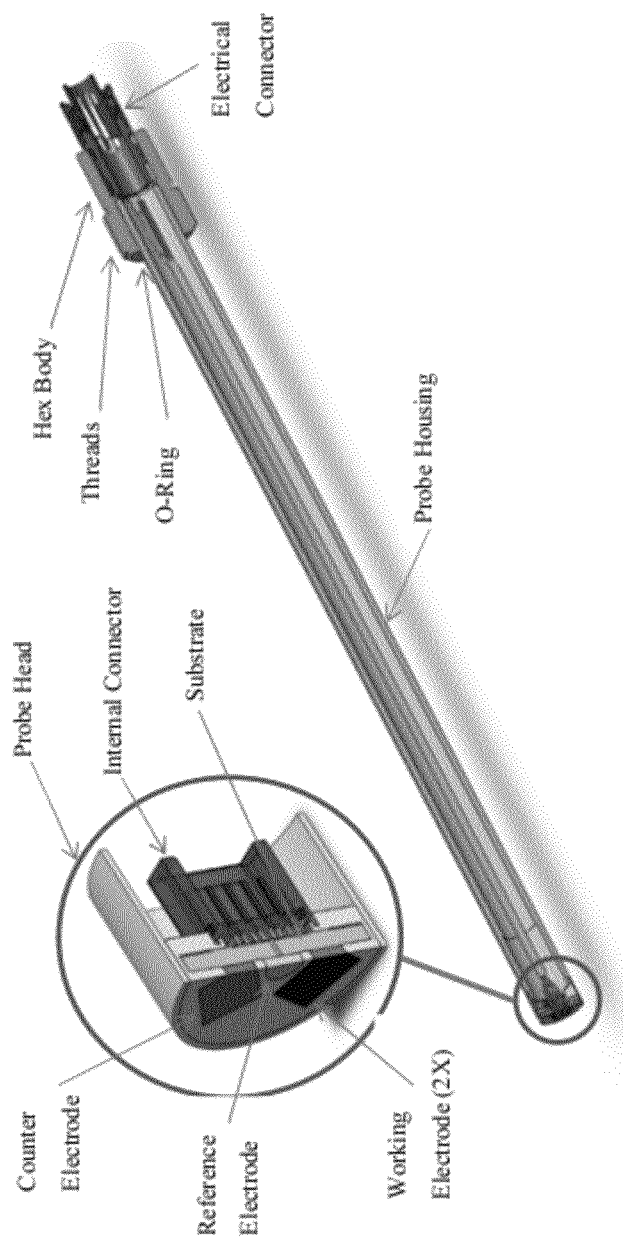
FIG. 3 depicts an embodiment of the invention comprising a probe for measuring analytes within a reactor comprising two working silicon electrodes, in accordance with an embodiment of the invention.

FIG. 3 shows another exemplary embodiment of a system, in accordance with an embodiment of the invention. FIG. 3 shows a probe that contains two semiconductor (silicon) working electrodes, a reference electrode, and a counter electrode. The electrodes can be electrically connected through the probe to the source for supplying a plurality of potentials to the working electrode, the counter electrode, and optionally the reference electrode, and a device for measuring current through the working electrode at the plurality of potentials. In this embodiment, the two working electrodes, the reference electrodes and the counter electrode are contained on the end of the probe on a disk which allows the electrodes to be in contact with the medium comprising the analyte(s) to be measured. The areas of the various electrodes can be varied to improve the performance of the system. While this embodiment shows two working electrodes, in some embodiments, there may be one working electrode, and in other embodiments, there are 3, 4, 5, 10, 20, or more working electrodes. In some embodiments one working electrode can comprise a semiconductor surface with a redox active moiety that is sensitive to pH, such as anthracene, and the other working electrode can comprise a redox active moiety that is insensitive to pH, such as ferrocene. In some embodiments, the semiconductor surface on which the pH sensitive moiety, such as anthracene, is bound comprises a silicon wafer that is lightly doped, and the silicon surface on which the pH insensitive moiety, such as ferrocene, is bound comprises a silicon wafer that is more heavily doped.

The semiconductor working electrodes can be bonded to conductive regions on the disk. Conductive vias through the disk allow electrical connection to electrode pins which are contained within the housing. The electrode pins are in turn, electrically connected, for example to wires, which can run through the probe housing, and then out of the housing to electrically connect the electrodes to the source for applying potentials to the electrode, and to the device for measuring the current that passes through the electrodes. The threads, o-ring, and hex body allow for the probe to be mounted into a reactor such as a bioreactor or fermentor. The threads allow for the probe to mate with a corresponding threaded hole through the wall of the reactor, the hex body allows for tightening the probe into the reactor, and the gasket assists in establishing a seal. In some embodiments the unit is mounted into the reactor without the use of threads, mounting without threads can provide resistance to some failure modes that are present when threads are used.

In some embodiments, the system is configured to be used as an in-line sensor in a process. An in-line sensor can be a sensor that is used in an on-going process. In some embodiments the sensor is in a vessel, in other embodiments the sensor is in a conduit or pipe through which a process fluid flows. In some embodiments, the currents measured at a plurality of potentials by voltammetry are used to determine analyte concentration, and the determined analyte concentration is used to control a process parameter. The systems of the present invention are valuable in in-line sensing in that they can be made to be robust, to resist fouling, and are able to measure analyte concentration for long periods of time in media that changes its properties, as in a process such as a chemical reaction.

Methods for Forming Solid State Electrochemical Sensors

Another aspect of the invention provides a method for forming a solid state electrochemical sensor. The method generally comprises having a solid state (e.g., semiconductor) substrate with a surface and immobilizing a redox active moiety with a reduction and/or oxidation potential that is sensitive to an analyte onto the solid state surface.

Some embodiments provide a method for forming an analyte-sensitive semiconductor electrode, the electrode having a semiconductor surface. The method comprises immobilizing a redox-active moiety that is sensitive to the presence of an analyte onto the semiconductor surface.

Any suitable method such as those known in the art or disclosed herein can be used to construct a semiconductor surface as described above that is useful as part of a subject sensor. The redox groups can be immobilized onto the surface chemically or physically. The redox groups can be reacted with the semiconductor surface to attach them to the semiconductor covalently. Alternatively, the redox active groups can be adsorbed to the semiconductor. The redox active groups can also be immobilized by attaching the groups to a polymer that is either covalently or non-covalently bound to the surface. Covalent binding of either the redox group or the polymer to which the redox group is a part to the surface can be beneficial in improving the lifetime and stability of the electrode.

Functional groups can be covalently attached to semiconductors, such as silicon or germanium. Silicon can, for example, form covalent bonds with carbon, and thus is a desirable substrate for functionalizing with carbon based molecules. The covalent binding to the surface can be through a bond between the semiconductor, e.g., silicon, and carbon, oxygen, nitrogen, sulfur, or other atom. In some embodiments the bond to the surface is between the semiconductor, e.g., silicon, and carbon. In some embodiments the bond to the surface is between semiconductor, e.g., silicon, and oxygen.

Figure 4:
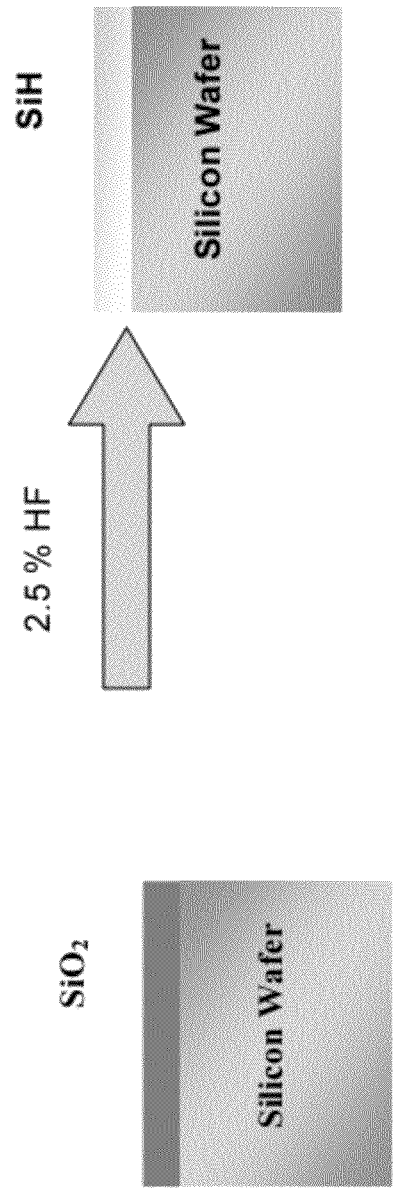
FIG. 4 illustrates a method of preparing of H-terminated silicon surface (Si—H), in accordance with an embodiment of the invention.

In some embodiments, the immobilization of the redox active moiety by covalent binding to the semiconductor surface is accomplished by reaction with a semiconductor hydride, for example, a silicon hydride (Si—H) surface. A semiconductor-hydride, e.g., silicon-hydride surface can be obtained, for example by treatment of the semiconductor, e.g., silicon surface, for example a surface that is in the native oxide state, with hydrofluoric acid (HF). For example, dilute (1-3%) aqueous HF treatment, or, a 40% aqueous $NH_4F$ treatment can be used to create a Si—H terminated surface. Porous silicon, when etched through standard procedures involving HF, can also be used as a Si—H surface. FIG. 4 shows a schematic illustrating the conversion of a native oxide surface to a Si—H surface on a silicon wafer through the treatment of the wafer with a 2.5% aqueous solution of HF. A Si—H surface can also be formed by other processes, for example by decomposition of silanes as described in U.S. Pat. No. 6,444,326. A Si—H surface can also be formed through reacting surface silanol moieties with reagents such as trihydroxyhydridosilane via sol-gel type methods (see e.g., U.S. Pat. Nos. 5,017,540, and 5,326,738) or through dry-etch processes with plasmas of sulfur hexafluoride or Freon 23. A Germanium hydride (Ge—H) surface can undergo the same types of the reactions of Si—H to create covalently bonded redox active reagents. Suitable reactions to covalently bond to the Si or Ge surface are described, for example, in J. M. Buriak, Chem. Review 2002, 102 (5), 1271. The hydrides of other semiconductor substrates can also be prepared and used to covalently bond redox active moieties. Suitable semiconductor hydrides include for example, hydrides of silicon germanium (M. S. Carroll, et al., J. Electrochem Soc. 2000, 147 (12), 4652), gallium arsenide (P. E. Gee, et al., J. Vacuum Sci. Tech. A: Vacuum Surf. Film 1992, 10 (4), 892), gallium nitride, diamond film (S. Yamashita, et al., U.S. Pat. No. 5,786,604 (1998)), and indium phosphide (Y. Sun, et al., J. Appl. Phys. 2005, 97, 124902).

The semiconductor-hydride surface, e.g., Si—H surface, can be reacted with a variety of functional groups to create covalent bonds and thereby attach a redox active moiety to the semiconductor surface. The Si—H surface, Ge—H surface or other Semiconductor-H surface can participate in hydrosilylation reactions, involving the addition of, for example, the Si—H across an unsaturated site to form a Si—C, Si—O, or Si—N bond to the surface. Functional groups which can be used in these reactions including hydrosilylation include alkenes, alkynes, imines, carbonyls and oximes. These reactions, including hydrosilylation can be carried out thermally, photochemically, with a metal catalyst or with a radical initiator (see Buriak, Chem. Commun., 1999, 1051-1060). The Si—H surface or other semiconductor-H surface can also be reacted with alkyl or aryl carbanions through, for example, Grignard, or lithium reagents. In some embodiments, a Si—H surface or other semiconductor-H surface can react with azido, diazo, and diazonium groups. Suitable diazonium reactions are described, for example, in Stewart et al., J. Am. Chem. Soc. 126, 2004, 370-378.

FIG. 5 illustrates the reaction of a surface Si—H with an aldehyde functionality attached to a ferrocene redox active moiety to create a covalently bound ferrocene through a Si—O bond. FIG. 5 also illustrates the reaction of a surface Si—H with a vinyl functional group attached to a ferrocene redox active moiety to create a covalently bound ferrocene through a Si—C bond. FIG. 6 illustrates the reaction of a surface Si—H with an aldehyde functionality attached to an anthracene redox active moiety to create a covalently bound anthracene through a Si—O bond. FIG. 6 also illustrates the reaction of a surface Si—H with a vinyl functional group attached to an anthracene redox active moiety to create a covalently bound anthracene through a Si—C bond. FIG. 7 illustrates the reaction of both a ferrocene redox active moiety and an anthracene redox active moiety through vinyl functionality to produce a silicon surface with a covalently attached redox group that is sensitive to hydrogen ion (anthracene) and a covalently attached redox group that is insensitive to hydrogen ion (ferrocene). In some embodiments, a carbonyl group such as an aldehyde group is substituted for the vinyl functionality for providing attachment to the surface.

The redox active moieties can alternatively be attached covalently to the surface by direct reactions with a semiconductor, e.g., silicon surface from which all functionality has been removed, typically by high temperature and vacuum. The pure silicon surface, for example, can react directly, for example with alkenes and alkynes to form Si—C covalent attachment. (see Bateman, et. al., Angew. Chem. Int. Ed. 1998, 37(19), 2683-2685). Diazonium species can also be used to functionalize the surface either thermally or electrochemically. In some embodiments, ultrahigh vacuum techniques can be used to prepare the functionalized surfaces of the invention, for example by [2+2] Reactions of alkynes and alkenes or Diels-Alder ([4+2]) reactions of dienes with reconstructed Si surfaces.

Capping of semiconductor oxide surfaces such as silica and glass surfaces with alkyl-, alkoxy- and chloro-silanes may also be used to functionalize the semiconductor surface.

The semiconductor surface can contain oxide functionality including hydroxy functionality (native oxide). In some embodiments, the semiconductor electrodes of the invention are modified by covalent attachment to this oxide functionality. For example, the hydroxy groups of silicon or other semiconductor elements can be coupled to surface bound groups using the many reactions known in organic chemistry for carbon bound hydroxy groups, including for example, the formation of esters and ethers. One derivatization method involves the use of a carbodiimide for coupling to the surface. Exemplary carbodiimides include, for example, dicyclohexylcarbodiimide (DCC), or (1-ethyl-3-[3-dimethylaminopropyl]carbodiimide hydrochloride) (EDC).

The redox active moieties can also be attached covalently to the surface by reactions with the native oxide, —O or —OH on the semiconductor surface. Many methods are known for carrying such reactions to form covalent bonds through various functional groups (see Maoz et al., J. Colloid. Interface Sci., 1984, 100, 465-496). In some embodiments an indirect approach can be employed in which an alkoxysilane comprising other reactive functionality is reacted with the —O or —OH groups on the semiconductor surface to covalently attach the alkoxysilane to the semiconductor surface. The other reactive functionality on the alkoxysilane can then be used to covalently attach a redox active moiety to the surface. In these embodiments, the alkoxysilane can become a linker or portion of a linker. The other reactive functionality can be any reactive functionality that can be used to attach a redox active moiety. The functionality can be, for example, an olefin, an acetylene, an amine, a mercaptan, or an epoxy group. The reaction used to couple the alkoxysilane to the redox active moiety can be, for example a, Diels-Alder reaction, Michael addition, click chemistry, or epoxy chemistry. Semiconducting polymers comprising redox active moieties can be polymerized onto a surface, graft polymerized onto a surface, photo-polymerized, or pre-formed and cast onto a surface.

In some embodiments, the reactions described above for covalently attaching functional groups to the semiconductor surface are used to attach a linker group or portion of a linker group having a chemical functionality that can be used to covalently bind the redox active moiety to the surface in a subsequent step.

Reactions that can be used to covalently attach a redox active moiety to the semiconductor surface include hydrosilylation, free radical reactions, carbodiimide coupling, Diels-Alder reactions, Michael addition, epoxy reactions, or click chemistry (see, e.g., Evans et al. *Australian Journal of Chemistry* 60 (6): 384-395 (2007).

Organic semiconductor substrates of the invention can in some embodiments be modified to attach redox active species after the formation of the organic semiconductor. For example, an organic semiconductor can be cast into a film. In some embodiments the organic semiconductive polymers, for example, polyaniline, polypyrrole, and polythiophene are prepared by chemical or electrochemical oxidation. The semiconductive polymer can be subsequently modified using, for example, the chemistry described for the attachment of redox active agents to the inorganic semiconducting substrates. In some embodiments, the semiconductive polymers can comprise functional groups that can be used to attach redox active species to the semiconductive polymer. For example, the sulfonic acid groups in poly(anilinesulfonic acid) can be used to immobilize aminoferrocene, 1,1'-diaminoferrocene, and aminoanthracene through sulfamide formation. In some embodiments, a pyrrole, thiophene or aniline monomer can have a functional group such as an N-hydroxy succinimide ester, a carboxylic acid, or a reactive vinyl or allyl group. The monomers can then be polymerized, for example electropolymerized, and the redox active moiety can be attached to the functional group on the polymerized monomer.

In some embodiments, the redox active moiety can be incorporated into the semiconductive polymer itself, for example as part of the backbone of the polymer. For example, redox active groups within poly(ferrocenyl vinylene phenylene vinylene), poly(fluorine), and poly(carbazole) that comprise redox active moieties in their main chains, which can be used for analyte, e.g., pH sensing.

In some cases the surface of the semiconductor is modified by coating the surface with conductive compounds such as metals or metal oxides. In some embodiments, the semiconductor is coated with gold, silver, palladium, copper, platinum or other metals. The metals can be coated from solution, for example by electrodeposition, or can be coated onto the surface with vacuum techniques such as plasma deposition, or metal vaporization. The semiconductor surface can be coated with conductive or semiconductive metal oxide compounds such as indium-tin oxide. When these materials are coated onto the semiconductor electrode surface, the redox-active agents are attached to the semiconductor electrode by attachment to the layer on the semiconductor electrode.

Where a linker group is used, the linker can be small, for example one to 3 atoms, or can be longer, e.g., 20 to 100 atoms. The linker can also be any size between the small or longer linker. In some embodiments, the linker is relatively short allowing for the redox active moiety to be close to the surface, which can be beneficial for electron transfer. In some embodiments the linker is provided such that the redox active agent is held 1, 2, 3, 4, 5, 6, or 7 atoms from the surface of the semiconductor. Where a short linker is used, the redox-active moiety is held close to the surface. Where a longer group is used, the redox active moiety may be able to move away from the surface, for example further out into the solution. Linker groups can comprise hydrophilic, hydrophobic groups, or mixtures thereof. Linker groups can comprise, for example, hydrocarbons, alkenes, alkynes, esters, ethers, amides, amines, carbonyls, thiols, olefins, silicones, or other organic, inorganic or organometallic groups. The linker groups can be formed by polymerization or oligomerization reactions such as free radical or anionic polymerization. The linker group can comprise, for example, ethylene oxide, propylene oxide, or acrylamide repeat units. Linkers can have ring structures including aromatic rings. The variation in the linker structure can be used to vary the mobility of the redox-active moiety in the solution. If the linker is too long and densely packed the redox active moiety can be far enough away from the surface such that the electron transfer to the electrode surface may be compromised. In these cases, having a linker that has electrical conductivity can be useful.

A redox-active moiety may be highly substituted, and can still act as a redox-active moiety. Thus, for example, the redox-active moiety ferrocene includes substituted ferrocenes, ferrocene polymers, and ferrocene covalently attached to the surface via linker molecules.

In some embodiments, the redox-active moiety can be incorporated into a polymer, and the polymer comprising the redox active moiety can be immobilized onto the semiconductor surface. The immobilization of the polymer can be either chemical or physical. The immobilization of the polymer can be through covalent bonds, or through adsorption of the polymer to the semiconductor surface.

The redox active moieties can be incorporated into any type of polymer that can be immobilized onto the surface of the semiconductor surface. Types of polymers that the redox active moieties can be incorporated into include biopolymers such as RNA, DNA or proteins, conductive polymers, fluoropolymers, polyterpenes, inorganic polymers, phenolic resins polyanhydrides, polyesters, polyolefins, polysiloxanes, polyamides, polyimides, polyethers, polyketones, polysulfones, and vinyl polymers.

The polymer comprising the redox active moieties can, in some cases, be produced at the semiconductor surface. For example monomers or oligomers comprising the redox active moieties can be polymerized in the region of the surface to product the polymer near the surface. In some cases, the polymerization can be initiated at the semiconductor surface, resulting in polymer covalently bound to the surface. The polymerization can be initiated at the surface can be initiated, for example by a free radical reaction initiated by a diazo group attached to the semiconductor surface. In other cases, the polymerization can be initiated in solution, for example near the surface, such that the nascent polymer is immobilized onto the surface as it is formed. Methods for determining the appropriate solvent conditions are known. For example by establishing that the monomer and/or oligomer are soluble, while the polymer is insoluble, allowing for surface deposition to occur. The semiconductor surface can comprise polymerizable functional groups that are capable of copolymerizing with the monomers or oligomers comprising the redox active moieties resulting in covalently binding the redox active polymer onto the semiconductor surface.

In some embodiments, a polymer comprising the redox active moieties can be electropolymerized at the semiconductor surface. For example, monomers comprising the redox active moieties are added to a solution, and current is provided through the semiconductor surface causing electropolymerization of the monomers. In some embodiments, the electropolymerization can result in the covalent attachment of the electropolymerized polymer to the semiconductor surface. In other embodiments, the electropolymerization can result in polymerization, for example, at the semiconductor-solution interface, and the polymer that is formed can deposit onto the semiconductor surface, resulting immobilization of the polymer by physisorption to the surface. The polymers can be polymerized onto a surface, graft polymerized onto a surface, photo-polymerized, or pre-formed and cast onto a surface.

The polymers can be chemically or electrochemically deposited on individual microelectrodes, polymerized, as respond to a signal in a reversible manner, in a way that can be electrochemically detected. Other such materials are described by R. W. Murray in Electroanalytical Chemistry, vol. 13, edited by A. J. Bard (Marcel Dekker, NY 1984), the teachings of which are specifically incorporated herein.

In some embodiments, the polymer is formed away from the semiconductor surface, and subsequently immobilized thereto. The polymer can be immobilized onto the surface by a variety of methods including, adsorption from solution, coating including spin coating and dip coating, spraying, printing, electropainting, or electrodeposition.

In some embodiments the semiconductor electrode is formed by contacting an H-terminated semiconductor surface with the one or more redox-active moieties wherein at least one redox active moiety is sensitive to the presence of an analyte, wherein each redox-active moiety comprises a functional group that will react with the H-terminated semiconductor surface to form a covalently bond, thereby forming a derivatized semiconductor surface. In some embodiments, the surface comprises at least two redox active moieties and one of the redox active moieties is insensitive to the presence of the analyte.

Methods for forming semiconductor electrochemical sensors can be applied to forming other solid state electrochemical sensors, such as carbon sensors. It will be understood that in the case of other solid state materials, the doping configuration can be changed to effect desirable sensor properties, such as sensitivities and reliability.

Uses of the Compositions and Devices

Another aspect of the invention provides a method for determining the concentration of an analyte. In an embodiment, the method comprises bringing an electrode of a sensor in contact with the analyte, the electrode comprising a solid state (e.g., semiconductor) substrate with surface having immobilized thereon an analyte-sensitive redox-active moiety. The analyte-sensitive redox-active moiety exhibits an oxidation potential and/or reduction potential that is sensitive to the analyte. Next, a plurality of potentials are applied to the electrode. The current through the electrode is measured at the plurality of potential to determine a reduction and/or oxidation potential of the analyte-sensitive redox-active moiety, thereby determining the concentration of the analyte.

In some embodiments, the method comprises determining the concentration of an analyte by (a) placing an electrode in contact with said analyte, said electrode comprising a solid state (e.g., semiconductor) substrate with surface having immobilized thereon an analyte-sensitive redox-active moiety, said analyte-sensitive redox-active moiety exhibiting an oxidation potential and/or reduction potential that is sensitive to the concentration of the analyte; (b) applying a plurality of potentials to the electrode; and (c) measuring the current through the electrode at the plurality of potentials, and determining a reduction and/or oxidation potential of the analyte-sensitive redox-active moiety, thereby determining the concentration of the analyte.

The method of determining the concentration of the analyte can be used to measure pH by utilizing redox active moieties that are sensitive to hydrogen ion as described above.

The measurement of current at a plurality of potentials allows for carrying out voltammetry for determining the oxidation and or reduction potential of the redox active moiety or moieties immobilized on the surface. The voltammetry used in the method can be, for example cyclic voltammetry, pulse voltammetry, normal pulse voltammetry, square wave voltammetry, differential pulse voltammetry linear voltammetry, or square wave voltammetry. The source for supplying a plurality of potentials can be a potentiostat, for example, a potentiostat capable of applying square waves for square wave voltammetry.

The frequency of the measurement can affect the quality of the data. In some embodiments, square wave voltammograms are currently at a step height of 2 mV, amplitude of 25 mV and a frequency of 10 Hz. In some cases, it is advantageous to increase the frequency. For example, increasing the frequency to 500 Hz can result in a faster scan rate. We have observed that in some cases, a higher frequency results in a higher level of observed current. In some cases, the peak current can shift, for example to more negative potentials upon increasing the operating frequency. In some cases changing the potential at higher frequencies can result in more noise in the square wave voltammograms. In some cases it is advantageous to shield the electrode from the light because in some cases, light can contribute to the background noise.

In some embodiments, the electrode further comprises an analyte-insensitive redox-active moiety having a reduction and/or oxidation potential that is substantially insensitive to the analyte, and the method further comprising determining the oxidation and/or reduction potential of the analyte-insensitive redox-active moiety, and determining the concentration of the analyte from the difference in the oxidation and/or reduction potentials of the analyte-sensitive and analyte-insensitive moieties. The redox-active moiety having a reduction and/or oxidation potential that is substantially insensitive to the analyte can be on the same electrode as the redox-active moiety exhibiting an oxidation potential and/or reduction potential that is sensitive to the analyte, or a different electrode (e.g., separate and electrically isolated electrodes).

Generally, the analyte concentration is determined by using voltammetry to identify the position of current peaks, which current peaks indicate the reduction or oxidation potential of a redox active moiety. In some embodiments, the position of the reduction and/or oxidation potential of the analyte sensitive redox active moiety is used to determine the concentration of the analyte. For example, the position of the current peak with respect to the potential at a reference electrode can be used. This method can be used, for example, where no analyte insensitive redox active moiety is employed.

Where an analyte insensitive redox active moiety is used, detection is generally accomplished by measuring the potential difference, delta E, associated with current peaks for oxidation (or reduction) of the immobilized redox active moieties, where the magnitude of delta E can be related to the concentration of analyte, e.g., hydrogen ion (H+) in solution. That is, in many embodiments, delta E represents the potential difference between the reduction and/or oxidation potential between a redox active analyte sensitive moiety and a redox active analyte insensitive redox active moiety. The analyte insensitive redox active moiety which has an electrochemical response that is insensitive to variations in the medium serves as the reference. Current peaks for oxidation or reduction of the reference and indicator can be determined from a voltammograms using a counter electrode, and without the need for a reference electrode.

In some embodiments the measured current through the electrode at the plurality of potentials is used to determine the concentration of the analyte. The determination of the concentration using the measured current (e.g., current peaks) can be accomplished by using a computation system that communicates with the device for measuring current. The computation system can apply algorithms for calculating reduction or oxidation potential from the measured current at a plurality of potentials from the voltammetry measurements. The computing systems can be part of the sensing system, in some cases allowing the sensing system to be self contained. The computing system can utilize its memory for storing raw or processed data from the sensors. The method can further comprise communication between the computing system and the sensor via transmission device that will wirelessly or by wire transmit processed data to an external device.

Carrying out the method typically requires the use of at least one other electrode (the counter electrode). The counter electrode is used to complete the electrochemical circuit to make the measurements described herein. The counter electrode is generally made of a material that is chemically inert to the medium so that its potential does not change significantly during the course of measurement. Suitable materials in many applications include platinum, gold, stainless steel, and carbon. In some cases, the counter electrode can be incorporated into the chip that also comprises the semiconductor sensor electrode.

A reference electrode is optional and is used as an additional electrode in some embodiments of the method of measuring analyte concentration. In the case of a three-electrode system, the counter electrode generally completes the circuit, allowing current to flow through the cell, while the reference electrode maintains a constant interfacial potential difference regardless of the current. In the case where the system comprises an analyte sensitive redox active moiety and an analyte insensitive redox active moiety, the analyte insensitive redox active moiety can act as a reference, allowing the potential difference to be used to determine analyte concentration. Even when an analyte insensitive moiety is also used, in some embodiments, a reference electrode will still be used. In some embodiments, pseudo-reference electrodes can also be utilized. Reference electrodes which can be employed are described above.

In some embodiments, the sample is a liquid sample, and the electrodes are each in contact with the liquid. In some cases, the sample will not be a liquid, but may be a solid, generally comprising a solid electrolyte, or a gas.

In some embodiments, the method involves the in-line sensing of a process. An in-line sensor can be a sensor that is used in an on-going process. In some embodiments the method comprise the use of a sensor is in a vessel, in other embodiments the sensor is in a conduit or pipe through which a process fluid flows. In some embodiments, the method comprises using currents measured at a plurality of potentials by voltammetry to determine analyte concentration, and the determined analyte concentration is used to control a process parameter. The systems of the present invention are valuable in in-line sensing in that they can be made to be robust, to resist fouling, and are able to measure analyte concentration for long periods of time in media that changes its properties, as in a process such as a chemical reaction, biochemical reaction, or fermentation.

In some cases, under remote monitoring the sensor can be programmed to automatically take readings. The automatic readings can be programmed to occur on a periodic basis, to occur upon the happening of some event, or to occur when the sensor is prompted. The periodic events can be separated on the order of seconds to on the order of months. The happening of some event could be, for instance at the point when the measured solution reaches a certain volume level, or at given points in the steps of a manufacturing process (e.g., at the beginning of or end of a step, or upon the addition of a reagent to a vessel).

Remote monitoring generally includes communication from the remote sensing unit, and/or communication to the remote sensing unit. The communication to and from the remote sensing unit can be done with transmission lines, and/or wirelessly. Any type of signal including, for example, digital, analog, wideband, narrowband, or combinations thereof, can be used.

Another aspect of the invention provides voltammetric monitoring of pH with a semiconductor electrode as part of process control in processes. In an embodiment, a voltammetric pH measurement is made in an industrial process stream, and the pH value from that measurement is used to as input to a decision on the adjustment a process parameter. In an embodiment, the pH value from the voltammetric pH measurement with a semiconductor electrode is used to decide whether or not to add one or more components to the process, and/or to decide how much of the component to add. In some embodiments, the pH value is used to control the pH in a part of the process, for example, as input into the decision on the addition of either acidic or basic components. In some embodiments, the pH value is used to determine whether a process has reached a certain stage, for instance, whether a reaction is at completion. In some embodiments, the pH value is used to determine the addition of nutrients or other components to a reaction containing an organism to maintain the health and productivity of the organism.

The process control step can be automated such that a given pH measurement value from the sensor results in the change of a process parameter without the intervention of a person. In other embodiments, the pH measurement is viewed by a person who uses the information to make the decision the change of a process parameter.

The process control step can be controlled by a voltammetric pH system with a semiconductor electrode that has a sensor, a voltage source, a current measuring detector, and a computer for determining the pH from the current measurements. The voltammetric pH system can be in communication either with a process control system, or with an operator, by analog or digital means, either with a wire, wireless connections, fibers or combinations thereof.

Another aspect of the invention is a method of voltammetric pH sensing with a semiconductor electrode wherein the pH sensor requires little calibration. In some embodiments, the pH sensor is substantially free of the need for calibration or re-calibration. Substantially accurate measurements may be made without re-calibration.

The use of the voltammetric pH sensing with a semiconductor electrode has a number of advantages. For example, the sensors of the present invention generally comprise solid-state sensors. The sensors of the present invention have a built-in internal standard such that calibration is not required. The sensors of the present invention can be constructed to be physically robust, such that they are not prone to breakage. The sensors of the present invention can be made to be relatively insensitive to fouling. The sensors of the invention can be constructed to be resistant to chemical sterilization such as exposure to ethylene oxide, UV stabilization, gamma irradiation, electron beam irradiation, and temperature treatment. The sensors of the invention can be constructed to be resistant to high humidity and high temperature treatment under pressure such as experienced in an autoclave.

The voltammetric pH sensing methods with a semiconductor electrodes comprise reactions carried out in stainless steel reactors, glass reactors (e.g., for product development), and disposable reactors (e.g., plastic reagent bags), for example reactors described by manufacturers such as Wave Biotech, Hyclone, Xcellerex, and Stedim.

Another aspect of the invention provides methods for voltammetric pH sensing with a semiconductor electrode for processing including chromatography and tangential flow ultrafiltration.

Another aspect of the invention is as a sensor in a remote monitoring system such as a drug (pharmaceutical agent) delivery system. Such a system is described, for example, in U.S. Patent Application 2003/0153900, which is entirely incorporated herein by reference. The analyte monitoring system or monitoring and drug (pharmaceutical agent) delivery system can be partitioned into a disposable module, a reusable module and a personal digital assistant (PDA) module. A PDA is typically a portable, e.g., handheld device that has computing and networking capability, and a user interface, with output, e.g., a display, and input, e.g., stylus, keyboard, and/or touchscreen capability. This configuration optimally distributes functionality among these three configurations to achieve certain advantages. However the invention is not limited to this configuration. For example, a one-unit disposable device including all electronics, microneedles, chemistry, sensors, mechanics and user interface may be alternatively employed. Or, more relevantly, the design of the invention allows for any distribution of components between one or more system modules. For example, components may be partitioned among one or more system modules based on the overall system cost, user safety and/or performance concerns.

The disposable module contains those components that once used must be discarded to maintain safety and accuracy. This module preferably includes any structural or mechanical elements to maintain integrity, sterility and/or an electromechanical interface to any reusable components. Therefore this system module can include, for example: microneedles, a microfluidic assembly, membrane, reagent chemistry and associate housing materials. The portion of a sensor which is in contact with a biological fluid, for example, may be part of the disposable module. This module can also include retaining mechanisms for establishing and maintaining intimate contact with the body thereby providing mechanical retention of the analyte monitoring/drug (pharmaceutical agent) delivery system.

The reusable module generally contains those components that control, automate motion, measure the analyte concentration, alarm the user, transmit data to the PDA module. This module can also include retaining mechanisms. Generally, this module includes: a microprocessor with associated circuitry (e.g., memory, supporting electronics and the like), sensing circuitry, including, for example, a voltage supply and current measuring device, drive mechanisms such as motors or the like, a power supply (e.g., battery) and an interface operable to communicate with a portable computing device or PDA. The interface can be RF, magnetic or inductive, optical or the like. The reusable module can also have an audible or vibration alarm to notify the user that user action intervention is required.

The PDA module generally includes a separate user interface via a portable computing device such as a personal digital assistant (PDA), handheld computer or the like for controlling and/or interacting with the device. A typical portable computing device includes a processor, memory, associated circuitry, a display (e.g., monochrome or color LCD) and an input device such as a key pad, touch screen (e.g., integrated with the display) or the like and an operating system. The display can show the value of the analyte to be measured, could provide the user with instructions on how to respond to the measured level of analyte, or may tell the user what automatic actions have been taken in response to a measured level of analyte.

Today, portable computing devices with improved operating system software and user interfaces are readily available. These devices provide the potential for rich and extended functionality. For example a typical PDA includes a relatively large viewing screen and can also include wireless communications mechanisms, a sophisticated operating system and a variety of business and personal software (calendars, scheduling, etc.). The invention preferably includes the use of a PDA to provide the proprietary software (programs) for autonomous operation with an improved user interface.

For example, the PDA module can provide the user with software that facilitates informed decisions to help a patient user more optimally adjust either drug levels or behaviors to more optimal levels. The PDA configuration provides a user interface and preferably allows users the ability to program and or control testing. The user can view individual analyte measurements and graphically display analyte level trends by the day, week or custom time period. The PDA can be used to display any and all of the measurements recorded by the system. Using the proper software, the user can be provided with recommendations for drug regiment modification. In some cases, the user can program the times when their analyte tests are to be taken. Preferably, the user can also set the upper and lower limits for alerts.

The system can be programmed such that whenever a user makes changes and with verification from the user, the information can be wirelessly downloaded to the system. During the day the user may not need to use the PDA unless alerted by the system to check for an analyte reading. The user can initiate a test from the PDA if wanting to make an immediate measurement. Once the user selects this command, verifies it, and transmits it to the reusable module, a confirmation is made back to the PDA.

Another aspect of the invention comprises drug dispenser capsule comprising a voltammetric sensor. In some embodiments, the drug dispenser capsule comprises a semiconductor based voltammetric sensor as described herein. The drug dispenser capsule of the present invention internally senses a biologic condition by the detection of the presence or amount of an analyte, and internally dispenses drugs within the digestive tract of a body (e.g., a human body or animal body) based upon the sensed level of analyte. The capsule is inert and is therefore swallowable and passable through the digestive tract without being consumed. By sensing the level of one or more analytes, the swallowable drug dispenser capsule senses information the digestive tract or senses conditions within the digestive tract that are indicative of conditions in other organs (e.g., skin). In addition to the voltammetric analyte sensor, the capsule contains one or more other sensors (e.g., chemical, electrical, etc.) so that more types of biologic data can be tracked through the digestive system. In response to that sensed information, the capsule dispenses a bioactive substance within the digestive tract without the need to transmit or receive signals from a remote transmitter/receiver, and without active human or computer management. Drug dispenser capsules are described, for example, in U.S. Pat. No. 6,929,636, which is entirely incorporated herein by reference.

The swallowable drug dispensing capsule comprising a voltammetric sensor can include, for example, sensors, a controller, memory, optional programmable logic, a power supply, a microactuator, a drug storage module, and communication interface having at least one of the following types of communication modules: radiofrequency; ultrasonic; and/or infrared. In one preferred embodiment, at least memory, and preferably also controller and/or programmable logic are embodied on a semiconductor-based, e.g., silicon-based, module in one or more semiconductor chips.

In some embodiments, the swallowable drug dispensing capsule has multiple sensors that are arranged an outer surface of capsule in a desired predetermined orientation that is expected to expose each sensor to a targeted bodily condition or landmark within the human body. Each sensor can comprise a single type of sensor such as an image detector or a different type of sensor (e.g., chemical, electrical, temperature, etc.). Chemical detectors detect the presence of many analytes, such as pH, or other analytes.

The swallowable drug dispensing capsule of the invention can have a controller that regulates communication between sensors and memory, communication between memory and any remote controllers outside of the human body, and communication with programmable logic component(s). Finally, controller can operably control both communication interface and a microactuator. The controller typically is a logic controller and includes a microprocessor. The controller may also comprise one or more logical devices (e.g., a logic gate) capable of performing a sequence of logical operations.

The swallowable drug dispensing capsule generally has a memory or storage device that is typically an ultra-high capacity storage device, and which is often based on a semiconductor chip, e.g., a silicon chip.

The swallowable drug dispensing capsule generally has a drug storage module and a microactuator. The drug storage module represents a container for holding a drug or bioactive substance that may be released, for example, into the digestive tract. Accordingly, the drug storage module also includes one or more selectively activated dispensing ports that open in an outer surface of capsule. The microactuator can have a chemically activated or electromechanically activated mechanism for causing the drug storage module to release its contents. The swallowable drug dispensing capsule has a suitable power supply, such as a lithium-ion battery, which is relatively non-toxic. Alternatively, other power supplies that are suitable for in vivo environments can be used.

The swallowable drug dispensing capsule generally has a communication interface that includes any suitable wireless transmission technology (e.g., ultrasonic, radiofrequency, etc.) that readily permits communication to and from the capsule while the capsule is in digestive tract and the remote transmitter/receiver which is located remotely outside of the body. However, a wireless port is preferably used for communicating with capsule after capsule is captured from the body. Likewise, a wireless port may be used for programming the controller, memory, and/or logic component prior to insertion of capsule within the body to determine the manner that the sensors will operate and communicate with the memory, as well as the manner that microactuator will operate and communicate with memory via controller.

In use, the sensors, including the voltammetric sensor of the capsule sense analyte concentrations and biologic data within the digestive tract and the sensed data is passed through the controller for storage in memory and/or comparison with a stored data profile in memory and/or logic. After the predetermined criteria are met, controller activates microactuator to dispense the drug from drug storage module into digestive tract. The sensed data optionally is stored in memory and retrieved via the communication interface after capture of capsule upon exiting the digestive tract. Finally, a wireless communication system optionally can be used in addition to, or as an alternative to, controller and memory to facilitate evaluating and storing sensed data and to dispense drugs upon selective activation at the appropriate time.

The semiconductor electrode voltammetric pH sensors of the present invention can be used in manufacturing operations such as the manufacture of coatings, cleaners and sealers that enhance paint and finish bonding, metal passivation to protect substrates during shipment and storage, paint spray booth treatments that enhance quality and efficiency, and air scrubbers that limit pollutant emissions. In these applications, the reliable measurement of pH can be an integral part of the process.

In some embodiments, sensors can be used as embeddable corrosion measuring instruments that are capable of providing information related to corrosion rate, corrosion potential, conductivity and chloride concentration, and/or pH levels of steel rebar reinforced structures. The devices can be used to monitor the integrity of the steel. The devices and systems of the present invention do not require a direct electrical connection to the reinforcement steel within the structure, using the structural steel as one of the referencing materials. Since the disclosed instruments do not require proximity to the steel within the structure, the instruments can be dispersed at critical locations within the structure, regardless of steel placement. In some embodiments, the systems and devices are self-contained, incorporating all required sensing electrodes and electronics. The devices can be deployed as described in U.S. Pat. No. 6,690,182, which is entirely incorporated herein by reference.

The semiconductor electrode voltammetric pH sensors of the present invention can be used in winemaking. Measurements of various properties including pH are taken throughout the process, including during (1) pressing, (2) primary fermentation, which often takes between one and two weeks, where yeast converts most of the sugars in the grape juice into ethanol (alcohol) (3) secondary fermentation.

The semiconductor electrode voltammetric pH sensors of the present invention can be used in brewing. The measurement of pH can be important at the various stages of brewing, for example, at mashing, lautering, lauter tun, mash filter, boiling, whirlpool, wort cooling, fermenting, conditioning, filtering, and secondary fermentation. The semiconductor electrode voltammetric pH sensors of the present invention can be particularly important during fermentation, where the voltammetric pH sensors of the present invention are advantageous as they require little to no calibration, and can be made to resist fouling during the fermentation process.

The semiconductor electrode voltammetric pH sensors of the present invention can be used in the production of biofuels, including the production of biodiesel, ethanol, butanol, and substitutes for gasoline, diesel, jet fuel, and additives to be used in any of the forgoing. The production of ethanol includes both the process of converting the cellulose to sugars, and the process of converting the sugars to ethanol. Although there are several key technological differences in how ethanol is produced from corn or cellulosic feedstock, both paths to ethanol production typically require a fermentation step that involves the conversion of glucose and other sugars to ethanol. Currently, baker's yeast, *Saccharomyces cerevisiae*, provides the primary microbiological system used by the corn-based ethanol industry. The methods of the present invention relate to ethanol production for fuel from *Saccharomyces cerevisiae* and other organisms. The control of pH can be useful in catalytic biofuel production processes, such as for the production of biofuel.

The semiconductor electrode voltammetric pH sensors of the present invention can be used in oil recovery and refining. The sensors can be incorporated into down-hole devices for measuring the analytes present in the down-hole environment. The sensors can be used in other aspects of processing the oil such as in oil refining.

The semiconductor electrode voltammetric pH sensors of the present invention can be used in the production of biopharmaceuticals, for example, medical drugs produced using biotechnology. They include, for example, proteins (including antibodies), nucleic acids (DNA, RNA or antisense oligonucleotides) used for therapeutic or in vivo diagnostic purposes. Biopharmaceuticals are produced by means other than direct extraction from a native (non-engineered) biological source. An example is recombinant human insulin (rHI, trade name Humulin), which was developed by Genentech and marketed by Eli Lilly.

Another aspect of the invention is a semiconductor electrode voltammetric pH sensor for the production of biopharmaceuticals including: blood factors (e.g., Factor VIII and Factor IX), thrombolytic agents (e.g., tissue plasminogen activator), hormones (e.g., insulin, growth hormone, gonadotrophins), haematopoietic growth factors (e.g., erythropoietin, colony stimulating factors), interferons (e.g., interferons-α, -β, -δ), interleukin-based products (e.g., interleukin-2), vaccines (Hepatitis B surface antigen), monoclonal antibodies (e.g., infliximab, basiliximab, abciximab, daclizumab, gemtuzumab, alemtuzumab, rituximab, palivizumab, trastuzumab (herceptin), and etanercept) and other products such as tumor necrosis factor, and therapeutic enzymes.

Another aspect of the invention is a method for forming a protein comprising carrying out a fermentation reaction that produces such protein, wherein the pH of the fermentation reaction is controlled by measuring the pH with a pH sensor comprising a solid state (e.g., semiconductor) electrode with a surface having immobilized thereon a redox active moiety that is sensitive to the presence of hydrogen ion, and using the measured pH to control the pH of the fermentation reaction. The solid state electrode in some cases is formed of a semiconductor, such as silicon. In some embodiments, the control of the pH can be manual, for instance, where an operator reads the pH from the pH sensor and uses the measured pH to determine whether or how much to adjust the pH, and in other embodiments, the control can be automatic, where the pH measurement is read by instruments that can adjust the pH based on the value of the measurement received.

The semiconductor electrode voltammetric pH sensors of the present invention can be used for biopharmaceuticals produced from microbial cells (e.g., recombinant *E. coli*), mammalian cell lines and plant cell cultures in bioreactors of various configurations.

Cell culture requires cells to be grown, often under a strict set of conditions to maintain the health of the cells and maximize the production of the culture. Cells are grown and maintained at an appropriate temperature and gas mixture (for example, 37° C., 5% CO2) in a cell incubator. Culture conditions vary widely for each cell type, and variation of conditions for a particular cell type can result in different phenotypes being expressed.

Aside from temperature and gas mixture, the most commonly varied factor in culture systems is the growth medium. Recipes for growth media can vary in pH, glucose concentration, growth factors, and the presence of other nutrient components. The effect of changes in pH can be dramatic in some cases, and it can be important to maintain the pH. The devices, systems, and methods of the invention allow for control of pH within a range of 1, 0.5, 0.02, 0.1, 0.05, 0.02, 0.01 pH units or less to maintain the growth and health of the cells. The semiconductor electrodes of the present invention allow for the accurate measurement of pH with limited fouling, and in some embodiments, no need for calibration.

The semiconductor electrode voltammetric pH sensors of the present invention can be used for cells that are grown completely in solution, and for cells that are grown on a substrate. Some cells naturally live without attaching to a surface, such as cells that exist in the bloodstream. Others require a surface, such as most cells derived from solid tissues. Cells grown unattached to a surface are referred to as suspension cultures. Other adherent cultures cells can be grown on tissue culture plastic, which may be coated with extracellular matrix components (e.g., collagen or fibronectin) to increase its adhesion properties and provide other signals needed for growth.

Figure 17:
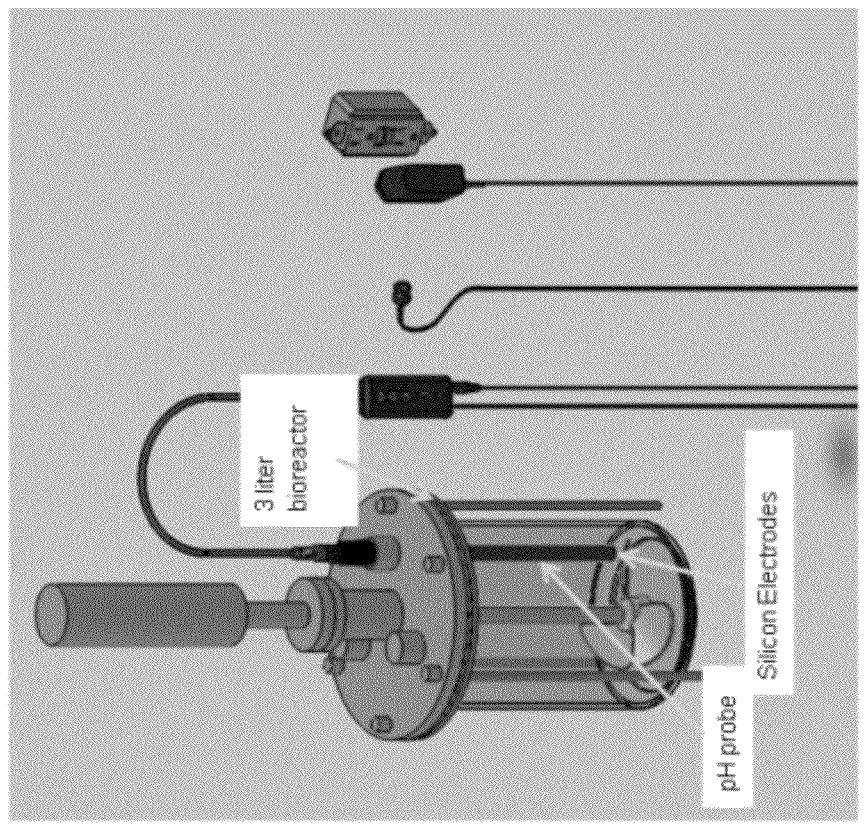
FIG. 17 is a drawing of an embodiment of a bioreactor of the invention comprising a silicon-based voltammetric sensor, in accordance with an embodiment of the invention.

Another aspect of the invention is a bioreactor or fermentor in which the reaction or fermentation occurring therein is controlled by a semiconductor based voltammetric sensor of the invention. In an embodiment, the invention comprises a bioreactor comprising a semiconductor based sensor wherein the semiconductor sensor comprises a semiconductor surface having immobilized thereon a redox active moiety that is sensitive to the presence of an analyte, such as hydrogen ion, FIG. 17 shows an example of a bioreactor of the invention comprising a probe for measuring pH, and thereby controlling the pH in the reactor during the reaction. The probe comprises an electrode having a semiconductor surface having immobilized thereon a redox active moiety that is sensitive to hydrogen ion. In some embodiments the probe comprises two electrodes, each comprising a semiconductor surface, one of the electrodes having immobilized thereto a redox active moiety that is sensitive to hydrogen ion, and one of the electrodes having attached thereto a redox active moiety that is insensitive to hydrogen ion. In some embodiments the probe further comprises a counter electrode, and in some embodiments it further comprises a reference electrode.

The semiconductor electrode voltammetric pH sensors of the present invention can be used to assist in the successful manipulation of cultured cells. As cells generally continue to divide in culture, they generally grow to fill the available area or volume. This can generate several issues that the reliable measurement of pH can assist with, such as: Nutrient depletion in the growth media; accumulation of apoptotic/necrotic (dead) cells; cell-to-cell contact stimulating cell cycle arrest, causing cells to stop dividing known as contact inhibition; cell-to-cell contact stimulating promiscuous and unwanted cellular differentiation Sometimes these issues can be identified by monitoring pH, alone or in combination with other measurements, and can then be controlled or remediated by adjusting tissue culture conditions that often rely on sterile techniques. These methods aim to avoid contamination with bacteria or yeast that will compete with mammalian cells for nutrients and/or cause cell infection and cell death. The pH measurements of the present invention are amenable to being carried out in a biosafety hood or laminar flow cabinet to exclude contaminating micro-organisms.

The semiconductor electrode voltammetric pH sensors of the present invention can be used for pH sensing in plant tissue culture, bacterial and yeast cell culture, and viral cell culture.

Another aspect of the invention is a semiconductor electrode voltammetric pH sensor for sensing pH in plant tissue culture. The pH measurements of the present invention can be used at any step of plant cell culture. Plant tissue culture is typically performed under aseptic conditions under filtered air. Living plant materials from the environment are naturally contaminated on their surfaces (and sometimes interiors) with microorganisms, so surface sterilization of starting materials (explants) in chemical solutions (usually alcohol and mercuric chloride) is an important first step. Explants are then usually placed on the surface of a solid culture medium, but are sometimes placed directly into a liquid medium, particularly when cell suspension cultures are desired. Solid and liquid media are generally composed of inorganic salts plus a few organic nutrients, vitamins and plant hormones. Solid media are prepared from liquid media with the addition of a gelling agent, usually purified agar. The pH measurements of the present invention can be made in the liquid, in the moist soil, or in the agar. The composition of the medium, particularly the plant hormones and the nitrogen source (nitrate versus ammonium salts or amino acids), and the pH, can have profound effects on the morphology of the tissues that grow from the initial explant. For example, an excess of auxin will often result in a proliferation of roots, while an excess of cytokinin may yield shoots.

The semiconductor electrode voltammetric pH sensors of the present invention can be used with any cell line including: National Cancer Institute's cancer cell lines, zebrafish ZF4 and AB9 cells, Madin-Darby Canine Kidney MDCK epithelial cell line, Chinese Hamster Ovary CHO cells, Insect cell line Sf21, MCF-7 (breast cancer), MDA-MB-438 (breast cancer), U87 (glioblastoma), A172 (glioma), HeLa (cervical cancer), HL60 (promyelocytic leukemia), A549 (lung cancer), HEK 293 cells (kidney—original HEK line is contaminated with HeLa), SHSY5Y Human neuroblastoma cells, cloned from a myeloma, Jurkat cell line, derived from a patient with T cell leukemia, BCP-1 cells (PEL), Primate cell lines, Vero (African green monkey Chlorocebus kidney epithelial cell line initiated 1962), COS-7 (African Green Monkey Kidney Cells), Rat tumor cell lines, GH3 (pituitary tumor), 9L (glioblastoma), Mouse cell lines, 3T3 cells, MC3T3 (embryonic calvarial), C3H-10T1/2 (embryonic mesenchymal), NIH-3T3 (embryonic fibroblast), Invertebrate cell lines, C6/36 *Aedes albopictus* (Asian tiger mosquito) larva, Plant cell lines, Tobacco BY-2 cells (kept as cell suspension culture, they are model system of plant cell).

Another aspect of the invention is a semiconductor electrode voltammetric pH sensor for use in water purification. Water purification is the process of removing contaminants from a raw water source, the goal is generally to produce water for a specific purpose with a treatment profile designed to limit the inclusion of specific materials. Water purification is not only water purified for human consumption or drinking water. The semiconductor electrode voltammetric pH sensors of the present invention can also be used water purified to meet the requirements of medical, pharmacology, chemical and industrial applications. The semiconductor electrode voltammetric pH sensors of the present invention can be used in water purification processes including, but not limited to ultraviolet light; filtration; water softening; reverse osmosis, ultrafiltration; molecular stripping; deionization; and carbon treatment. Water purification may remove particulate sand, suspended particles of organic material; parasites, such as *giardia*; cryptosporidium; bacteria; algae; virus; fungi, etc; minerals such as calcium, silica, magnesium; and toxic metals such as lead, copper; and chrome. Some purification may be elective in its inclusion in the purification process; examples, smell (hydrogen sulfide remediation), taste (mineral extraction), and appearance (iron encapsulation).

Water from any source is applicable to the present invention. Groundwater (well water) is an economical choice for drinking water, as it is inherently pre-filtered, by the aquifer from which it is extracted. Water from an aquifer will have a limited output and can take thousands of years to recharge. Surface water; (rivers, lakes, streams) is far more abundant and is the typical raw water source used to make drinking water, as a water source it is carefully monitored for the presence of a variety of contaminants. The methods of the present invention encompass the voltammetric measurement of pH of these types of water where the pH value of the measurement can be used to decide on the purity of the water.

The semiconductor electrode voltammetric pH sensors of the present invention can be used with water purification methods including: pumping and containment, screening, storage, pre-conditioning, pre-chlorination, and removal of the fine solids, micro-organisms and some dissolved inorganic and organic materials.

Distilled water generally has an average pH of about 7 (neither alkaline nor acidic) and seawater generally has an average pH of 8.3 (slightly alkaline). If the water is acidic (lower than 7), lime or soda ash can be added to raise the pH. Lime is the more common of the two additives because it is cheaper, but it also adds to the resulting water hardness. Neutralizing with soda ash, however, increases the sodium content of the water. Making the water slightly alkaline helps ensure that coagulation and flocculation processes work effectively and also helps to minimize the risk of corrosion in pipes and pipe fittings. The pH value can be used to determine whether water is likely to be hard or soft. In general, water with a low pH (<6.5) is acidic, and tends to be soft, and corrosive. Therefore, the water could contain metal ions, such as iron, manganese, copper, lead, and zinc. In some cases this results in elevated levels of toxic metals. This can cause premature damage to metal piping, and have associated aesthetic problems such as a metallic or sour taste, staining of laundry, and the characteristic "blue-green" staining of sinks and drains. More importantly, there are health risks associated with these ions or contaminants. The primary way to treat the problem of low pH water is with the use of a neutralizer. The neutralizer feeds a basic solution into the water to prevent the water from reacting with the household plumbing or contributing to electrolytic corrosion. Water with a pH>8.5 could indicate that the water is hard. Hard water does not pose a health risk, but can cause aesthetic problems. These problems include an alkali taste to the water, formation of a deposit on dishes, utensils, and laundry basins, difficulty in getting soaps and detergents to lather, and formation of insoluble precipitates on clothing.

Another aspect of the invention is sensing of analyte levels such at the pH of bodies of water for example for resource control. The body of water can be, for example, a lake, ocean, stream, or river. The ability of the invention to be used remotely and to be used without the need for frequent calibration or any calibration at all allows the systems, devices, and electrodes to be deployed remotely in bodies of water to provide information on analytes such as hydrogen ion, etc. in such remote bodies.

Another aspect of the invention is a semiconductor electrode voltammetric pH sensor for the measurement of pH in processes related to sewage treatment. Sewage treatment can have the same steps as described above, but may refer to water that has a higher level of contamination. Raw influent (sewage) can be the liquid and semi-solid waste from toilets, baths, showers, kitchens, sinks etc. Household waste that is disposed of via sewers can compose the sewage. In some areas sewage also includes some liquid waste from industry and commerce.

Stability Control

In some cases, traditional electrochemical sensors can suffer from IV fluctuations during measurement, which can lead to inaccurate measurements and low measurement times as more measurements would have to be taken to obtain a time-averaged measurement. Such fluctuations can lead to instability in square wave voltammetry (SWV).

In some cases, exposing a ferrocene functionalized silicon surface to an alkaline environment can shift the reaction $Fe^{2+} \leftrightarrows Fe^{3+} + e^-$ away from equilibrium. The $Fe^{3+}$ (ferricenium) ions can react with the anion in the alkaline solution and lose the ability to reverse back to $Fe^{2+}$ (ferrocenium) ions. This can adversely affect the stability of an electrochemical sensor having a ferrocene-containing working electrode.

In some embodiments, an electrochemical sensor is provided having one or more working electrodes comprising species that are active to an analyte of interest, the species disposed over a solid state (e.g., semiconductor) surface, such as a silicon surface. One or more of the working electrodes can be covered by a layer of a polymeric material. In an embodiment, one working electrode comprises a layer of a redox-active moiety and a layer of polymeric material over the layer of a redox-active moiety. In another embodiment, an electrochemical sensor comprises two working electrodes with each working electrode comprising a layer of a redox-active moiety and a layer of polymeric material over the layer of the redox-active moiety. The electrochemical sensor can further include a counter electrode and a reference electrode (as described above). In an embodiment, the electrochemical sensor includes two working electrodes, a first working electrode having a redox-active moiety that is sensitive to an analyte of interest (e.g., H+) and a second working electrode having a redox-active moiety that is insensitive to an analyte of interest. In an embodiment, the electrode having a redox-active moiety that is insensitive to an analyte comprises a layer of a polymeric material. In some embodiments, the layer of the polymeric material can include a homopolymer of a copolymer. In an embodiment, the layer of the polymeric material can include a fluoropolymer-copolymer. In another embodiment, the layer of the polymeric material can include a sulfonated tetrafluoroethylene based fluoropolymer-copolymer. In another embodiment, the layer of the polymeric material can include perfluorosulfonate inonomer or a derivative of perfluorosulfonate inonomer. In another embodiment, the layer of the polymeric material can include Nafion, having the formula $C_7HF_{13}O_5S*C_2F_4$, and the following structure:

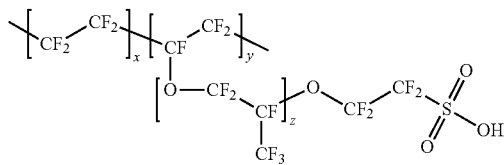

The layer of polymeric material, such as a Nafion membrane (or film or layer), can advantageously stabilize its response in square wave voltammetry (SWV). This can aid in preventing peak potentials of the working electrode from changing with pH, which could otherwise cause deterioration of sensor performance. In addition, the layer of polymeric material can protect the semiconductor surface of the electrochemical sensor against changes in solution pH, which can stabilize the peak position for this electrode in SWV. In an embodiment, in cases in which a working electrode comprises ferrocene, the layer of polymeric material can selectively screen off anions and only allow the passage (or flow) of cations, which can minimize the interaction of anions and ferricenium ions, thereby preserving the integrity of the redox reaction.

In an embodiment, an electrochemical sensor is provided having a working electrode comprising a redox active moiety and a layer of polymeric material over the redox active moiety. The layer of polymeric material can include Nafion. The layer of polymeric material can have a thickness between about 1 nanometer ("nm") and 1000 micrometers ("microns"), or between about 100 nm and 500 microns, or between about 200 nm and 250 microns, or between about 500 nm and 125 microns.

In an embodiment, an electrochemical sensor is provided having a working electrode having a redox-active moiety disposed thereon, wherein the redox-active moiety is sensitive or insensitive to an analyte of interest. A Nafion-containing membrane (or layer) is disposed over the working electrode. In an example, an electrochemical sensor is provided having a working electrode comprising a Nafion-containing membrane over the working electrode, the working electrode having a layer of one or more redox-active moieties.

In an embodiment, an electrochemical sensor is provided having a working electrode comprising a layer of ferrocene, and a layer of a polymeric material over the layer of ferrocene. The layer of polymeric material can include Nafion. The layer of polymeric material can have a thickness between about 1 nanometer ("nm") and 1000 micrometers ("microns"), or between about 100 nm and 500 microns, or between about 200 nm and 250 microns, or between about 500 nm and 125 microns.

In another embodiment, an electrochemical sensor is provided having a working electrode comprising a layer of anthracene, and a layer of a polymeric material over the layer of anthracene. The layer of polymeric material can include Nafion. The layer of polymeric material can have a thickness between about 1 nanometer ("nm") and 1000 micrometers ("microns"), or between about 100 nm and 500 microns, or between about 200 nm and 250 microns, or between about 500 nm and 125 microns.

A working electrode can include a first layer of polymeric material, such as Nafion, and a second layer of polymeric material over the first layer of polymeric material. The second layer of polymeric material may be a protective layer, which may protect the first layer of polymeric material and the working electrode from, for example, corrosion, or damage due to impact. In an example, a working electrode includes a Nafion-containing (e.g., a porous material impregnated with Nafion) over a layer of redox-active moieties, and a layer of a second polymeric material over the Nafion-containing layer. In an example, the second layer of polymeric material includes polyethersulphone (PES).

In some cases, the second layer of polymeric material can be a light blocking layer (see below). The light blocking layer may aid in minimizing, if not eliminating, the interaction of the working electrode with light during operation.

In some embodiments, an electrode, such as a working electrode, can comprise a layer of a composite material over the electrode. The composite material can include a porous material, such as porous plastic or porous silica, which has been treated with a polymeric material, such as Nafion (or other fluoropolymer-copolymer). The porous material in some cases is impregnated with Nafion. In some situations, the Nafion-containing layer selectively filters out negative ions (anions) that may interfere with the operation of the electrode. In some situations, the use of a porous material may advantageously provide thickness uniformity of the Nafion layer over the electrode.

In some embodiments, the layer of the composite material, such as a membrane containing porous plastic and Nafion, has a thickness between about 1 nanometer ("nm") and 1000 micrometers ("microns"), or between about 100 nm and 500 microns, or between about 200 nm and 250 microns, or between about 500 nm and 125 microns. In some embodiments, a porous material used in the preparation of the composite plastic membrane (or film, or layer), such as porous plastic or porous silica, has one or more pores at pore sizes (diameters) between about 1 micron and 1000 microns, or between about 10 microns and 500 microns, or between about 50 microns and 100 microns. In some embodiments, the Nafion content in the pores of the porous material used in the preparation of the composite material, such as porous plastic or porous silica, is between about 1% and 99%, or between about 10% and 50%, or between about 35% and 65%. The porous composite material can be prepared by impregnation or sol-gel synthesis.

In another aspect of the invention, an electrode comprises a layer of a light blocking material that reduces, if not eliminates, the interaction of light with a surface of the electrode, such as a working electrode. Use of a light blocking layer on electrodes has led to the unexpected realization that device performance during device use in ambient conditions (such as upon exposure to sunlight or room light) may be improved if incident light on a surface of a working electrode (and in some cases reference and counter electrode) is minimized, if not eliminated. The light blocking layer in some cases is covered with a layer of a protective material, such as PES. In some embodiments, an electrode having a light blocking layer comprises a light emitting device (see below) on a side of the electrode opposite from the light blocking layer. In other embodiments, the light blocking layer is formed of polyethersulphone (PES), such as an opaque PES or PES that does not transmit light. In some cases, the PES is "black" PES. In some situations, the light blocking layer is a porous material that is optically opaque or otherwise blocks light from reaching a surface of an electrode. The porous material permits an analyte to reach a surface of the electrode while minimizing, if not eliminating, the interaction of light with the surface of the electrode. Examples of such light blocking layers include polymeric materials, such dark porous plastics. In an example, a dark porous plastic includes PES.

In some embodiments, an electrode (e.g., working electrode, reference electrode, counter electrode) comprises a light blocking layer for minimizing the interaction of the electrode and/or light sensitive moieties on or over the electrode with light, such as ambient light. The light blocking layer may be formed of a polymeric material, such as polyethersulphone (PES) (e.g., black PES). In some situations, a light blocking layer may advantageously screen off light without impeding the flow of an analyte (e.g., hydrogen ions), or impeding the interaction of the analyte with the surface of the electrode. In some situations, the light blocking layer can prevent (or minimize) light from inducing electron excitation on the semiconductor surface of the working electrode, which may interfere with the operation of the working electrode.

The light blocking layer may include one or more pores for permitting an analyte from reaching a surface of the electrode, such as a surface of a working electrode having redox active moieties. The light blocking layer may have pores at a pore size (diameter) between about 0.1 micrometers ("microns") and 1 micron, or 0.2 microns and 0.9 microns, or 0.45 microns and 0.8 microns.

In some embodiments, the light blocking layer can prevent between about 50% to about 99.9% of light, or between about 60% and 90% of light, or between about 70% and 80% of light from reaching a surface of an electrode, such as a semiconductor surface that may exhibit sensitivity to light. In some cases, the light blocking layer transmits less than 20%, 15%, 10%, 9%, 8%, 7%, 6%, 5%, 4%, 3%, 2%, 1%, or lower of light incident on the light blocking layer. The percentage of light transmitted through the light blocking layer is proportional to the percentage of light that reaches a surface of an electrode.

In another aspect of the invention, electrochemical sensors are provided having electrodes operatively coupled to light emitting devices. In some examples, electrodes are formed on, or are included in, light emitting devices that are configured to generate light. Light emitting devices in some cases are light emitting diodes (LED's).

In some situations, it has been observed that electrochemical sensors exposed to light sources of variable wavelength and/or intensity, such as ambient light (e.g., sunlight, room light) produces unpredictable or erratic signals (e.g., noise), which may adversely affect device performance. However, it has been observed that operatively coupling electrodes (e.g., working electrodes, reference electrode and counter electrode) to a fixed wavelength, fixed intensity light source, such as a light emitting device (also "light-emitting device" herein), unexpectedly minimizes, if not eliminates such erratic signals during electrochemical measurements. In some cases, exposing an electrochemical sensor to light during use provides for improved sensor operation when the electrode is exposed to ambient light. This advantageously precludes the need to operate the sensor in the dark, for example.

In some embodiments, during use, an electrode is saturated with light from a light source. In other embodiments, during use, an electrode is exposed to light such as electrons and holes generated in the electrode upon exposure to light are at least about 1%, or 10%, or 20%, or 30%, or 40%, or 50%, or 60%, or 70%, or 80%, or 90%, or 95%, or 99% of the maximum concentration of electrons and holes that may be generated in the electrode upon exposure to light.

In some embodiments, a working provided herein includes a layer of a redox active moiety adjacent a surface of the electrode, and a light blocking layer over the layer of the redox active moiety. The light blocking layer in some cases substantially covers the layer of the redox active moiety.

In some embodiments, electrochemical sensors are provided in which one or more electrodes, such as a working electrode, is formed on a light emitting device, such as a light emitting diode, or a plurality of electrodes are formed on a light emitting device. In such a case, light from the light emitting device is incident on an underside of one or more electrodes, and may in some cases propagate through at least a portion of the one or more electrodes. The ohmic contact side of the one or more electrodes may not be configured to come in contact with a solution having an analyte (e.g., W).

In other embodiments, electrodes may not be formed on light emitting devices, but surface of electrodes (e.g., a surface of a working electrode having a redox active moiety) is in view of a light emitting device. In such a case, light from the light emitting device is incident on the surface of the electrode configured to come in contact with a solution having an analyte.

In some embodiments, the working electrode can be operatively coupled to a light source below or above a surface of the working electrode. Light from the light source may minimize, if not eliminate, interactions of light with a surface of the working electrode. In some embodiments, the light source comprises a lamp, a light-emitting diode (LED), or other light emitting device that illuminates a top surface (having redox active moieties) of the working electrode.

In other embodiments, the light source illuminates an underside of the working electrode. The underside may not have redox active moieties. In such a case, the working electrode may be sufficiently thin to permit light to propagate through the working electrode.

Figure 29:
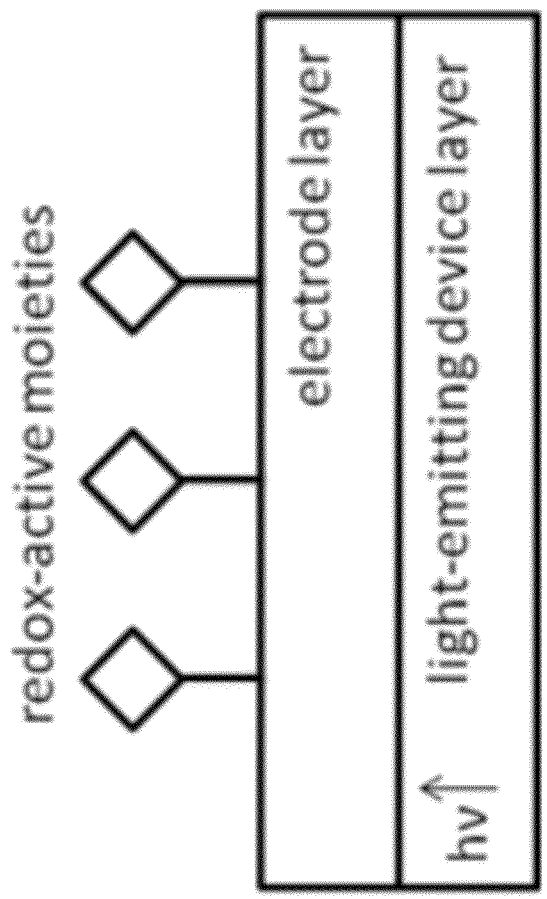
FIG. 29 shows a working electrode having a light-emitting device and an electrode adjacent to the light-emitting device, in accordance with an embodiment of the invention.

FIG. 29 shows a working electrode having a light-emitting device, such as a light emitting diode, and an electrode adjacent to the light-emitting device. In some embodiments, the light-emitting device is a light emitting diode (LED) having an active material (or active region) configured to generate light upon the recombination of electrons and holes. In some embodiments, the working electrode is formed of a semiconducting material, such as silicon. The working electrode can be formed over the LED layer using, for example, spincoating or vapor deposition techniques, such as chemical vapor deposition or atomic layer deposition. The surface of the working electrode further comprises a redox-active moiety immobilized thereon, said redox-active moiety exhibiting an oxidation potential and/or a reduction potential that is sensitive or insensitive to the presence of an analyte. In some embodiments, the redox-active moiety can be immobilized on the semiconducting layer by reactions such as hydrosilylation, free radical reactions, carbodiimide coupling, Diels-Alder reactions, Michael addition, epoxy reactions, or click chemistry.

In some embodiments, the working electrode comprises a non-semiconducting material, such as carbon. In some embodiments, a layer of non-semiconducting material can be combined with the LED layer by, for example, spraycoating or vapor deposition techniques. The surface of the working electrode further comprises a redox-active moiety immobilized thereon, said redox-active moiety exhibiting an oxidation potential and/or a reduction potential that is sensitive or insensitive to the presence of an analyte. In some embodiments, the redox-active moiety can be immobilized on the non-semiconducting layer, such as activated carbon, by first oxidatively treating the non-semiconducting layer to create oxygen groups on the layer (Lemus-Yegres et al., Microporous and Mesoporous Materials 109 (2008), 305-316). The non-semiconducting layer can then be subjected to immobilization reactions.

In some cases, the LED may minimize, if not eliminate, interactions of light with the surface of the working electrode.

In an example, a working electrode includes a light emitting diode having a p-type Group III-V semiconductor material, an active layer (e.g., multiple quantum well active layer adjacent to the p-type Group III-V semiconductor material), and an n-type Group III-V semiconductor material layer adjacent to the active layer. A first electrode is formed adjacent to the p-type Group III-V semiconductor material. A second electrode is formed adjacent to the n-type Group III-V semiconductor material layer. The second electrode may be formed over the n-type Group III-V semiconductor material layer with the aid of a transition layer, such as indium tin oxide. The electrode may be formed of one or more transition metals, such as gold and/or silver. A layer of an insulating material is then formed on the electrode. In some cases, the layer of the insulating material is formed of a metal oxide or a nitride (e.g., silicon nitride). Next, a third electrode is formed on the layer of the insulating material. The third electrode will serve as the back contact to the working electrode. Next, the working electrode is formed on the third electrode. Redox active moieties are then provided on a surface of the working electrode. The working electrode may be formed of a semiconducting (e.g., silicon, germanium, gallium nitride) or non-semiconducting (e.g., carbon, a metal) material.

In some embodiments, a light emitting device adjacent an electrode, such as a working electrode, emits light having a wavelength greater than or equal to about 300 nanometers (nm), 400 nm, 500 nm, 600 nm, 700 nm, or 800 nm. In some situations, the light emitting device emits light having a wavelength above 750 nm or 800 nm. In an example, the light emitting device emits near infrared or infrared light.

Light may be exposed to sensor surfaces having redox active moieties, or sensor surfaces opposite from the redox active moieties (e.g., back surfaces of a sensor). In some cases, the thickness of a working electrode is selected to provide a desirable sensor output when exposed to light from the backside. In some embodiments, a working electrode has a thickness between about 100 nanometers ("nm") and 1 millimeter, or between about 500 nm and 750 micrometers ("microns"), or between about 250 microns and 650 microns.

In some embodiments, exposure of a working electrode to light, such as, e.g., a fixed intensity, fixed wavelength light, provides improved sensor signal to noise. In some cases, the signal to noise is improved by a factor of 10, 100, 1000, 10,000, 100,000, or more.

The wavelength of light emitted by the light emitting device, in some cases, is adjustable. In some cases, the wavelength of light emitted by the light emitting device is adjusted based on the power applied to the light emitting device. In some cases, the sensor has an ambient light sensor that detects the level of ambient light, and adjusts the wavelength of light emitted by the light emitting device. In an example, if the ambient light sensor detects little to no ambient light, the light emitting device will not be used. In another example, if the ambient light sensor detects light above a predetermined threshold, then the light emitting device may be used.

Light emitting devices provided herein may be controlled with the aid of processors and software. The processor may be an on-board processor, such as mounted on a printed circuit board in proximity to the sensor and any ambient light sensor. The processor may aid in regulating the functionality of any of the sensor, the light emitting device, and the ambient light sensor.

Co-Functionalization of Working Electrodes

In another aspect of the invention, an electrochemical sensor is provided having co-functionalized working electrodes. Co-functionalization can permit the use of hydrocarbon molecules as space fillers to cover sites on a silicon hydride (—Si—H) surface that have not been occupied by redox active moieties, such as anthracene and/or ferrocene. The hydrocarbon molecules can block (or passivate) such sites, thereby preventing such sites from interacting with anions and cations during operation of the electrochemical sensor, which can provide for improved device performance.

In an embodiment, an electrochemical sensor comprises one or more working electrodes, a counter electrode and a reference electrode, wherein at least one of the one or more working electrodes is co-functionalized with redox-active moieties and hydrocarbon molecules. In an embodiment, an electrochemical sensor includes a working electrode, a counter electrode and a reference electrode. The working electrode can include a mixed monolayer of redox active species, such as anthracene and ferrocene, and hydrocarbon molecules, such as alkanes, alkenes, or alkynes. In an embodiment, the hydrocarbon is a long-chain hydrocarbon. In another embodiment, the hydrocarbon comprises a chain of 2 or more, 3 or more, 4 or more, 5 or more, 6 or more, 7 or more, 8 or more, 9 or more, 10 or more, 11 or more, 12 or more, 13 or more, 14 or more, 15 or more carbon atoms. In an embodiment, the hydrocarbon molecules can include a decyne having the following structural formula:

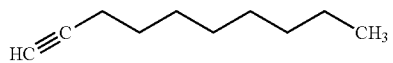

In an embodiment, a working electrode comprises a sub-monolayer coverage redox-active species, with the remaining sites (i.e., S—H sites) covered by a hydrocarbon, such as decyne. In another embodiment, a working electrode can include a mixed layer of ferrocene and a hydrocarbon, such as decyne. In another embodiment, a working electrode can include a mixed layer of anthracene and a hydrocarbon, such as decyne. In another embodiment, a working electrode can include a mixed layer of ferrocene, anthracene, and a hydrocarbon, such as decyne.

Single-Use or Disposable Electrochemical Sensors

In another aspect of the invention, single-use and/or disposable electrochemical sensors are provided. In an embodiment, electrochemical sensors are provided that are suitable for single use applications, disposable applications, or both single-use and disposable applications.

In an embodiment, a disposable electrochemical sensor is provided. In another embodiment, a single-use electrochemical sensor is provided. In another embodiment, a disposable and single-use electrochemical sensor is provided.

In an embodiment, a single-use electrochemical sensor comprises an onboard energy storage device. Such an energy storage device can be configured to store electrical potential energy (e.g., in the form of electrons in excited states) and discharge upon use of the electrochemical sensor. Energy storage devices can be selected from batteries, capacitors, or photovoltaic modules. In an embodiment, an electrochemical sensor comprises a battery, such as, e.g., a lithium ion battery or nickel metal cadmium battery. In another embodiment, an electrochemical sensor comprises a capacitor. In another embodiment, an electrochemical sensor comprises a battery electrically coupled to a capacitor.

In another embodiment, an electrochemical sensor is provided having a replaceable energy storage device, such as a replaceable battery. In such a case, the electrochemical device can be used for a duration determined by the lifetime of the energy storage device. The energy storage device can be subsequently changed, thereby permitting further use of the electrochemical sensor. In another embodiment, an electrochemical sensor having a rechargeable energy storage device is provided. The rechargeable energy storage device can include a rechargeable battery.

In an embodiment, an electrochemical sensor, such as any electrochemical sensor provided herein (e.g., a pH sensor), can include an energy storage device configured to provide charge to the electrochemical sensor. In another embodiment, an electrochemical sensor includes an energy storage device configured to provide charge for up to about 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or 21 days, or 22 days, or 23 days, or 24 days, or 25 days, or 26 days, or 27 days, or 28 days, or 29 days, or 30 days, or 35 days, or 40 days, or 45 days, or 50 days, or 100 days, or 150 days, or 200 days, or 300 days, or 400 days, or 500 days, or 1000 days. In another embodiment, an electrochemical sensor includes an energy storage device configured to provide charge for at least about 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or 21 days, or 22 days, or 23 days, or 24 days, or 25 days, or 26 days, or 27 days, or 28 days, or 29 days, or 30 days, or 35 days, or 40 days, or 45 days, or 50 days, or 100 days, or 150 days, or 200 days, or 300 days, or 400 days, or 500 days, or 1000 days.

In an embodiment, a semiconductor-based electrochemical sensor is provided having redox-active moieties. The sensor can include one redox-active moiety that is sensitive to an analyte (e.g., hydrogen ions) and another redox-active moiety that is insensitive to the analyte. The semiconductor-based electrochemical sensor can further include an on-board energy storage device configured to provide power to the semiconductor-based electrochemical sensor. In an embodiment, the energy storage device can provide power to the semiconductor-based electrochemical sensor for a time period of at least about 1 second, or 10 seconds, or 30 seconds, or 1 minute, or 2 minutes, or 3 minutes, or 4 minutes, or 5 minutes, or 6 minutes, or 7 minutes, or 8 minutes, or 9 minutes, or 10 minutes, or 30 minutes, or 1 hour, or 2 hours, or 3 ours, or 4 hours, or 5 hours, or 6 hours, or 7 hours, or 8 hours, or 9 hours, or 10 hours, or 11 hours, or 12 hours, or 1 day, or 2 days, or 3 days, or 4 days, or 5 days, or 6 days, or 7 days, or 8 days, or 9 days, or days, or 11 days, or 12 days, or 13 days, or 14 days, or 15 days, or 16 days, or 17 days, or 18 days, or 19 days, or 20 days, or 21 days, or 22 days, or 23 days, or 24 days, or 25 days, or 26 days, or 27 days, or 28 days, or 29 days, or 30 days, or 35 days, or 40 days, or 45 days, or 50 days, or 100 days, or 150 days, or 200 days, or 300 days, or 1 year, or 2 years, or 3 years, or 4 years, or 5 years, or 6 years, or 7 years, or 8 years, or 9 years, or 10 years, or 15 years, or 20 years.

In an embodiment, a semiconductor-based electrochemical sensor is provided that is configured for single-use operation. In another embodiment, an electrochemical sensor is provided that is configured to operate, upon first use, for a time period of at least about 1 second, or 10 seconds, or 30 seconds, or 1 minute, or 2 minutes, or 3 minutes, or 4 minutes, or 5 minutes, or 6 minutes, or 7 minutes, or 8 minutes, or 9 minutes, or 10 minutes, or 30 minutes, or 1 hour, or 2 hours, or 3 ours, or 4 hours, or 5 hours, or 6 hours, or 7 hours, or 8 hours, or 9 hours, or 10 hours, or 11 hours, or 12 hours, or 1 day, or 2 days, or 3 days, or 4 days, or 5 days, or 6 days, or 7 days, or 8 days, or 9 days, or 10 days, or 11 days, or 12 days, or 13 days, or 14 days, or 15 days, or 16 days, or 17 days, or 18 days, or 19 days, or 20 days, or 21 days, or 22 days, or 23 days, or 24 days, or 25 days, or 26 days, or 27 days, or 28 days, or 29 days, or days, or 35 days, or 40 days, or 45 days, or 50 days, or 100 days, or 150 days, or 200 days, or 300 days, or 1 year, or 2 years, or 3 years, or 4 years, or 5 years, or 6 years, or 7 years, or 8 years, or 9 years, or 10 years, or 15 years, or 20 years. In another embodiment, after first use, the electrochemical sensor will not function (i.e., the electrochemical sensor will not function beyond the first use).

In another embodiment, an electrochemical sensor comprising one or more working electrodes, a counter electrode and a reference electrode is disposed in a high density polyethylene support that can be directly welded to a surface a bag, such as a polyethylene bag, for single use bag application. Such electrochemical sensors can be configured for use with cell fermentation, media storage, buffer preparation and cell storage.

In an embodiment, a redox-active moiety-containing analyte sensor is provided that is configured for use in a time period of about 1 day, or 5 days, or 10 days, or 20 days, or 25 days, or 30 days, or 1 month, or 2 months, or 3 months, or 4 months, or 5 months, or 6 months, or 7 months, or 8 months, or 9 months, or 10 months, or 11 months, or 1 year, or 2 years, or 3 years, or 4 years, or 5 years, or 6 years, or 7 years, or 8 years, or 9 years, or 10 years. In another embodiment, a redox-active moiety-containing analyte sensor is provided that is configured for use in a time period of at least about 1 day, or 5 days, or 10 days, or 20 days, or 25 days, or 30 days, or 1 month, or 2 months, or 3 months, or 4 months, or 5 months, or 6 months, or 7 months, or 8 months, or 9 months, or 10 months, or 11 months, or 1 year, or 2 years, or 3 years, or 4 years, or 5 years, or 6 years, or 7 years, or 8 years, or 9 years, or 10 years. Such analyte sensors can be configured for use within a particular time period without re-calibration.

Analyte sensors provided herein can have various sensitivities. In an embodiment, a redox-active moiety-containing analyte sensor is provided having a sensitivity between about 5 mV per pH unit and 200 mV per pH unit, or between about 10 mV per pH unit and 100 mV per pH unit, or between about 20 mV per pH unit and 60 mV per pH unit.

Analyte sensors provided herein can have various shelf lives. In an embodiment, a redox-active moiety-containing analyte sensor is provided having a shelf life between about 1 month and 20 years, or between about 2 months and 10 years, or between about 3 months and 3 years. Such analyte sensors can function without re-calibration. In another embodiment, a redox-active moiety-containing analyte sensor is provided having a shelf life of at least about 1 month, or 2 months, or 3 months, or 4 months, or 5 months, or 6 months, or 7 months, or 8 months, or 9 months, or 10 months, or 11 months, or 1 year, or 2 years, or 3 years, or 4 years, or 5 years, or 6 years, or 7 years, or 8 years, or 9 years, or 10 years.

Analyte sensors provided herein can have various accuracies following removal from storage. In an embodiment, a sensor for detecting an analyte is provided having an accuracy to within 0.1% (pH units) while in use or storage for at least 2 years. In another embodiment, a sensor for detecting an analyte is provided having an accuracy to within 0.1% (pH units) while in use or storage for at least 4 years. In another embodiment, a sensor for detecting an analyte is provided having an accuracy to within 0.1% (pH units) while in use or storage for at least 8 years. In another embodiment, a sensor for detecting an analyte is provided having an accuracy to within 0.1% (pH units) while in use or storage for at least 10 years. In some embodiments, sensors can retain their accuracy while in storage without the need for calibration of re-calibration. Such sensors can include redox-active moieties, as described herein.

In an embodiment, a sensor for detecting an analyte is provided having an accuracy of plus or minus 0.0001 pH units, or 0.0002 pH units, or 0.0003 pH units, or 0.0004 pH units, or 0.0005 pH units, or 0.0006 pH units, or 0.0007 pH units, or 0.0008 pH units, or 0.0009 pH units, or 0.001 pH units, or 0.002 pH units, or 0.003 pH units, or 0.004 pH units, or 0.005 pH units, or 0.006 pH units, or 0.007 pH units, or 0.008 pH units, or 0.009 pH units, or 0.01 pH units, or 0.02 pH units, or 0.03 pH units, or 0.04 pH units, or 0.05 pH units, or 0.06 pH units, or 0.07 pH units, or 0.08 pH units, or 0.09 pH units, or 0.1 pH units. Such a sensor can include redox-active moieties, as described herein.

In an embodiment, a sensor for detecting an analyte is provided having an accuracy to within 0.001 pH units while in use or storage for at least 2 years. In another embodiment, a sensor for detecting an analyte is provided having an accuracy to within 0.001 pH units while in use or storage for at least 4 years. In another embodiment, a sensor for detecting an analyte is provided having an accuracy to within 0.001 pH units while in use or storage for at least 8 years. In another embodiment, a sensor for detecting an analyte is provided having an accuracy to within 0.001 pH units while in use or storage for at least 10 years. In some embodiments, sensors can retain their accuracy while in storage without the need for calibration of re-calibration. Such sensors can include redox-active moieties, as described herein.

In an embodiment, a sensor for detecting an analyte is provided having an accuracy to within 0.0001, or 0.001, or 0.01, or 0.1 pH units while in use or storage for at least 1 year. In another embodiment, a sensor for detecting an analyte is provided having an accuracy to within 0.0001, or 0.001, or 0.01, or 0.1 pH units while in use or storage for at least 2 years. In another embodiment, a sensor for detecting an analyte is provided having an accuracy to within 0.0001, or 0.001, or 0.01, or 0.1 pH units while in use or storage for at least 4 years. In another embodiment, a sensor for detecting an analyte is provided having an accuracy to within 0.0001, or 0.001, or 0.01, or 0.1 pH units while in use or storage for at least 8 years. In another embodiment, a sensor for detecting an analyte is provided having an accuracy to within 0.0001, or 0.001, or 0.01, or 0.1 pH units while in use or storage for at least 10 years. Such sensors can include redox-active moieties, as described herein.

In an embodiment, a redox-active moiety-containing analyte sensor is provided having a shelf life of at least about 1 month, or 2 months, or 3 months, or 4 months, or 5 months, or 6 months, or 7 months, or 8 months, or 9 months, or 10 months, or 11 months, or 1 year, or 2 years, or 3 years, or 4 years, or 5 years, or 6 years, or 7 years, or 8 years, or 9 years, or 10 years, and an accuracy to within about 0.01%, or 0.02%, or 0.03%, or 0.04%, or 0.05%, or 0.1%, or 0.15%, or 0.2%. In another embodiment, a redox-active moiety-containing analyte sensor is provided having a shelf life of at least about 1 month, or 2 months, or 3 months, or 4 months, or 5 months, or 6 months, or 7 months, or 8 months, or 9 months, or months, or 11 months, or 1 year, or 2 years, or 3 years, or 4 years, or 5 years, or 6 years, or 7 years, or 8 years, or 9 years, or 10 years, and an accuracy to within about 0.0001 pH units, or 0.0002 pH units, or 0.0003 pH units, or 0.0004 pH units, or 0.0005 pH units, or 0.0006 pH units, or 0.0007 pH units, or 0.0008 pH units, or 0.0009 pH units, or 0.001 pH units, or 0.002 pH units, or 0.003 pH units, or 0.004 pH units, or 0.005 pH units, or 0.006 pH units, or 0.007 pH units, or 0.008 pH units, or 0.009 pH units, or 0.01 pH units, or 0.02 pH units, or 0.03 pH units, or 0.04 pH units, or 0.05 pH units, or 0.06 pH units, or 0.07 pH units, or 0.08 pH units, or 0.09 pH units, or 0.1 pH units. Such sensors can include redox-active moieties, as described herein.

In an embodiment, a redox-active moiety-containing analyte sensor is provided that can be used to measure the presence or absence (or concentration) or an analyte, without re-calibration, for at least about 1 day, or 1 week, or 2 weeks, or 1 month, or 2 months, or 3 months, or 4 months, or 5 months, or 6 months, or 7 months, or 8 months, or 9 months, or 10 months, or 11 months, or 1 year, or 2 years, or 3 years, or 4 years, or 5 years, or 6 years, or 7 years, or 8 years, or 9 years, or 10 years, at an accuracy to within about 0.01%, or 0.02%, or 0.03%, or 0.04%, or 0.05%, or 0.1%, or 0.15%, or 0.2%. In some cases, the accuracy is to within about 10%, or 5%, or 1%, or 0.1%, or 0.01%, or 0.01%, or 0.001%. In another embodiment, a redox-active moiety-containing analyte sensor is provided that can be used to measure the presence or absence (or concentration) of an analyte, without re-calibration, for at least about 1 day, or 1 week, or 2 weeks, or 1 month, or 2 months, or 3 months, or 4 months, or 5 months, or 6 months, or 7 months, or 8 months, or 9 months, or 10 months, or 11 months, or 1 year, or 2 years, or 3 years, or 4 years, or 5 years, or 6 years, or 7 years, or 8 years, or 9 years, or 10 years, and an accuracy to within about 0.0001 pH units, or 0.0002 pH units, or 0.0003 pH units, or 0.0004 pH units, or 0.0005 pH units, or 0.0006 pH units, or 0.0007 pH units, or 0.0008 pH units, or 0.0009 pH units, or 0.001 pH units, or 0.002 pH units, or 0.003 pH units, or 0.004 pH units, or 0.005 pH units, or 0.006 pH units, or 0.007 pH units, or 0.008 pH units, or 0.009 pH units, or 0.01 pH units, or 0.02 pH units, or 0.03 pH units, or 0.04 pH units, or 0.05 pH units, or 0.06 pH units, or 0.07 pH units, or 0.08 pH units, or 0.09 pH units, or 0.1 pH units. Such sensors can include redox-active moieties, as described herein.

In some embodiments, a method for detecting the presence or absence of an analyte, comprises bringing an analyte sensor in contact with a sample, said analyte sensor having an electrode having immobilized thereon a redox-active moiety, wherein the redox-active moiety exhibits an oxidation potential and/or a reduction potential that is sensitive to the presence of said analyte. Next, with the aid of the analyte sensor, the analyte is detected to an accuracy of within about 20% without re-calibration for a period of at least about 1 day. In some cases the accuracy can be to within about 10%, or 5%, or 1%, or 0.1%, or 0.01%, or 0.01%, or 0.001%. In some embodiments, the analyte sensor can detect the presence or absence of the analyte without re-calibration for a time period of at least about 1 day, or 1 week, or 2 weeks, or 1 month, or 2 months, or 3 months, or 4 months, or 5 months, or 6 months, or 7 months, or 8 months, or 9 months, or 10 months, or 11 months, or 1 year, or 2 years, or 3 years, or 4 years, or 5 years, or 6 years, or 7 years, or 8 years, or 9 years, or 10 years.

Electrochemical Sensors with Multiple Sensor Modules

In another aspect of the invention, electrochemical sensors are provided having a plurality of sensor modules, each sensor module configured to measure an analyte of interest. In an embodiment, an electrochemical sensor comprises at least 2, or 3, or 4, or 5, or 6, or 7, or 8, or 9, or 10, or 15, or 20, or 25, or 30, or 35, or 40, or 45, or 50, or 100 modules. In another embodiment, an electrochemical sensor comprises a plurality of modules. The modules can be configured to detect (or measure) the presence of the same analyte (e.g., H+) or different analytes (e.g., H+ and $O_2$).

Figure 22A:
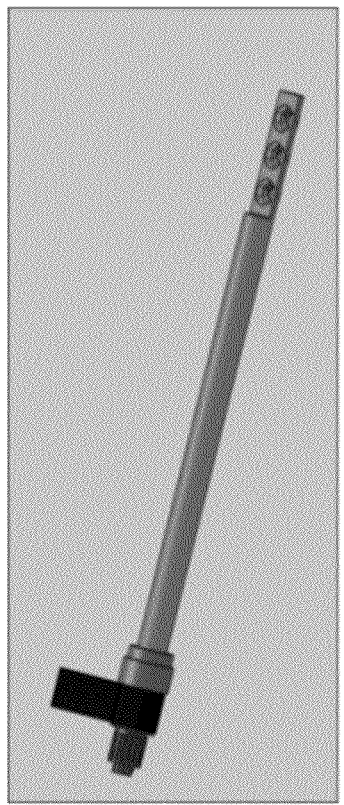
FIG. 22A schematically illustrates an electrochemical sensor having three modules.
Figure 22B:
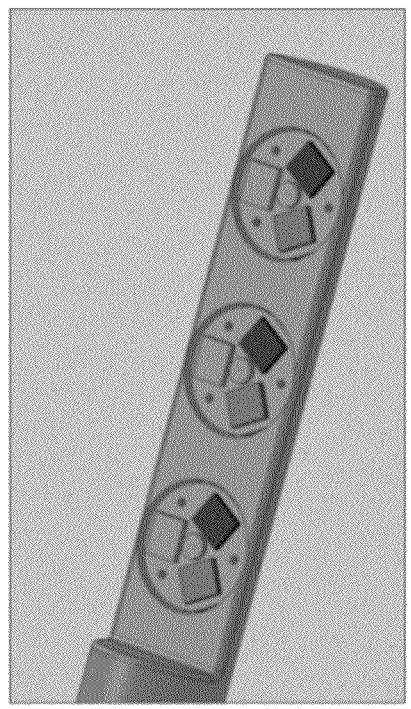
FIG. 22B is an enlarged view of a portion of the electrochemical sensor of FIG. 22A, in accordance with an embodiment of the invention.

With reference to FIG. 22A, an electrochemical sensor having three modules, wherein each module is configured to sense an analyte of interest, is illustrated, in accordance with an embodiment of the invention. The electrochemical sensor comprises a probe body that can be cylindrical in shape. FIG. 22B is an enlarged view of a portion of the electrochemical sensor of FIG. 22A, illustrating three modules configured to sense (or measure the presence of) one or more analytes of interest. Each of the three modules can be configured to sense the same analyte (e.g., H+) or different analytes. For example, a first module can be configured to sense (and measure the concentration of) H+, a second module can be configured to sense $O_2$, and a third module can be configured to sense $NH_3$. Such "multi-modal" sensor can be advantageous for use in chemical reactors and bioreactors, where the measurement of multiple analytes is desirable.

Electrochemical Sensors Formed on Printed Circuit Boards

Figure 23:
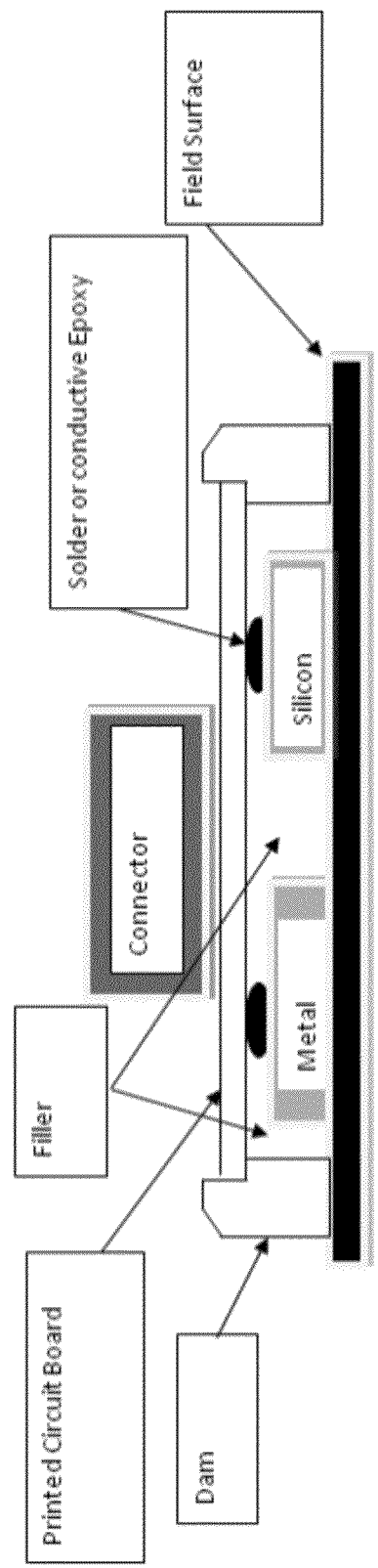
FIG. 23 schematically illustrates a printed circuit board, in accordance with an embodiment of the invention.

In another aspect of the invention, electrochemical sensors formed on circuit boards are provided. With reference to FIG. 23, In an embodiment, a printed circuit board is provided. A dam can be placed on a field that fits around the printed circuit board. The field provides a support surface that can be free of contaminants. The dam can constrain the area between the field and the printed circuit board. A filler material ("filler") can be injected through holes in the printed circuit board. The filler can hold the electrodes in place and exclude fluids from touching the back side of the electrodes and the traces of the printed circuit board. The filler can then be cured. Following curing, the sensor can be removed from the field and mounted into an appropriate holder, such as a probe body (see FIG. 22A).

Sensors formed on printed circuit boards can be mounted in a wide array of form factors. For example, they can be placed in high density polyethylene hubs and welded into disposable polyethylene containers. As another example, they can be mounted within tube walls or at the entrance and egress of columns. Such tubes walls or columns can be configured for use with containers having dimensions (e.g., diameters, lengths) configured for use with glass probe electrochemical (e.g., pH measurement) systems.

Figure 24:
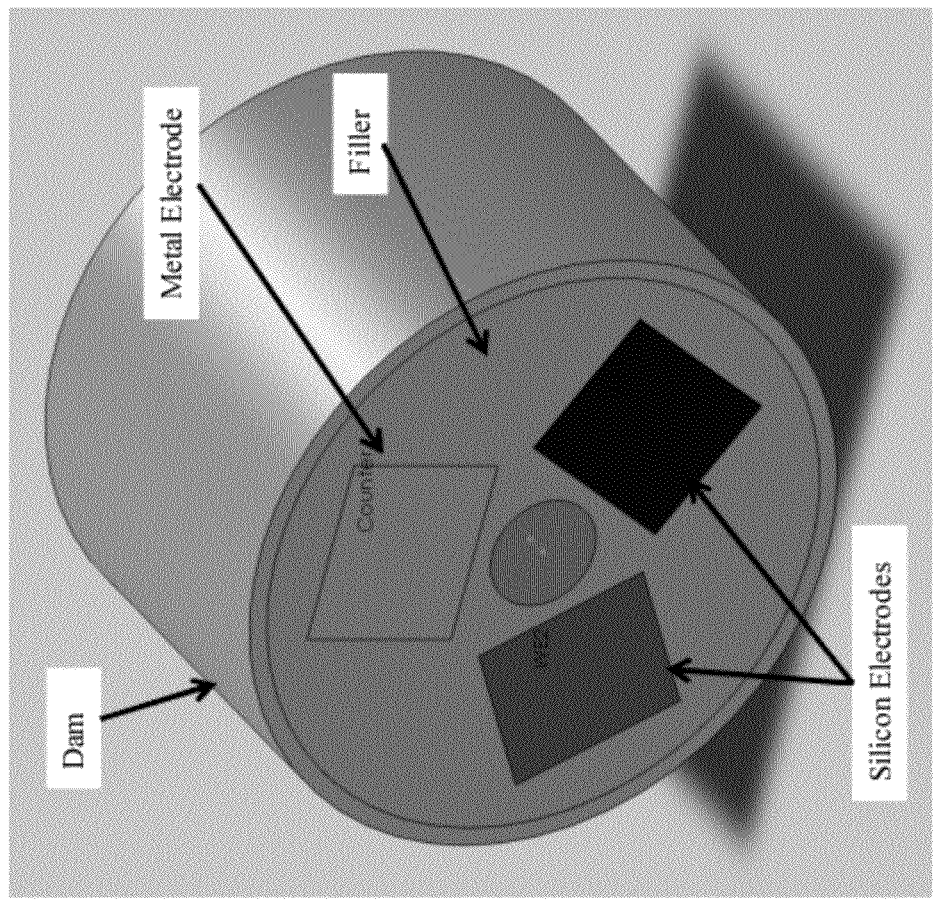
FIG. 24 schematically illustrates a sensor formed on a printed circuit board and mounted on a head assembly, in accordance with an embodiment of the invention.

With reference to FIG. 24, In an embodiment, a sensor formed on a printed circuit board can be mounted on a head assembly. Such head assembly can be configured to be mounted on a tube assembly or column, such as the tip of a tube assembly or column. In another embodiment, a head assembly can be removably mounted to a tube assembly or column. In another embodiment, a head assembly can be irremovably mounted to a tube assembly or column. In another embodiment, a head assembly can be mounted to a top portion of a tube or column for insertion into a solution having an analyte of interest. A protective material is applied around the head assembly to prevent the solution from entering a back portion of the head assembly. In an embodiment, the protective material includes one or more of polyurethane and an epoxy (e.g., polyexpoxide).

With continued reference to FIG. 24, the sensor includes a surface configured to come in contact with a solution having one or more analytes. The sensor includes a counter electrode (top) and a reference electrode (center). The sensor further includes working electrodes (bottom left and bottom right). One working electrode comprises a semiconductor surface that has immobilized thereon a redox active moiety whose oxidation potential and/or reduction potential is sensitive to the presence of the analyte, and a second working electrode comprises redox active moiety whose oxidation potential and/or reduction potential is insensitive to the presence of the analyte (see above).

Electrochemical Sensors for Use with Containers and Flow-Through Containers

In another aspect of the invention, an electrochemical sensor, such as any sensor provided herein can be used with containers and reactors such as disposable containers and reactors. In an embodiment, an electrochemical sensor is provided for use with a disposable flow-through container. In another embodiment, an electrochemical sensor is provided for use with a disposable reactor. In another embodiment, an electrochemical sensor is provided for use with a disposable plug flow reactor. In another embodiment, an electrochemical sensor is provided for use with a disposable continuous stirred tank reactor (CSTR).

In some embodiments, any electrochemical sensor ("sensor") provided herein can be configured for use with a container, including a flexible container. In an embodiment, a sensor is provided configured for use with a disposable flexible container. Such flexible container can have walls formed of a polymeric material.

With reference to FIG. 25A, an electrochemical sensor is shown mounted on a wall of a container, in accordance with an embodiment of the invention. The container can be a disposable container. The electrochemical sensor comprises a printed circuit board having thereon a counter electrode, a reference electrode and one or more working electrode (one working electrode illustrated in the cross-sectional cutaway). The printed circuit board brings the electrodes in electrical communication with connectors, which can be used to interface with a computer system or device for use with the electrochemical sensor. The electrochemical sensor is mounted on a holder flange, which is separated from the printed circuit board through a separation member, such as a damn-to-holder ring ("O-Ring", as illustrated). The probe holder can seal to the dam. The flange of the holder can be substantially thin so that it can be welded to a container, such as a bag. In an embodiment, a portion of the container is mounted to the holder flange with the aid of an adhesive, such as, for example, one or more of polyurethane and an epoxy (e.g., polyepoxide). In another embodiment, a portion of the container is welded to the holder flange. In another embodiment, the electrochemical sensor can be sterilized, such as with the aid of sterilizing chemicals, ultraviolet light irradiation, or plasma treatment.

Figure 25B:
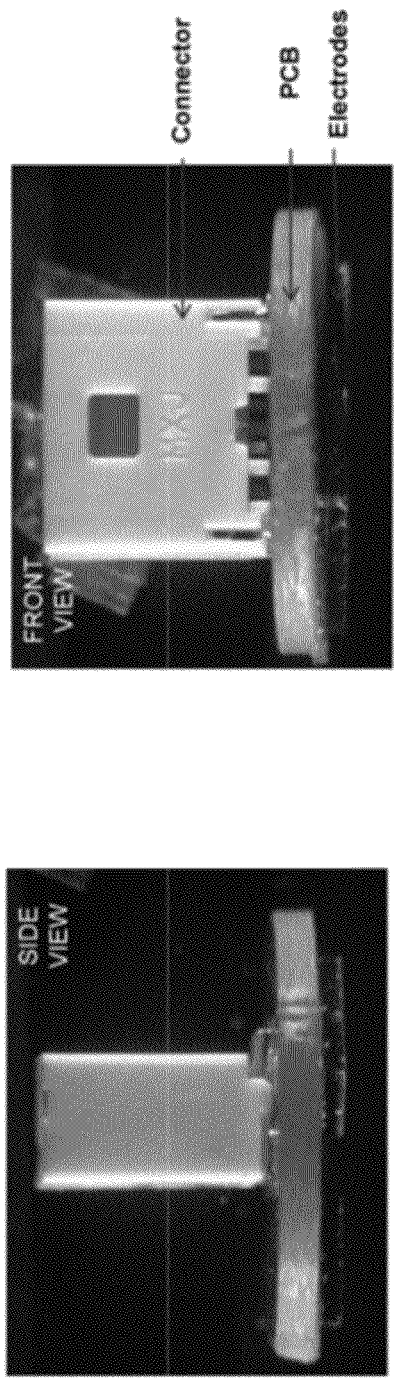
FIG. 25B illustrates an electrochemical sensor comprising electrodes formed on a printed circuit board, in accordance with an embodiment of the invention.

With reference to FIG. 25B, an electrochemical sensor is shown formed on a printer circuit board (PCB). The electrochemical sensor further includes a connector for providing a connection between the electrochemical sensor and a reader or other electronics unit, such as a voltage sync (see FIGS. 27A and 27B). The electrodes of the electrochemical sensor are disposed at a bottom portion of the PCB. In an embodiment, the electrodes of the electrochemical sensor, including working electrodes, a counter electrode and reference electrode, are formed in the PCB.

In an embodiment, the PCB can be formed of a military standard PCB board (e.g., FR4 substrate) or any PC board constructed from a non-conductive material, with conductive traces. The boards can be multilayered.

In various embodiments, solutions to seal or hermetically seal (also "sealing solutions" herein) sensor components are provided. In an embodiment, sealing solutions can comply with biological manufacturing standards, such as reducing, if not eliminating, outgassing, and avoiding the use of environmentally hazardous or toxic materials. In an embodiment, a sealing solution is provided to a sensor through the potting technique, or the application of a liquid adhesive to prevent water and other liquids from entering the sensor and causing electrical short circuits. In an embodiment, a PCB having sensor components is mounted to a tube. An interior portion of the tube is sealed from the external environment with the aid of a sealing solution around the PCB.

Figure 26:
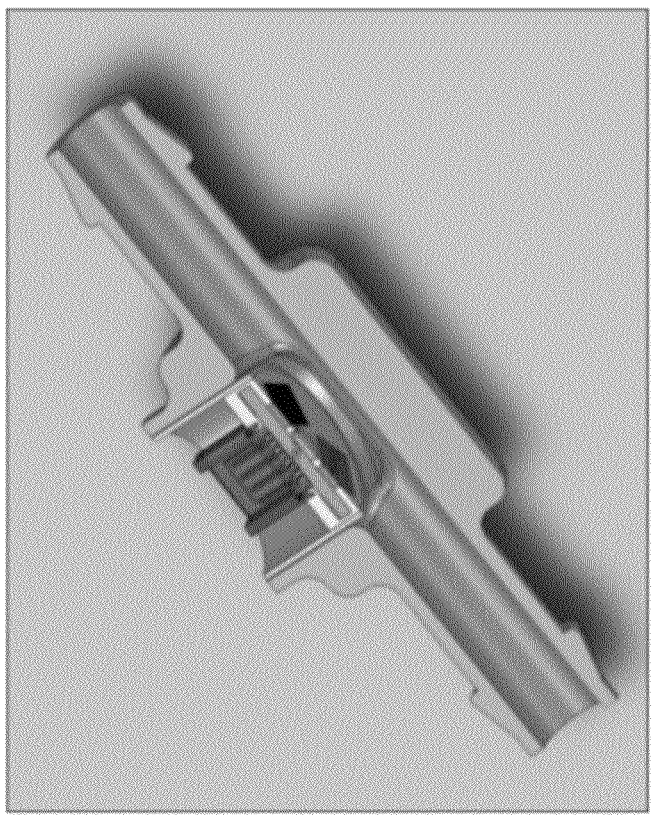
FIG. 26 schematically illustrates an electrochemical sensor mounted on a chamber of a flow-through tube, in accordance with an embodiment of the invention.

In another aspect of the invention, electrochemical sensors are provided for use with fluid flow channels, such as flow-through tubes or pipes. With reference to FIG. 26, an electrochemical sensor, such as the sensor discussed in the context of FIG. 25A, is mounted in a chamber of a flow-through tube. The chamber can be configured for mating with a flange portion of the electrochemical sensor. In an embodiment, the electrochemical sensor can be welded to the chamber. In another embodiment, the electrochemical sensor can be attached to the chamber with the aid of an epoxy, for example. In another embodiment, the electrochemical sensor can be removably attached to the chamber. In another embodiment, the electrochemical sensor can be irremovably attached to the chamber.

Electrochemical Sensor Electrical Components

In some embodiments, the sensor or holder can have on-board electronic memory, such as Electrically Erasable Programmable Read-Only Memory ("EEPROM"). The EEPROM can hold or store various items (or information) that can pair the electrochemical sensor with drive electronics. In an embodiment, the EEPROM can hold a serial number of the electrochemical sensor. In another embodiment, probe calibration parameters (e.g., probe calibration constants) can be held in the memory of the EEPROM. In another embodiment, the algorithm details of the electrochemical sensor can be held in the EEPROM.

In an embodiment, the EEPROM is provided on a printed circuit board having the various electrodes of the electrochemical sensor (e.g., pH sensor). In another embodiment, the EEPROM is provided adjacent a printed circuit board or other device having the various electrodes of the electrochemical sensor.

An electrochemical sensor comprising an on-board EEPROM can have various advantages and benefits over other electrochemical sensors. For example, an electrochemical sensor having an on-board EEPROM can be electrically optimized for different uses or markets. As an example a probe can be optimized for pH near pH 7 and only scan for a small region around pH 7. An identical probe could be optimized for pH 4 and only scan an area around pH 4. A sensor optimized for pH 4 measurement and a sensor optimized for pH 7 measurements can be similar, if not identical in form and function, different only the algorithm provided in the EEPROM of each sensor.

An EEPROM on-board an electrochemical sensor can save or hold one or more types of information. In an embodiment, the EEPROM can hold a counter for measuring (and storing) the length time an electrochemical device has been used. In another embodiment, if an electrochemical sensor is configured for use over a certain time period, the counter can enable the electrochemical sensor to stop functioning after the time period has been reached. The EEPROM can be used in conjunction with (or to facilitate) single-use functionality, as described in certain embodiments (see above). For example, if the electrochemical sensor is configured for use over the period of 28 days, the electrochemical sensor can stop functioning once the 28-day time period has elapsed. In another embodiment, the counter can enable a user to know how much time the user has remaining to use the sensor. In an embodiment, as the sensor is used, a write once area in the EEPROM can be incremented, and when this area of the EEPROM is filled, it will signal that the useful life of the sensor is finished, and the sensor will terminate use. In another embodiment, once the useful life of the sensor has finished, the user may be prevented from using the sensor.

In another embodiment, the EEPROM can transmit its serial number or other identifying information, in addition to the time remaining for the electrochemical sensor, to a data recorder that can monitor one or more sensors in a user's operation.

Alternatively, sensor calibration parameters can be stored on a remote computer system (e.g., the "cloud"), such as a server, and transmitted to a system in electrical communication with the sensor.

In some situations, a sensor can include an identification member, such as radio-frequency identification (RFID) tag, to enable a system communicating with the sensor to identify the sensor and determine, for example, any calibration parameters that may be required by the sensor. The identification member can be on a body or housing of the sensor. Calibration parameters may be specific to a particular application (e.g., pH measurements) of the sensor. The identification member can enable the system to provide proper calibration parameters, as may be required for a particular sensor application.

Electronics Components for Integration into Third-Party Systems

In another aspect of the invention, an electronics component is provided for emulating various features of current third-party or traditional electrochemical sensors. Such electronics components can advantageously permit the integration of electrochemical sensors provided herein into various current or traditional systems, such as glass probe systems.

Many laboratories and manufacturing facilities have existing third party pH meters, either stand alone or within digital control units. In some embodiments, an electronics unit is provided for integration into existing third party pH meters and systems, such as analog pH meters and systems. In an embodiment, the electronics unit can do one or more of emulating the functionality of a potentiostat, providing power the electrochemical sensor, and communicating with a third party pH meter to provide the user with a direct pH readout.

In an embodiment, the electronics unit enables communication between a third-party reader (or meter) and any probe provided herein. The electronics unit can further provide power to the probe. In an embodiment, the electronics unit includes a power input for providing power to one or more of the electronics unit and a probe in electrical communication with the electronics unit, an input from the probe, and an output to a reader.

Figure 27A:
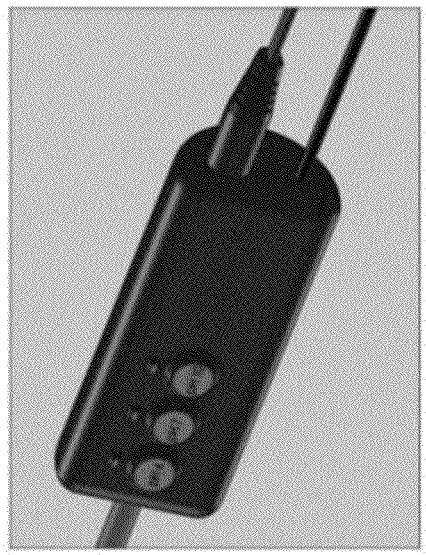
FIG. 27A schematically illustrates an electronics unit for permitting integration of an electrochemical sensor into current probe systems, in accordance with an embodiment of the invention.

With reference to FIG. 27A, an electronic unit is shown, in accordance with an embodiment of the invention. The electronic unit, which is illustrated as an electrical box, can permit integration of electrochemical sensors provided herein into systems, including electronics components, configured for use with types of electrochemical systems. With continued reference to FIG. 27A, the electrical box can be connected to a sensor on one side and a traditional readout unit or device on the other side. In at least some embodiments, electrochemical sensors are provided that use microprocessors to control transmitter electronics to scan the sensor appropriately. The electronics component evaluates the sensor signals and determines the appropriate sensor value (pH value in this case). The electronics component then takes the sensor value and computes the appropriate output voltage or current to emulate the traditional sensor. The electronics component will then transmit the appropriate output voltage to a system or device configured for use with a traditional sensor, such as a glass probe sensor.

In some embodiments, the electronic unit of FIG. 27A can transform a digital signal into a signal that is readable by a third-party system, such as a system configured for use with a glass electrode. In an embodiment, the electronic unit can emulate the glass electrode output. The electronic unit can advantageously make sensors provided herein compatible with all or substantially all third party electrochemical sensors, including pH sensors.

In an embodiment, an electronics unit is provided for integrating semiconductor-based electrochemical sensors, such as those provided herein, in devices configured for use with traditional probes, such as glass probes (e.g., glass pH probes). In another embodiment, an electronics unit is provided that is a digital to analog converter. Such an electronics unit can be configured to enable electrochemical sensors of embodiments to be used with traditional or current analog probe systems.

Traditional pH meters can have complex calibration systems for setting the voltage slope and offset of a glass pH probe. In an embodiment, a voltage sync is provided that resets a third-party pH meter. With reference to FIG. 27A, the electronics unit includes three buttons to permit the electronics unit to emulate the three point calibration for certain probe systems, which is standard prior to data collection with an analog pH meter. The electronics unit of FIG. 27A includes three buttons, each button configured to enable the electronic unit to output to an electronic system (for use with a traditional prove) a voltage value that is recognizable by the electronic system. For example, the button marked pH 7 (middle button) can sets the voltage output of the transmitter to about zero volts. The button marked pH 4 (left button) can set the voltage to about +0.177 V (or any other voltage corresponding to pH 4 for the traditional electronics system). The button marked pH 10 (right button) can set the voltage to about −0.177 V (or any other voltage corresponding to pH 10 for the traditional electronics system). This way a pH meter that was calibrated to a particular glass pH probe can be returned to the ideal slope and offset.

With continued reference to FIG. 27A, the electronic unit includes one cable or corrector for interfacing with electrochemical sensors provided herein (left cable), another connector for interfacing with a traditional electronics unit (right-top cable), such as an electronics unit configured for use with glass probe electrochemical sensors (e.g., pH sensors), and another connector (right-bottom cable) for providing power to the electrochemical sensor.

While in certain embodiments a stand-alone electronics units is provided, in other embodiments, the electronics units can be included on-board the printed circuit board having the electrochemical sensor (see FIGS. 23 and 24).

Figure 27B:
FIG. 27B illustrates a probe attached to the electronics unit of FIG. 27A, in accordance with an embodiment of the invention.

FIG. 27B illustrates the electronic unit of FIG. 27A attached to (or electrical communication with) a probe, in accordance with an embodiment of the invention. The probe can be any probe described herein, such as, for example, the probe of FIG. 1B. The probe comprises a cylindrical body and a head portion. The head portion can include one or more working electrodes, a reference electrode and a counter electrode, as described herein. The head portion is configured to come in contact with a solution having one or more analytes of interest, such as, e.g., hydrogen ions (H+).

FIG. 27C shows a system having a probe attached to an electronics unit, such as the electronics unit of FIG. 27A, in accordance with an embodiment of the invention. The system further includes a reader (or meter) for providing sensor measurements, such as pH measurements. In an embodiment, the reader is a digital reader. In another embodiment, the electronic unit can be configured for enabling communication between a reader, such as a third-party reader, and the probe. The third-party reader can be configured for use with glass probe electrochemical sensors, such as glass probe pH sensors.

In an embodiment, the electronics unit can be configured for wireless communication with a probe. In another embodiment, the electronics unit can include one or more of a WiFi transmitter, a Bluetooth transmitter, a radiofrequency transmitter and an infrared (1R) transmitter for communicating with the probe.

Electronics Components for Communicating with External Devices

Another aspect of the invention provides an electrochemical sensor, such as an electrochemical sensor on a printed circuit board, which includes a transmitter for wirelessly transmitting information to a system configured to collect information from the electrochemical sensor. The transmitter can be reduced in size so that it can be included in the sensor (or probe). The transmitter can be configured to interface with a receiver on a system configured to communicate with the electrochemical sensor. In an embodiment, the electrochemical sensor can be configured for WiFi transmission. In another embodiment, the electrochemical sensor can be configured for Bluetooth transmission. In another embodiment, the electrochemical sensor can be configured for radiofrequency (RF) transmission. In another embodiment, the electrochemical sensor can be configured for infrared transmission. In another embodiment, the electrochemical sensor can be configured for inductive transmission (i.e., inductively coupling). In another embodiment, the electrochemical sensor can be configured for optical (e.g., fiber optic) transmission.

In some embodiments, a transmitter is provided that is powered by an energy storage device; such as a battery (e.g., lithium ion battery) or a photovoltaic (solar) cell. The energy storage device can be configured to provide power to the transmitter over the life of the electrochemical sensor. In an embodiment, the energy storage device is configured to provide power to both the transmitter and the electrochemical sensor, such as any electrochemical sensor provided herein. In another embodiment, the transmitter can be an on-board transmitter. For example, the electrochemical sensor of FIG. 24, configured to be mounted at a tip of a probe assembly or shaft, can include a transmitter. The transmitter can include electronics that can provide a wireless link, such as a digital link (e.g., WiFi, Bluetooth) to a computer system. This link can be done with WiFi, Bluetooth or other radio communications protocols, such as radiofrequency (RF) protocols.

An electrochemical sensor configured for wireless transmission can be used in numerous contexts. In an embodiment, an electrochemical sensor configured for wireless transmission can be configure to transmit sensor data from remote and hard-to-reach locations, such as providing data from inside oil wells, the human body (e.g., providing the concentrations of various analytes, such as pH) and high pressure settings, such as chemical reactors.

In another embodiment, an electronics component is provided that can be configured to provide a digital signal that can be read using a computing device, such as a personal computer (PC) or a mobile electronics device, such as an Apple® iPad® or iPod®, an Android®-enabled device, a Smart Phone, a netbook, a laptop, a tablet PC, or a slate PC.

In an embodiment, a graphical user interface ("GUI") can provide a user a sensor reading, such as at a fixed point in time or as a function of time. In an embodiment, the GUI can provide a user a sensor reading (e.g., pH reading) at least every 0.1 seconds, or 0.2 seconds, or 0.3 seconds, or 0.4 seconds, or 0.5 seconds, or 0.6 seconds, or 0.7 seconds, or 0.8 seconds, or 0.9 seconds, or 1 second, or 1.1 seconds, or 1.2 seconds, or 1.3 seconds, or 1.4 seconds, or 1.5 seconds, or 1.6 seconds, or 1.7 seconds, or 1.8 seconds, or 1.9 seconds, or 2 seconds, or 2.1 seconds, or 2.2 seconds, or 2.3 seconds, or 2.4 seconds, or 2.5 seconds, or 2.6 seconds, or 2.7 seconds, or 2.8 seconds, or 2.9 seconds, or 3 seconds, or 3.1 seconds, or 3.2 seconds, or 3.3 seconds, or 3.4 seconds, or 3.5 seconds, or 3.6 seconds, or 3.7 seconds, or 3.8 seconds, or 3.9 seconds, or 4 seconds, or 4.1 seconds, or 4.2 seconds, or 4.3 seconds, or 4.4 seconds, or 4.5 seconds, or 4.6 seconds, or 4.7 seconds, or 4.8 seconds, or 4.9 seconds, or 5 seconds, or 5.1 seconds, or 5.2 seconds, or 5.3 seconds, or 5.4 seconds, or 5.5 seconds, or 5.6 seconds, or 5.7 seconds, or 5.8 seconds, or 5.9 seconds, or 6 seconds, or 6.1 seconds, or 6.2 seconds, or 6.3 seconds, or 6.4 seconds, or 6.5 seconds, or 6.6 seconds, or 6.7 seconds, or 6.8 seconds, or 6.9 seconds, or 7 seconds, or 7.1 seconds, or 7.2 seconds, or 7.3 seconds, or 7.4 seconds, or 7.5 seconds, or 7.6 seconds, or 7.7 seconds, or 7.8 seconds, or 7.9 seconds, or 8 seconds, or 8.1 seconds, or 8.2 seconds, or 8.3 seconds, or 8.4 seconds, or 8.5 seconds, or 8.6 seconds, or 8.7 seconds, or 8.8 seconds, or 8.9 seconds, or 9 seconds, or 9.1 seconds, or 9.2 seconds, or 9.3 seconds, or 9.4 seconds, or 9.5 seconds, or 9.6 seconds, or 9.7 seconds, or 9.8 seconds, or 9.9 seconds, or 10 seconds, or 10.1 seconds, or 10.2 seconds, or 10.3 seconds, or 10.4 seconds, or 10.5 seconds, or 10.6 seconds, or 10.7 seconds, or 10.8 seconds, or 10.9 seconds, or 11 seconds, or 11.1 seconds, or 11.2 seconds, or 11.3 seconds, or 11.4 seconds, or 11.5 seconds, or 11.6 seconds, or 11.7 seconds, or 11.8 seconds, or 11.9 seconds, or 12 seconds, or 12.1 seconds, or 12.2 seconds, or 12.3 seconds, or 12.4 seconds, or 12.5 seconds, or 12.6 seconds, or 12.7 seconds, or 12.8 seconds, or 12.9 seconds, or 13 seconds, or 13.1 seconds, or 13.2 seconds, or 13.3 seconds, or 13.4 seconds, or 13.5 seconds, or 13.6 seconds, or 13.7 seconds, or 13.8 seconds, or 13.9 seconds, or 14 seconds, or 14.1 seconds, or 14.2 seconds, or 14.3 seconds, or 14.4 seconds, or 14.5 seconds, or 14.6 seconds, or 14.7 seconds, or 14.8 seconds, or 14.9 seconds, or 15 seconds, or 15.1 seconds, or 15.2 seconds, or 15.3 seconds, or 15.4 seconds, or 15.5 seconds, or 15.6 seconds, or 15.7 seconds, or 15.8 seconds, or 15.9 seconds, or 16 seconds, or 16.1 seconds, or 16.2 seconds, or 16.3 seconds, or 16.4 seconds, or 16.5 seconds, or 16.6 seconds, or 16.7 seconds, or 16.8 seconds, or 16.9 seconds, or 17 seconds, or 17.1 seconds, or 17.2 seconds, or 17.3 seconds, or 17.4 seconds, or 17.5 seconds, or 17.6 seconds, or 17.7 seconds, or 17.8 seconds, or 17.9 seconds, or 18 seconds, or 18.1 seconds, or 18.2 seconds, or 18.3 seconds, or 18.4 seconds, or 18.5 seconds, or 18.6 seconds, or 18.7 seconds, or 18.8 seconds, or 18.9 seconds, or 19 seconds, or 19.1 seconds, or 19.2 seconds, or 19.3 seconds, or 19.4 seconds, or 19.5 seconds, or 19.6 seconds, or 19.7 seconds, or 19.8 seconds, or 19.9 seconds, or 20 seconds or 20.1 seconds, or 20.2 seconds, or 20.3 seconds, or 20.4 seconds, or 20.5 seconds, or 20.6 seconds, or 20.7 seconds, or 20.8 seconds, or 20.9 seconds, or 21 seconds, or 21.1 seconds, or 21.2 seconds, or 21.3 seconds, or 21.4 seconds, or 21.5 seconds, or 21.6 seconds, or 21.7 seconds, or 21.8 seconds, or 21.9 seconds, or 22 seconds, or 22.1 seconds, or 22.2 seconds, or 22.3 seconds, or 22.4 seconds, or 22.5 seconds, or 22.6 seconds, or 22.7 seconds, or 22.8 seconds, or 22.9 seconds, or 23 seconds, or 23.1 seconds, or 23.2 seconds, or 23.3 seconds, or 23.4 seconds, or 23.5 seconds, or 23.6 seconds, or 23.7 seconds, or 23.8 seconds, or 23.9 seconds, or 24 seconds, or 24.1 seconds, or 24.2 seconds, or 24.3 seconds, or 24.4 seconds, or 24.5 seconds, or 24.6 seconds, or 24.7 seconds, or 24.8 seconds, or 24.9 seconds, or 25 seconds, or 25.1 seconds, or 25.2 seconds, or 25.3 seconds, or 25.4 seconds, or 25.5 seconds, or 25.6 seconds, or 25.7 seconds, or 25.8 seconds, or 25.9 seconds, or 26 seconds, or 26.1 seconds, or 26.2 seconds, or 26.3 seconds, or 26.4 seconds, or 26.5 seconds, or 26.6 seconds, or 26.7 seconds, or 26.8 seconds, or 26.9 seconds, or 27 seconds, or 27.1 seconds, or 27.2 seconds, or 27.3 seconds, or 27.4 seconds, or 27.5 seconds, or 27.6 seconds, or 27.7 seconds, or 27.8 seconds, or 27.9 seconds, or 28 seconds, or 28.1 seconds, or 28.2 seconds, or 28.3 seconds, or 28.4 seconds, or 28.5 seconds, or 28.6 seconds, or 28.7 seconds, or 28.8 seconds, or 28.9 seconds, or 29 seconds, or 29.1 seconds, or 29.2 seconds, or 29.3 seconds, or 29.4 seconds, or 29.5 seconds, or 29.6 seconds, or 29.7 seconds, or 29.8 seconds, or 29.9 seconds, or 30 seconds, or 31 seconds, or 32 seconds, or 33 seconds, or 34 seconds, or 35 seconds, or 36 seconds, or 37 seconds, or 38 seconds, or 38 seconds, or 40 seconds, or 45 seconds, or 50 seconds, or 55 seconds, or 1 minute, or 2 minutes, or 3 minutes, or 4 minutes, or 5 minutes, or 6 minutes, or 7 minutes, or 8 minutes, or 9 minutes, or 10 minutes, or 20 minutes, or 30 minutes, or 1 hour, or 2 hours, or 3 hours, or 4 hours, or 5 hours, or 6 hours, or 7 hours, or 8 hours, or 9 hours, or 10 hours, or 11 hours, or 12 hours, or 1 day, or 2 days, or 3 days, or 4 days, or 5 days.

In an embodiment, the electrochemical sensor can provide a reading to a computer system coupled to (or interfaced with) the electrochemical sensor. Such a reading can be recorded in the computer's memory with a timestamp that can be assembled into a date and/or time based graph. The GUI can also record multiple sensors outputs, such as from a probe having a plurality of electrochemical sensors (see FIGS. 22A and 22B). The GUI can compile data from different sensors and provide a user an output that is calculated from the multiple sensors. In an embodiment, such output can be an average output, such as an average pH. For example, if pH measurements are being made, the curve for pH can be temperature dependent, and the system can correct the pH for temperature. The system can calculate and provide an input for the temperature and concentration of hydrogen ions.

In an embodiment, a sensor is provided having electrochemical sensors and sensors for measuring the temperature of a solution or fluid in the solution or fluid. The temperature can be the temperatures as measured in the vicinity of the sensor. In an embodiment, the sensor includes one or more thermocouples for measuring the temperature of a solution adjacent to the sensor. Such temperature measurement can be used to provide a temperature-corrected sensor output, such as a pH output corrected for temperature.

In some embodiments, a digital meter is provided that can display the readout from an electrochemical sensor. In an embodiment, the digital meter can provide real-time data. In another embodiment, the digital meter can provide date at set intervals. In such a case, data can be averaged over a certain time period that can be a function of the intervals in which data is measured and/or displayed. The digital meter can provide one or more of current, voltage, impedance, conductivity, temperature, time, time left in the lifetime of the device (e.g., if the electrochemical sensor is a time-limited device, see above), area calculations (e.g., IV area calculations) and maximum peak positions in an IV curve. A sensor trend can also be displayed. In an embodiment, the meter can communicate digitally with industrial digital control units, such as control units in coal fired power plants, steam boiler water, food and beverage manufacturing facilities, personal care products, water and wastewater, refineries, biofuel manufacturing facilities, reactors, bioreactors, oil well rigs, oil well boars, or nuclear power plants and the manufacture of radionuclide therapeutics.

Sensors for Insertion into Containers for Use with Glass Probes

Another aspect of the invention provides a sensor system comprising a redox-active moiety-containing analyte sensor for insertion into a container for use with a glass probe analyte sensor. In an embodiment, the redox-active moiety-containing analyte sensor comprises one or more redox-active moieties. In another embodiment, the redox-active moiety-containing analyte sensor comprises a redox-active moiety that is sensitive to the presence of an analyte and another redox-active moiety that is insensitive to the presence of the analyte. In another embodiment, the redox-active moiety-containing analyte sensor is disposed in a probe body having a form factor configured for insertion into a container for use with a glass probe analyte sensor.

Figure 27:
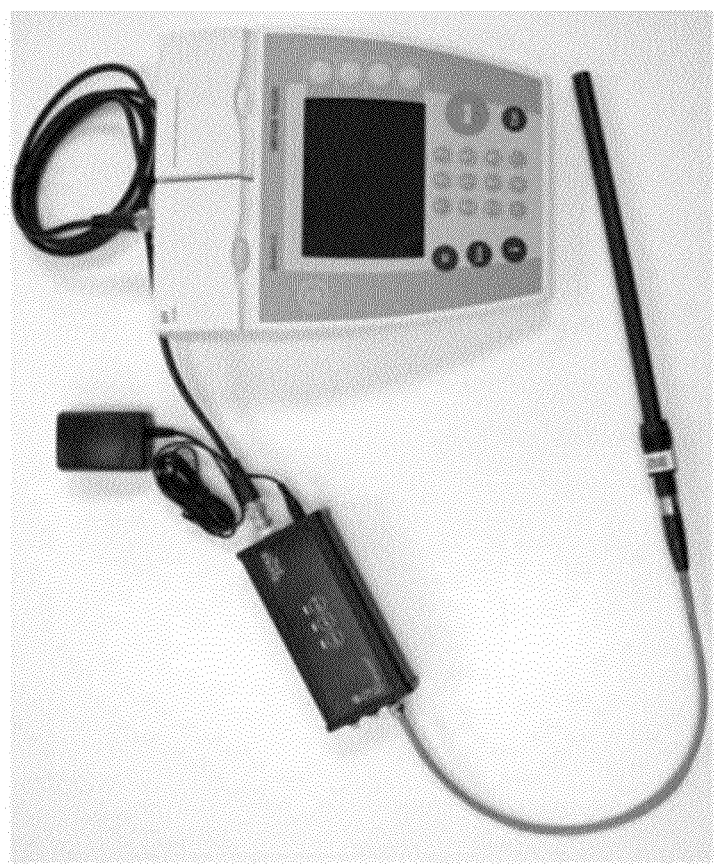
FIG. 27C shows a probe attached to an electronic unit, which is in turn attached to a reader, in accordance with an embodiment of the invention.

In an embodiment, an electrochemical sensor is provided having a sensor head, the sensor head having working, counter and reference electrodes, as described above. The sensor head can be mounted to a probe body having a shape (size and length) configured to mate with existing or traditional probe systems, such as glass probe systems. The electrochemical sensor can be interfaced with a system used to operate the traditional probe system with the aid of the electrical box described above in the context of FIG. 27.

Figure 28:
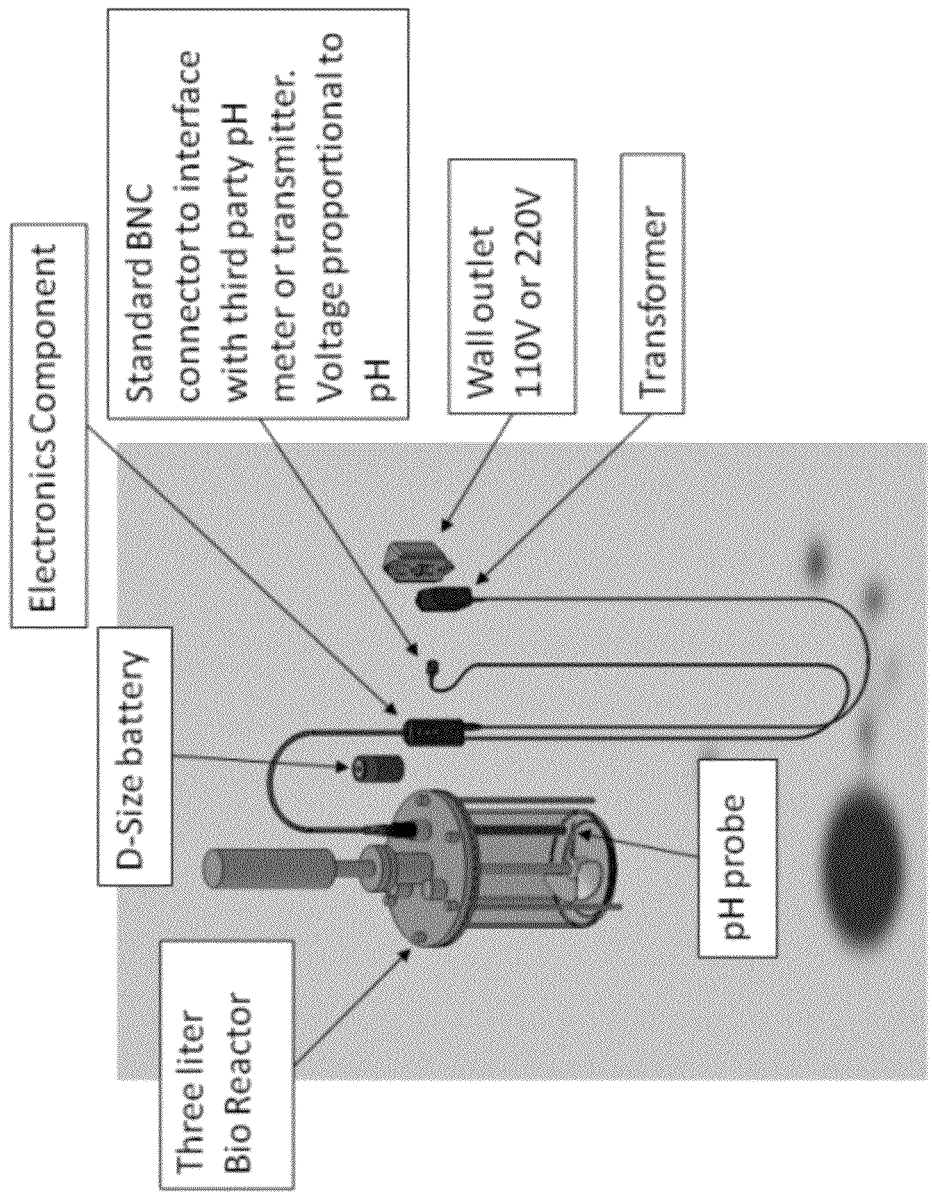
FIG. 28 schematically illustrates an electrochemical probe mounted on a bioreactor, in accordance with an embodiment of the invention.

With reference to FIG. 28, an electrochemical probe and transmitter are illustrated for use with a bioreactor, in accordance with an embodiment of the invention. The electrochemical probe is connected to an electronics component that can be used to interface the electrochemical probe with an existing (or third-party) system or device configured to communicate with (or take measurements from) a probe, such as, for example, a glass probe. The pH probe includes a probe head at a distal end of a probe body. The probe body is configured to extend into the bioreactor for taking measurements of analytes of interests (e.g., H+ for pH measurements).

In some embodiments, a sensor is provided for insertion into a container configured for use with a traditional or conventional glass probe. In an embodiment, the container is cylindrical in shape. In another embodiment, the container has a circular cross-section. In another embodiment, the container is formed of one or more metals. In another embodiment, the container is formed of one or more metals including aluminum, nickel, platinum, ruthenium, rhodium, tungsten, titanium, palladium, copper, silver, gold and iron. In another embodiment, the container is formed of one or more metals including stainless steel.

In an embodiment, an electrochemical sensor is provided having a head portion comprising one or more working electrodes, a counter electrode and a reference electrode, the head portion mounted on a body portion, such as a tubular or cylindrical body portion. The body portion can include threading configured to permit the body portion to be mounted to a bioreactor. In an embodiment, the threading includes PG-13 threading. In an embodiment, the body portion can be formed of a polymeric material. In another embodiment, the body portion can be formed of a metallic material, such as stainless steel.

Calibration

Another aspect of the invention provides a system for calibrating an electrochemical sensor with the aid of a robot. In an embodiment, a robot is provided to obtain calibration parameters, which can subsequently be provided to uses or stored in an EEPROM onboard an electrochemical sensor.

In an embodiment, a robot comprises a robot arm for placing an electrochemical sensor in a first solution or environment having a known analyte, such as a solution or environment having a known pH. The robot then measures the output of the electrochemical sensor for the particular analyte measurements and records the output, such as in a table. The robot then places the electrochemical in a second solution or environment having a known analyte, such as a solution or environment having a known pH. The robot then measures the output of the electrochemical sensor for the particular analyte measurement and records the output, such as in a table. The robot can repeat this process, as desired, until a predetermined number of measurements have been made. For example, the robot can record electrochemical sensor outputs for pH 4, pH 7 and pH 10 solutions. The robot can then record the calibration data in a calibration file for distribution to a user, or record the calibration data in a memory chip, such as a memory chip onboard the electrochemical sensor (e.g., EEPROM).

The pH sensors of the present invention are amenable to miniaturization. In an embodiment, electrochemical sensors of the present invention, such as pH sensors, can be miniaturized for use in capsules for insertion in a subject's body. In another embodiment, electrochemical sensors of the present invention, such as pH sensors, can be miniaturized for use in capsules for insertion in a subject's body. In another embodiment, electrochemical sensors of the present invention, such as pH sensors, can be miniaturized for use in skin patches applicable to a subject's body. In another embodiment, electrochemical sensors of the present invention, such as pH sensors, can be miniaturized for use a nucleic acid sequencing array (e.g., 512×512 array).

Methods and Systems for Determining pH from Voltammetric or Amperometric Data

Another aspect of the invention provides systems and methods for converting peaks in voltammetric or amperometric data to pH values. In some embodiments, a system is provided for implementing the methods provided herein. Such methods can be implemented with the aid of a system implementing an algorithm, as set forth in machine-readable code.

In an embodiment, in a first step, the system identifies all peaks having at least 10 fold greater intensity than background noise level. A peak is defined as a current maximum that is bordered by two current minimums, one minimum on each side of the maximum. In an embodiment, a maximum can be 5% higher than a local minimum. The system then ranks the maxima in terms of height (value of the current at a given voltage), from maximum height to minimum height. Next, using the largest maximum (i.e., the maximum having largest value), the system takes the positions of the local minima on each side of the largest maximum. The system then finds the equation of the line that connects the two local minima. In an embodiment, the line has the form of I=c+mV, wherein 'I' is the measured current, 'V' is the applied voltage, 'm' is the slope of the line and 'c' is the intercept. This process is repeated for each data point in the amperometric data. For a set of three data points a correction equation is provided. The system then subtracts the correction equation for each original data point, $(I_n, V_n)$. A corrected data point is then achieved, represented by $(I_{nc}, V_n)=(I_n-(c+m*V_n), V_n)$. This correction removes other phenomena from the data, such as local abnormalities due to noise.

Next, with a corrected data set, the system finds the voltage of a maximum current of interest. In an embodiment, a search for the voltage is limited to data points between two local minima, as described above. The system first finds the difference between a maximum and the minima. The system then takes the difference between the higher minima and the maximum current. In an embodiment, only the data that is above a predetermined percentage of the current range of interest is used. In an embodiment, only data that is above a 50%, or 55%, or 60%, or 65%, or 70%, or 75%, or 80%, or 85%, or 90% of the current range of interest is used. In another embodiment, only data that is from about 20% to 100% of the current range of interest is used. For example, the upper 80% of data between the higher minima and the maximum can be used. Next, the data thus generated is fit to a parabola. While a parabola can be computationally desirable, other mathematical functions can be used to fit the data. For example, the data can be fit with a Taylor Series expansion model to an order that minimizes the spread among the data points and points generated by the model. Next, the maximum of the fitted parabola (or other function) can be used as the maximum of the amperometric curve. The distance between the corrected maxima for the first working electrode (WE1) and the second working electrode (WE2) is used to determine a pH. In an embodiment, the pH can be represented by pH=c+m(WE1−WE2)+m2(WE1−WE2)$^2$+m3(WE1−WE2)$^3$, wherein 'c', 'm', 'm2' and 'm3' are constants that are determined experimentally—i.e., the constants are determined by fitting the equation to known one or more samples having known pH values).

Form Factors and Sensor Applications

Another aspect of the invention provides electrochemical sensors having form factors for use with various applications, such as insertion into a container for use with glass probe sensors. This advantageously enables a user to replace glass probe sensor with electrochemical sensors provided herein, such as redox-active moiety containing sensors.

Sensors provided herein can be suited for various applications. In some embodiments, sensors provided herein are configured for use in bioreactors, such as, e.g., single-use and/or disposable bioreactors. In other embodiments, sensors provided herein are configured for use in sample preparation and/or analytical systems, such as chromatography, including, for example, liquid chromatography (e.g., high pressure liquid chromatography), gas chromatography, affinity chromatography, supercritical fluid chromatography, ion exchange chromatography, size-exclusion chromatography, reversed phase chromatography, two-dimensional chromatography, simulated moving-bed chromatography, pyrolysis gas chromatography, fast protein liquid chromatography, countercurrent chromatography, chiral chromatography, and column chromatography. In other embodiments, sensors provided herein are configured for use in process separation unit operations, such as distillation columns and absorption columns. In other embodiments, sensors provided herein are configured for use in continuous stirred tank reactors. In other embodiments, sensors provided herein are configured for use in plug flow rectors. In other embodiments, sensors provided herein are configured for use in fluidized bed reactors.

Figure 32B:
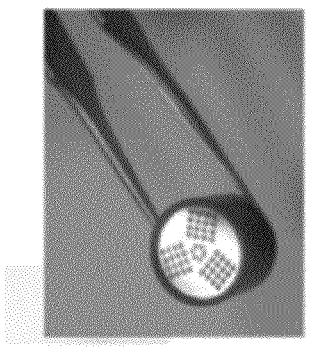
FIGS. 32A-32E show exemplary sensors having form factors suited for various applications.
Figure 32E:
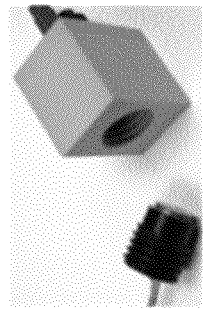
Figure 32D:
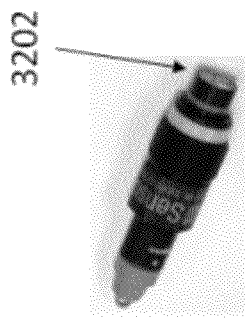
Figure 32A:
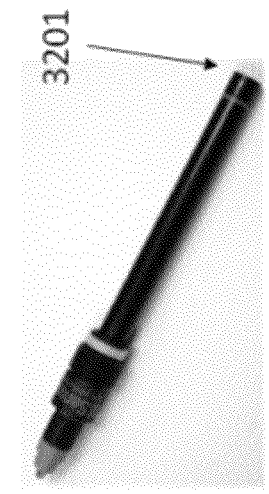
Figure 32C:
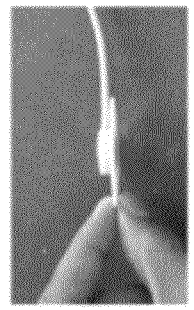

Sensors can have form factors (e.g., shapes, sizes) suited for such various sensor applications provided herein. FIGS. 32A-32E show exemplary sensors having form factors suited for various applications. FIG. 32A shows a sensor having a form factor as found in some conventional probes. A redox-active moiety containing sensor 3201 is disposed at a probe tip of the sensor of FIG. 32A. FIG. 32B shows an electrochemical sensor having a form factor that is suited for use in pH sensors. The sensor of FIG. 32B can be used at the probe tip of the sensor of FIG. 32A. FIG. 32C shows a substantially flat sensor. The sensor of FIG. 32C can be suited for use in reactors, such as bioreactors. The sensor of FIG. 32C can have a distribution of working electrodes as described herein. FIG. 32D shows a sensor configured for use with in-line flow systems, such as, for example, plug flow reactors. A redox-active moiety containing sensor 3202 is disposed at a probe tip of the sensor of FIG. 32D. FIG. 32E shows a sensor configured for use in a system having a predetermined volume, such as, e.g., about 30 microliters of retained volume.

Sensors provided herein can have supports for enabling the sensors to be used in various applications. For example, the sensors of FIGS. 32A, 32D and 32E can have threads, o-rings, and hex bodies that allow for the sensors to be mounted in various settings, such as, for example, reactors (e.g., bioreactors), various unit operations (e.g., distillation columns), flow-through systems and fermentors.

EXAMPLES

Reagents and Instrumentations

Vinylferrocene, vinylanthracene, hydrofluoric acid were purchased from Sigma-Aldrich (Sigma-Aldrich INC., USA), ferrocenecarboxaldehyde and mesitylene were obtained from Alfa Aesar (Alfa Aesar INC., USA), and 9-anthracene-carboxaldehyde was obtained from Acros Organics (Acros Organics INC. USA). All the chemicals were obtained with the highest grade available and were used without further purification.

Different single-side polished, primary flat, 500 µm thick silicon wafers with (111) and (100) orientation were purchased from Virginia Semiconductor with the following specification: i) P-type (100, 10-90 Ω-cm resistivity), ii) P-type (100, 0.001-0.005 Ω-cm resistivity), iii) N-type (100, 10-40 Ω-cm resistivity), iv) N-type (100, 0.02-0.05 Ω-cm resistivity), v) P-type (111, 0.001-0.004 Ω-cm resistivity) and vi) N-type (111, 0.001-0.005 Ω-cm resistivity).

Electrochemical measurements were recorded using an Autolab computer controlled potentiostat (Ecochemie, Utrecht, Netherlands) with a standard three-electrode configuration, consisting of a saturated calomel reference electrode (SCE, Radiometer, Copenhagen, Denmark), a platinum auxiliary electrode (Bioanalytical Systems INC., USA)) and silicon (Virginia Semiconductor INC, USA) working electrode.

Different pH solutions in the range of 1 to 12 were also prepared in deionized water as follows: pH 1.2, 0.10 M perchloric acid; pH 2.2, 0.05 M perchloric acid; pH 4.6, 0.1 M acetic acid+0.10 M sodium acetate; pH 5.6, 0.5 M sodium acetate; pH 6.5, 0.025 M $K_2PO_4$+0.025 M $KH_2PO_4$; pH 7.33, 0.05 M K$_2$PO$_4$; pH 9.3, 0.10 M sodium borate; pH 13.5, 0.1 M sodium hydroxide. These solutions also contained an addition of 0.10 M sodium perchlorate as supporting electrolyte. The pH of these solutions was measured using the SevinMulti (Mettler Toledo) pH meter.

Example 1

Preparation of H-Terminated Silicon Surface

Silicon wafers (oriented (111) or (100), cut into ca. 1×1 cm$^2$ pieces) were cleaned using "Piranha" solution (concentrated H$_2$SO$_4$:30% H$_2$O$_2$, 3:1, v/v) at about 80° C. for 30 min and rinsed thoroughly with deionized water. (In some cases, smaller pieces, e.g., 2 mm×3.3 mm or 2 mm×2.7 mm were used.) Subsequently, the wafer pieces were oxidized in H$_2$O$_2$:HCl:H$_2$O (2:1:8) at about 80° C. for 15 min, and in H$_2$O$_2$:NH$_4$OH:H$_2$O (2:1:8) at about 80° C. for another 15 min, rinsed copiously with deionized water. The cleaned Si(100) wafers pieces were then etched in 2.5% HF solution for about 15 min. These procedures eliminate the native silicon oxide layer, yielding an H-terminated surface. The H-terminated substrates were quickly rinsed with deionized water, dried with nitrogen gas and were used immediately for the derivatization experiments. The Si(100) (10-90 Ω-cm, P-type) was used for the experiments below.

Example 2

Derivatization of H-Terminated Silicon Surface with Ferrocene Moieties

Approximately 10 mmol mesitylene solution of vinylferrocene (VFc) or ferrocenecarboxaldehyde (FcA) was put in a round bottom flask and bubbled with nitrogen or argon gas for at least 30 min. A piece of the H-terminated silicon substrate was then immersed in the solution and allowed to react with VFc or FcA for about 12 h under reflux at about 150° C. in an oil bath. During the reaction, the solution was also purged with nitrogen (or argon) to eliminate dissolved oxygen and to prevent the substrate from being oxidized. After the reaction, the substrate derivatized with VFc or FcA was rinsed with dichloromethane, acetonitrile, and methanol; and dried under a stream of nitrogen gas. The derivatization of the H-terminated surface with ferrocene moieties as described in Example 2 is illustrated in FIG. 5.

Example 3

Derivatization of H-Terminated Silicon Surface with Anthracene Moieties

Approximately 10 mmol mesitylene solution of vinylanthracene (VA) or anthraldehyde (AnA) was put in a round bottom flask and bubbled with nitrogen or argon gas for at least 30 min. A piece of the H-terminated silicon substrate was then immersed in the solution and allowed to react with VA or AnA for about 12 h under reflux at about 150° C. in an oil bath. During the reaction, the solution was also purged with nitrogen (or argon) to eliminate dissolved oxygen and to prevent the substrate from being oxidized. After the reaction, the substrate derivatized with VA or AnA was rinsed with dichloromethane, acetonitrile and methanol; and dried under a stream of nitrogen gas. The derivatization of the H-terminated surface with anthracene moieties as described in Example 3 is illustrated in FIG. 6.

Example 4

Derivatization of H-Terminated Silicon Surface with Both the Anthracene and Ferrocene Moieties A 10 mmol mesitylene solution of anthracene (VA or AnA) and ferrocene (VFc or FcA) in 1:1 ratio was put in a round bottom flask and bubbled with nitrogen or argon gas for at least 30 min. A piece of the H-terminated silicon substrate was then immersed in the solution and allowed to react with the anthracene and ferrocene mixtures for about 12 hours under reflux at 150° C. in oil bath. During the reaction, the solution was also purged with nitrogen (or argon) to eliminate dissolved oxygen and to prevent the substrate from being oxidized. After the reaction, the derivatized substrate was rinsed with dichloromethane, acetonitrile and methanol, and dried under a stream of nitrogen gas. FIG. 7 illustrates a reaction in which the silicon surface derivatized with both the anthracene and ferrocene using VFc and VA.

Example 5

Electrochemical Measurements of the Derivatized Silicon Wafers in Different pH Solutions Square wave voltammetry (SWV) was carried out for the derivatized silicon wafers in a specially designed electrochemical cell as shown in FIG. 8. The electrochemical measurements were performed using a standard three-electrode configuration. In these experiments, the derivatized silicon wafers were used as the working electrode, and was exposed to different pH solutions (about 10 mL) in the electrochemical cell. SWV were performed with a frequency of 10 Hz, a step potential of 2 mV and an amplitude of 25 mV.

Figure 9:
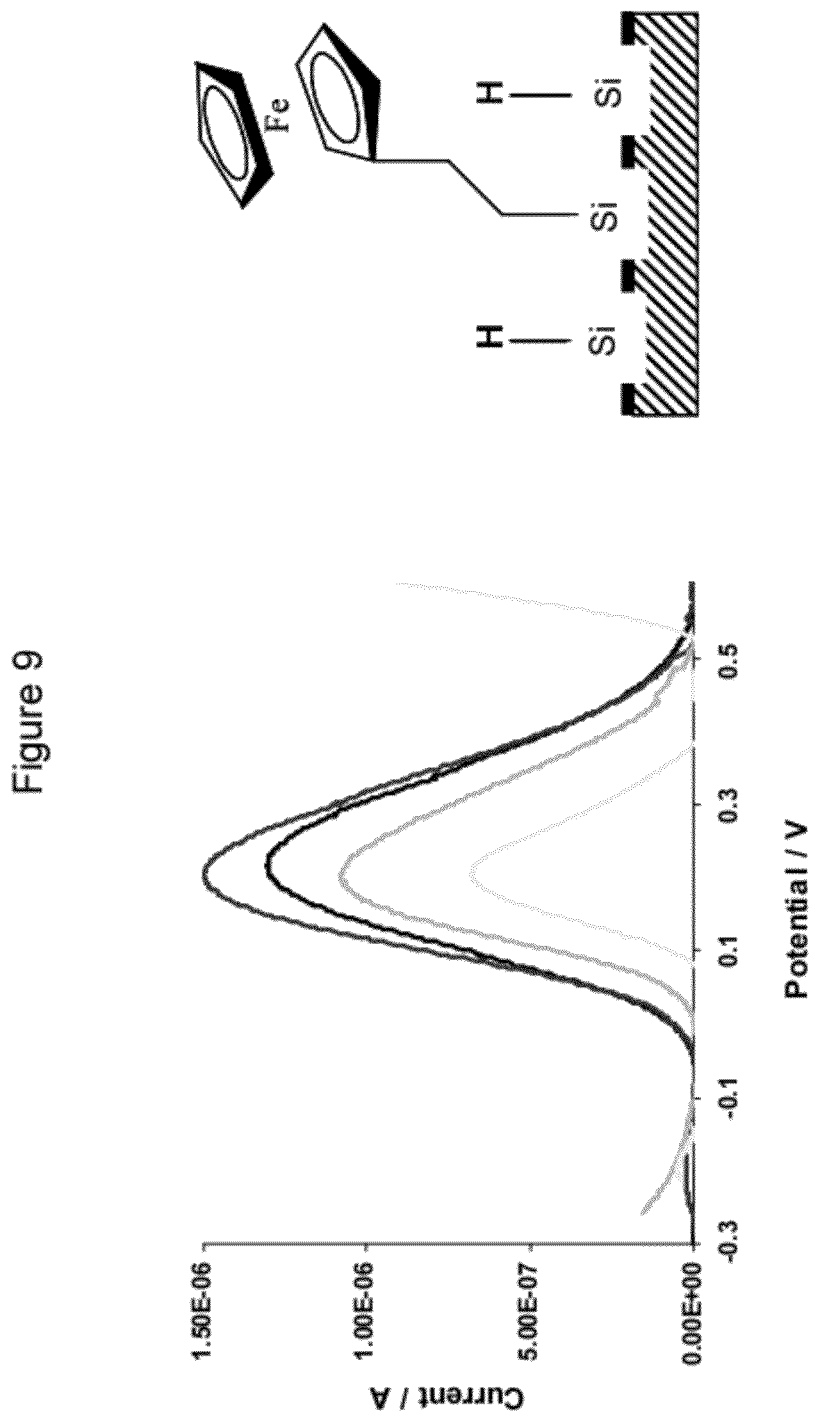
FIG. 9 depicts square wave voltammograms showing the effect of pH on VFc derivatized silicon sample at pH solution of 1.23, 4.61, 7.33 and 9.33, in accordance with an embodiment of the invention.

The amperometric response of the anthracene or ferrocene derivatized silicon substrate at different pH solutions was studied using SWV. SWV was used as the electrochemical probe of the system because it produces a well-defined voltammetric peak in a single sweep. The corresponding square wave voltammograms recorded using a derivatized ferrocene electrode at different pH solutions from pH 1.23 to 9.33 are shown in FIG. 9. These voltammograms show that as the pH values increase, the peak potential of the ferrocene peaks remain at the same peak potential. These results show that ferrocene is a pH insensitive molecule which can act as an internal reference material.

The corresponding SW voltammograms recorded using a derivatized anthracene electrode at different pH solutions, from pH 1.23 to 13.63, are shown in FIG. 10 (a). These voltammograms show that as the pH value increases, the peak potential attributed to the anthracene shifts to a more negative potential. The corresponding plot of the peak potential against different pH is given in FIG. 10(b). The plot reveals a linear response from pH 1 to pH 14 with a corresponding gradient of ca 55.1 mV per pH unit. The ability of anthracene compounds to act as pH sensitive molecule is thus demonstrated.

Figure 11:
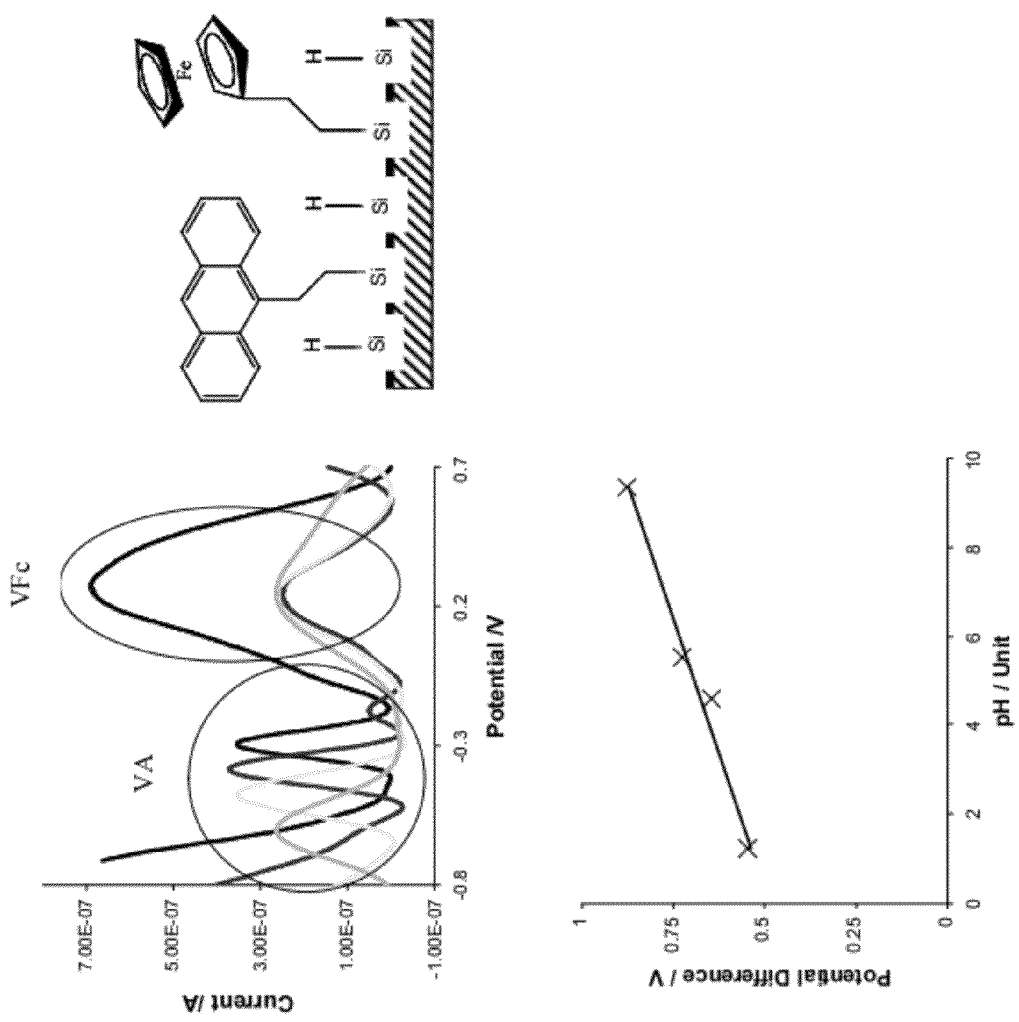
FIG. 11 depicts: (a) square wave voltammograms showing the effect of pH on VA+VFc derivatized silicon sample at pH solutions of 1.23, 4.65, 5.52 and 9.32 (VA circle, peaks going from right to left); and (b) a plot of peak potential difference against pH using the VA+VFc derivatized silicon sample, in accordance with an embodiment of the invention.

The corresponding SW voltammograms recorded using a derivatized ferrocene+anthracene electrode at different pH solutions, from pH 1.23 to 9.33, are shown in FIG. 11 (a). These voltammograms illustrate that as the pH values increase, the ferrocene peak remains at the same peak potential while the anthracene peak shifts to a more negative potential. The corresponding plot of the difference between the two peak potentials versus pH is shown in FIG. 11(b). The plot reveals a linear response from pH 1 to pH 9.33 with a corresponding gradient of ca 45.1 mV per pH unit.

Example 6

Heat Stability

A SW voltammogram was recorded for the silicon wafer derivatized with both VA and FcA moieties at room temperature in pH 6.52 buffer. The derivatized silicon sample was then autoclaved in a Consolidated Stills & Sterilizers for 40 min, and a SW voltammogram was recorded in pH 6.52 buffer after the autoclave. Next, the same sample was autoclaved again under the same condition 10 times, with a SW voltammogram recorded in pH 6.52 buffer after each autoclave.

Figure 12:
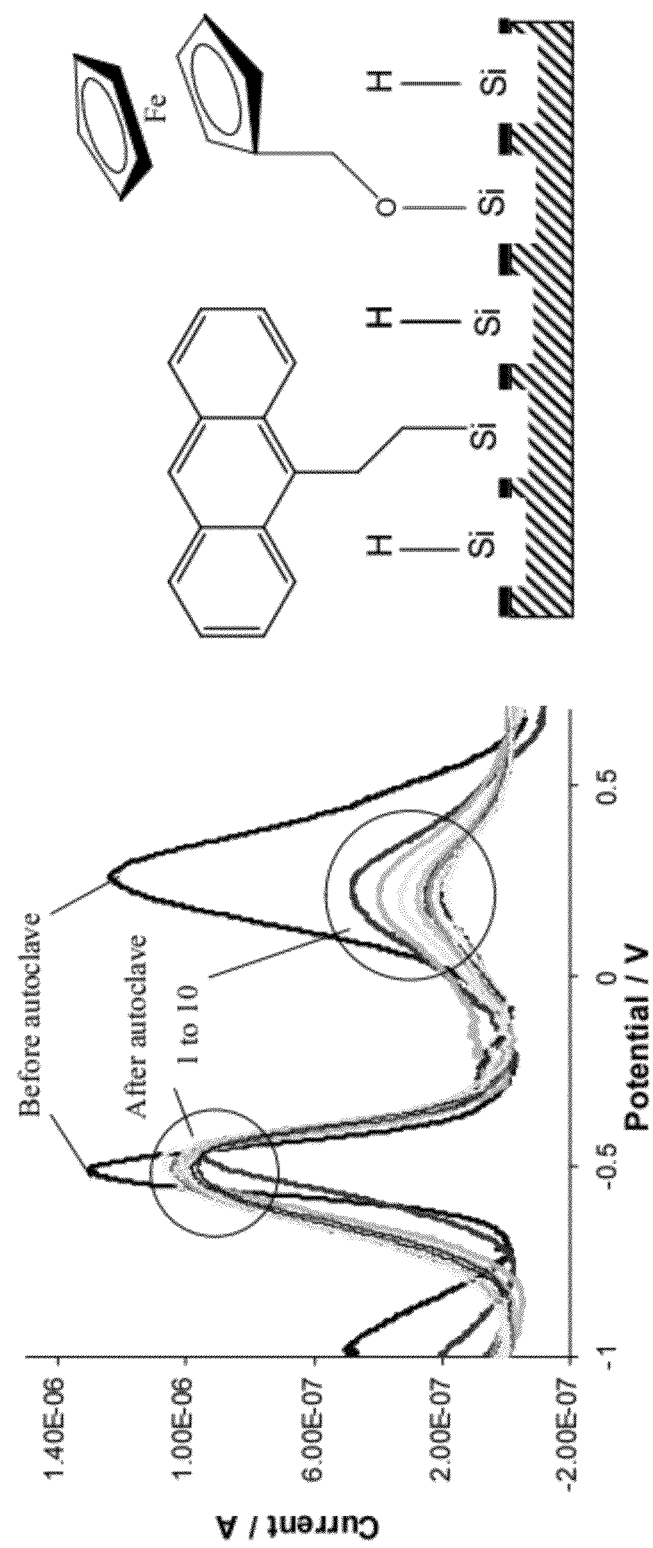
FIG. 12 depicts square wave voltammograms showing the effect of 10 autoclave cycles on FcA+VA derivatized silicon sample, in accordance with an embodiment of the invention. The electrochemical measurements were conducted at pH 6.52 buffer prior to autoclave and after autoclave.

The heat stability testing of the pH sensor was performed using a FcA+VA derivatized silicon sample. The resultant voltammograms are shown in FIG. 12. A decrease in both the ferrocene and anthracene currents were observed after the first autoclave. Thereafter, both the peak currents remain relatively stable though subsequent cycles of autoclaving; in fact the peaks remain stable for ten cycles, showing that the sensor can withstand repeated heat sterilization.

Example 7

Fouling Test

Four SW voltammograms were recorded for the four separate silicon wafers derivatized with FcA and AnA moieties at room temperature in pH 6.52 buffer. These derivatized samples were then autoclaved in the Consolidated Stills & Sterilizers for 20 min and were immersed in a 5 mL cell culture fermentation medium for six days. Then these samples were taken out of the cell culture medium, and SW voltammograms were recorded in pH 6.52 buffer again. SW voltammetry was also carried out in the cell culture medium, using the same silicon wafers.

Figure 13:
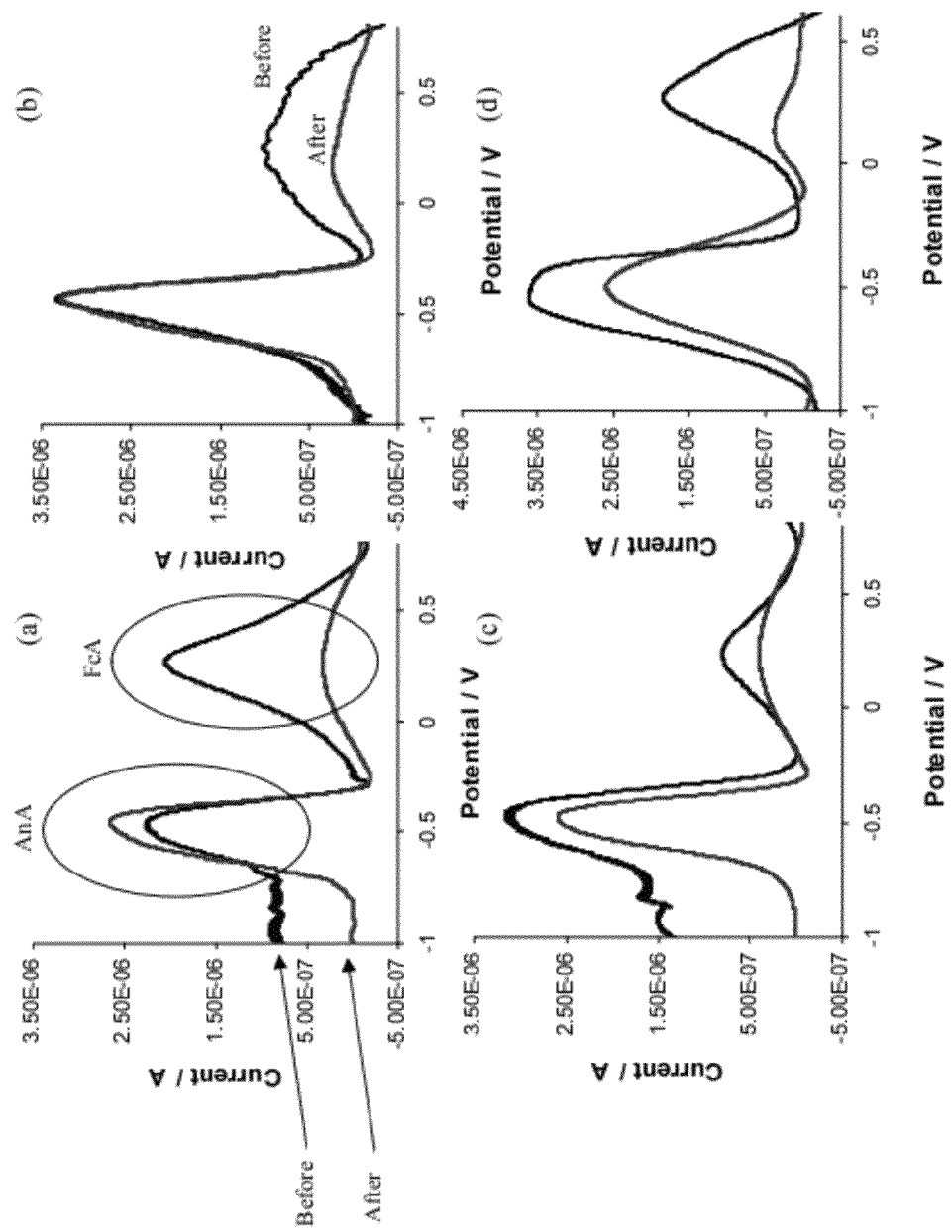
FIG. 13 depicts square wave voltammograms showing minimal fouling on FcA+AnA derivatized silicon samples, in accordance with an embodiment of the invention. The electrochemical measurements were conducted at pH 6.52 buffer before and after six days exposure in the cell culture at four different FcA+AnA derivatized silicon samples (a), (b), (c) and (d)
Figure 14:
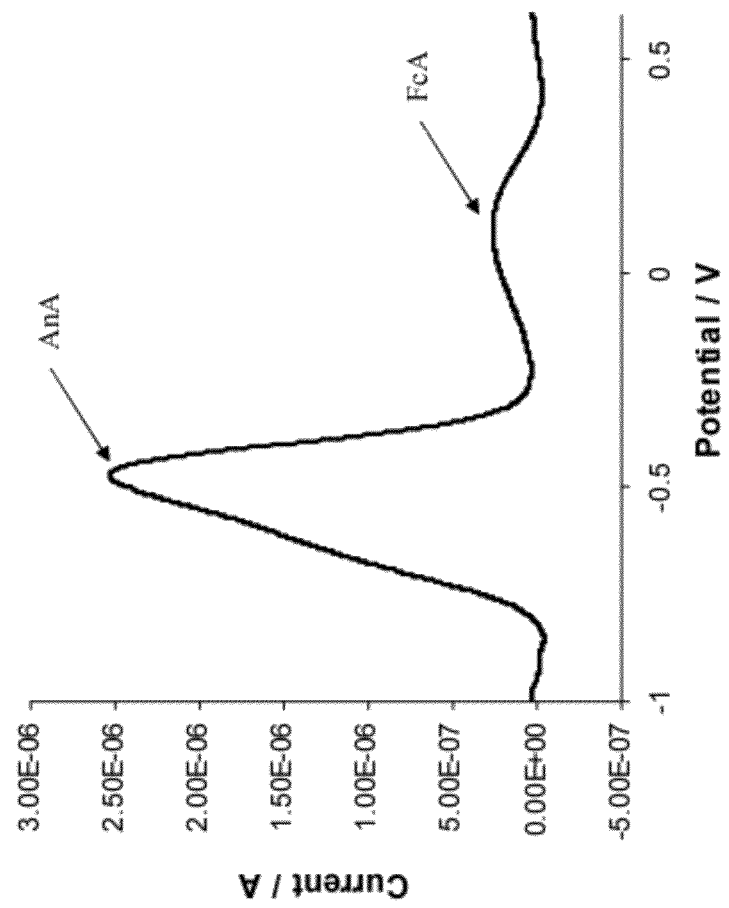
FIG. 14 depicts a square wave voltammogram obtained at FcA+AnA derivatized silicon sample in cell culture medium after sterilization and 6 days exposure, in accordance with an embodiment of the invention.

The fouling testing of the pH sensor was performed using five derivatized silicon samples. The resultant voltammograms were shown in FIG. 13. In all cases, the anthracene peaks remain stable with after six days exposure. The ferrocene peaks decrease after exposure, but the ferrocene peaks are still identifiable. These findings demonstrate that the pH sensors are still in good working order after six days exposure to the cell culture environment, demonstrating that the ability of the derivatized sensor to resist fouling. A control sensor was incubated for 6 days in culture fluid without cells or secreted proteins. This sensor's voltammogram exhibited a similar profile to the four that had been incubated in the actual cell fermentation environment, (FIG. 14) suggesting that any loss of signal amplitude was not a function of cellular debris deposition.

Example 8

Stability of the Anthracene- and Ferrocene-Derivatized Si Surfaces

The stability testing of the Ac+Fc derivatized silicon surface was conducted for 22 days under continuous electrochemical measurement using PGSTAT12 autolab potentiostat in pH 4.65 buffer medium, scanning from −0.8 V to 0.8 V vs. Ag. The Ac peak remained as a well-defined peak with a full width half maximum (FWHM) of ~60 mV throughout the course of the experiments, while the Fc peaks broadened with time. Although the Fc peaks became broader, they are still identifiable and can be used as a reference. These findings demonstrate that the two-component derivatized silicon surface are still in good working order after 22 days continuous operation in pH 4.65 buffer medium, demonstrating the long term stability of the derivatized surface in the buffer medium.

Figure 15:
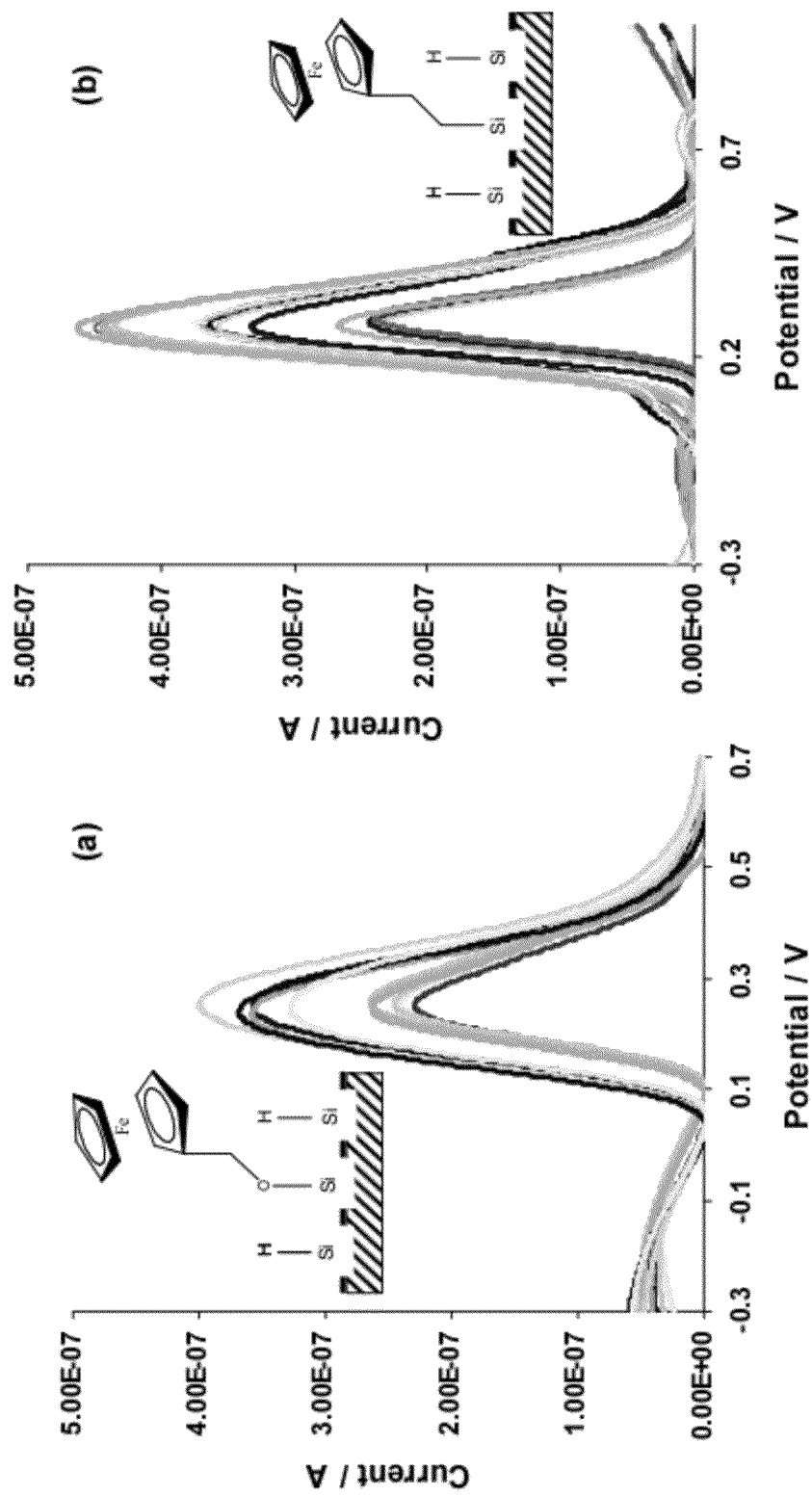
FIG. 15(a) depicts square wave voltammetric responses FcA on Si(100, N-type, 1-5 m$\Omega$ cm) in pH 7.33 buffer medium, showing every $50^{th}$ scan of the 2,500 consecutive runs, in accordance with an embodiment of the invention.
FIG. 15(b) depicts voltammetric responses of VFc on Si(111, N-type, 0.02-0.05 $\Omega$cm in pH 7.33 buffer medium, showing every $50^{th}$ scan of the 2,500 consecutive runs, in accordance with an embodiment of the invention.

In general, the Fc peaks are most well-defined and stable when the Fc molecules were derivatized onto a heavily doped silicon substrate. FIG. 15(a) depicts SW voltammetric responses FcA on Si(100, N-type, 1-5 mΩ cm) in pH 7.33 buffer medium, showing every $50^{th}$ scan of the 2,500 consecutive runs; FIG. 15(b) depicts voltammetric responses of VFc on Si(111, N-type, 0.02-0.05 Ωcm) in pH 7.33 buffer medium, showing every $50^{th}$ scan of the 2,500 consecutive runs. In some cases, both VFc and FcA moieties behave better on an N-type substrate than a P-type substrate in terms of the size of the peak current produced. The Fc derivatized silicon surfaces were all pH insensitive, i.e., the Fc peak does not shift upon exposure to different pH environments.

Example 9

Temperature Variation

The Nernst equation provides a theoretical framework for evaluating the temperature dependence of redox active species. It predicts that the slope of the peak potential against pH plot will increase as the temperature increases:

$$E_p = E_f^0 - \frac{2.3RTm}{nF}\text{pH} \qquad \text{Eq. 1}$$

Where $E_p$ is the peak potential (V), $E_f^o$ is the standard electrode potential (V), R is the universal gas constant (J K$^{-1}$ mol$^{-1}$), T is the absolute temperature (K), F is the Faraday constant (C mol$^{-1}$), m and n are the number of protons and electrons involved in the redox reaction, respectively. In the case of anthracene, the redox process for such molecules in the aqueous solution involves the participation of 2 electrons and 2 protons, thus m=n=2.

Figure 16:
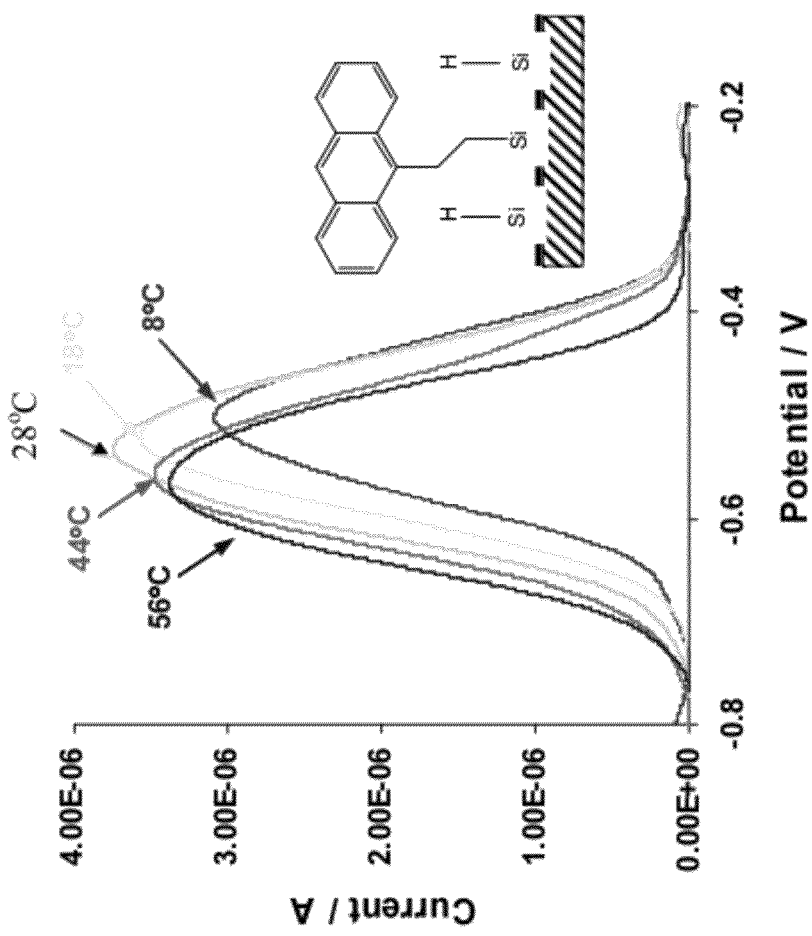
FIG. 16 depicts the square wave voltammetric response of Ac derivatized silicon surface at various temperatures (8, 17, 28 44, 56° C.) in pH 7.33 buffer medium, in accordance with an embodiment of the invention.

SW voltammograms were recorded for three pH solutions at pH 4.65, 7.33 and 9.35. FIG. 16 shows the overlaid SW voltammograms of Ac derivatized silicon over the temperature range of 8 to 56° C. in pH 7.33 buffer medium. Similar responses were obtained at pH 4.65 and pH 9.35. There is a shift of the peak potential to more negative values with increasing temperature which may be attributed in part to a combination of changes in the reference couple, the temperature dependence of the formal potential ($E_f^0$), and the temperature term in Eq. 1. Analysis of the slope of the peak potential as a function of pH obtained experimentally at each temperature is tabulated in Table 1, which illustrates that the slope of pH against peak potential plot varies with temperature. The theoretical slope as predicted by the Nernst equation as seen in Eq. 1 is also listed in Table 1 for comparison. As can be seen, the variation of the gradient of peak potential with pH is not Nernstian and indeed is relatively insensitive of temperature varying by about 2 mV/pH unit over a temperature range of ~50° C. This dependence can be compared to a 10 mV/pH shift that can be observed for a glass electrode. This small shift with temperature is beneficial in that it not only demonstrates that these Ac derivatized silicon wafers may be used as pH sensors at elevated temperatures, but also that they are not greatly affected by changes in temperature.

TABLE 1

A comparison of the theoretically predicted slope and experimentally obtained slope of the plot of pH against Ac peak potential for a range of temperatures.

| T (° C.) | 8 | 17 | 28 | 44 | 56 |
|---|---|---|---|---|---|
| T (K) | 281 | 290 | 301 | 317 | 329 |
| Theoretical (mV/pH) | 55.7 | 57.5 | 59.7 | 62.8 | 65.2 |
| Experimental (mV/pH) | 55.0 | 55.5 | 56 | 56.3 | 57.0 |

Example 10

Stability During Active Measurement in Cell Culture Medium

A fouling testing was carried out using anthracene derivatized silicon (100) wafer in the incubator (under controlled temperature of 37° C. and $CO_2$ content of 5%) with continuous electrochemical measurements in cell culture (LP VA) medium for 7 days using a three-electrode setup connected to an µautolab type III potentiostat. The three-electrode setup (in an electrochemical cell) was autoclaved in a Consolidated Stills & Sterilizers autoclave for 40 min prior to adding 5 mL of the cell culture medium to the autoclaved setup. The electrochemical cell containing the medium was then transferred to the incubator, where continuous electrochemical measurements were performed.

Figure 18:
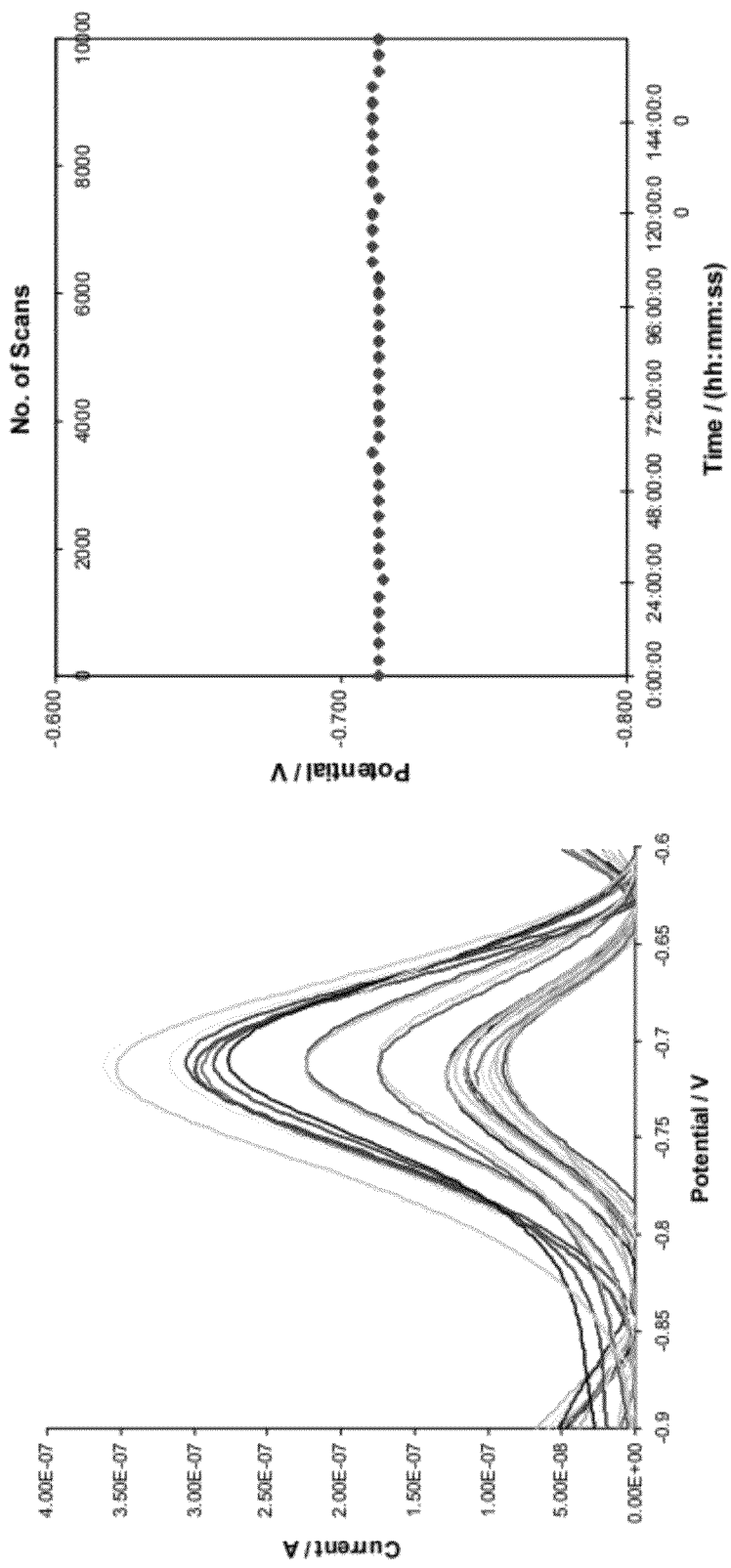
FIG. 18(a) depicts voltammograms taken on an anthracene derivatized silicon sensor over the 7 day period in cell culture medium (every $250^{th}$ scan of the 10,000 consecutive runs), in accordance with an embodiment of the invention.
FIG. 18(b) depicts a plot of the anthracene peak potential over the 7 day time period, in accordance with an embodiment of the invention.

Voltammograms were taken repeatedly over 7 days resulting in 10,000 consecutive voltammograms. FIG. 18(a) shows voltammograms taken over the 7 day period (every $250^{th}$ scan of the 10,000 consecutive runs). The anthracene peak was observed at ~−0.71V vs. Ag and remained consistent throughout the 7 days of in-situ electrochemical measurements in the cell culture medium. A plot of the anthracene peak potential over the 7 day time period is shown in FIG. 18(b). These findings demonstrate that the anthracene derivatized silicon is still in good working order and that the peak potential remains consistent while the sensor is actively sensing the solution for 7 days.

Example 11

Derivatization of H-Terminated Silicon Surfaces with 2-allyl-1-Hydroxy-Anthraquinone Into a round bottom flask containing 50 mL of mesitylene was placed 5 mg of 2-allyl-1-hydroxy-anthraquinone. Nitrogen was bubbled for at least 30 minutes. Subsequently, a H-terminated silicon wafer was placed into the flask and was allowed to react with 2-allyl-1-hydroxy-anthraquinone for 12 hours under reflux at 150° C. in an oil bath. During the reaction, the solution was purged with nitrogen gas to prevent the substrate from being re-oxidized. Following the reaction, the 2-allyl-1-hydroxy-anthraquinone derivatized silicon wafer was rinsed with dichloromethane, hexane, then methanol and dried under a stream of nitrogen.

Example 12

Derivatization of Silicon Wafers with Ferrocene Using a Semiconductor Oxide Surface Si(100) wafer pieces were cleaned using "Piranha" solution (3:1 v/v concentrated $H_2SO_4$/30% $H_2O_2$) for 30 minutes at 100° C. and rinsed thoroughly with deionized water. Subsequently, the wafers were oxidized in 2:1:8 HCl/$H_2O_2$/$H_2O$ for 15 minutes at 80° C. followed by 2:1:8 $NH_4OH$/$H_2O_2$/$H_2O$ for 15 minutes at 80° C. and then rinsed with copious amounts of water. The oxidized silicon wafers were then immersed in 2% 3-aminopropyltriethoxysilane (APTES) solution in acetone for 2 minutes followed by rinsing with acetone to form an amino-terminated monolayer. This was then allowed to react with 10 mg/Int, dicyclohexyl-carbodiimide (DCC) and 50 mg/mL ferrocene carboxylic acid in DMSO for 12 hours. Following the reaction, the ferrocene derivatized silicon wafer was rinsed with dichloromethane, acetone, and methanol and then dried under a stream of nitrogen.

Example 13

Derivatization of Silicon Wafers with Anthracene Using a Semiconductor Oxide Surface Si(100) wafer pieces were cleaned using "Piranha" solution (3:1 v/v concentrated $H_2SO_4$/30% $H_2O_2$) for 30 minutes at 100° C. and rinsed thoroughly with deionized water. Subsequently, the wafers were oxidized in 2:1:8 HCl/$H_2O_2$/$H_2O$ for 15 minutes at 80° C. followed by 2:1:8 $NH_4OH$/$H_2O_2$/$H_2O$ for 15 minutes at 80° C. and then rinsed with copious amounts of water. The oxidized silicon wafers were then immersed in 2% 3-APTES solution in acetone for 2 minutes followed by rinsing with acetone to form an amino-terminated monolayer. This was then allowed to react with 10 mg/mL dicyclohexyl-carbodiimide (DCC) and 50 mg/mL anthracene carboxylic acid in DMSO for 12 hours. Following the reaction, the anthracene derivatized silicon wafer was rinsed with dichloromethane, acetone and methanol and then dried under a stream of nitrogen.

Example 14

Ferrocene Covalently Attached to Various Doped Si(100) Substrates

Figure 19:
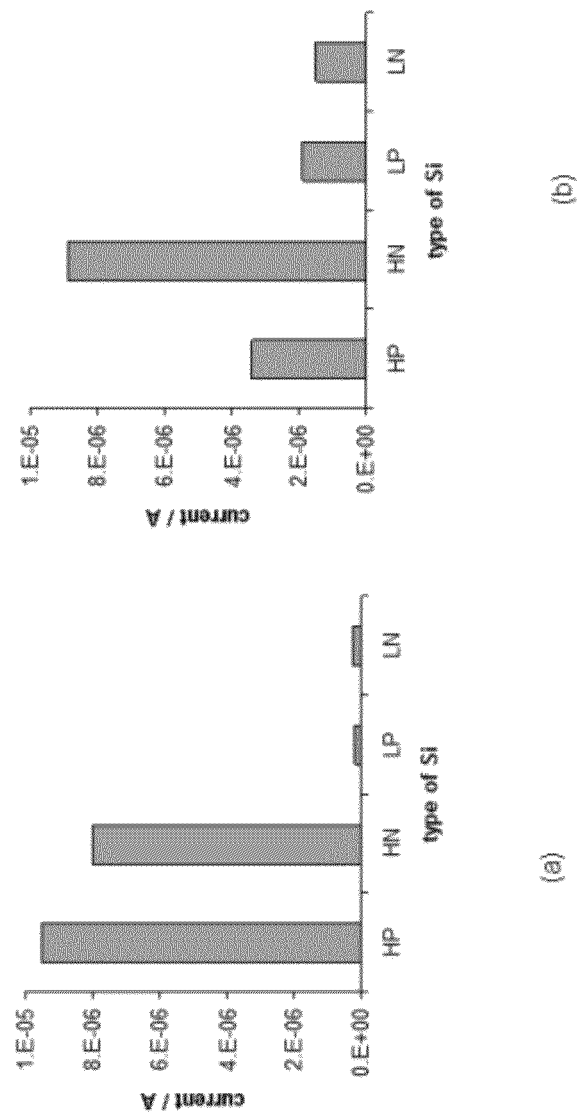
FIG. 19 has charts showing the peak current of silicon substrates derivatized with (a) vinyl ferrocene and (b) ferrocene carboxaldehyde in pH 1.63 solution for four types of doped silicon, in accordance with an embodiment of the invention.

Ferrocene was covalently attached to the following four silicon surfaces via an H-terminated silicon substrate and vinyl ferrocene: i) Si (100) N-type (0.02-0.05 ohm-cm)—highly-doped N-type, ii) Si (100) P-type (0.005-0.020 ohm-cm)—highly-doped P-type, iii) Si (100) N-type (10-40 ohm-cm)—lightly-doped N-type, and iv) Si (100) P-type (10-90 ohm-cm)—highly-doped P-type. A well-defined ferrocene peak was observed for all four substrates. The highly-doped substrates in general produced a larger electrochemical current than the corresponding lightly-doped substrates. While not being bound by theory, this difference may be explained by the fact that the highly-doped substrates contain more charge carriers, i.e., are more conductive. Similar observations were observed when the electrochemistry was performed in a solution of ferrocene carboxaldehyde. FIG. 19 has charts showing the peak current of silicon substrates derivatized with (a) vinyl ferrocene and (b) ferrocene carboxaldehyde in pH 1.63 solution on the four types of doped silicon.

Example 15

Four Electrode System

Figure 20:
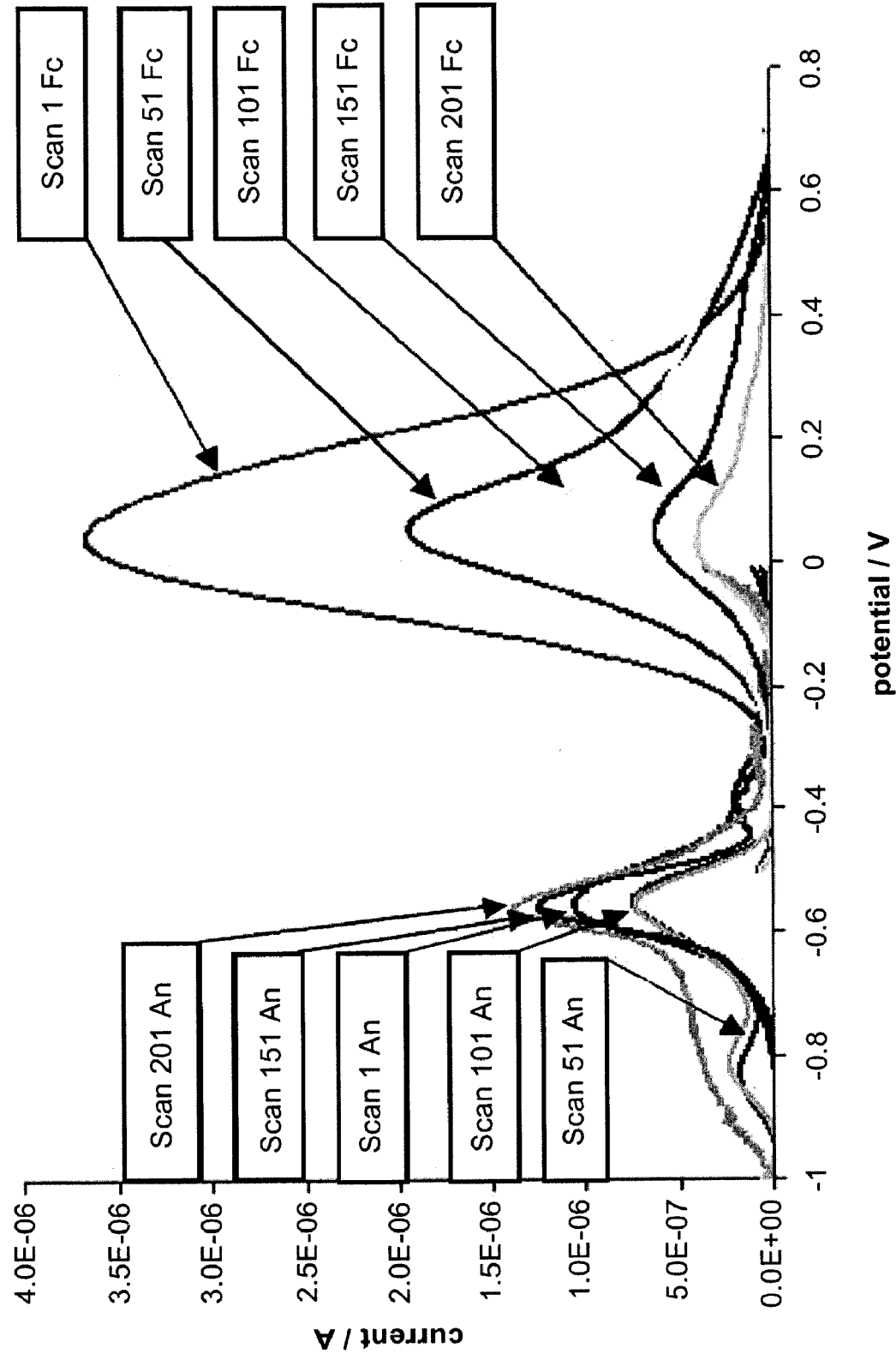
FIG. 20 depicts square wave voltammograms obtained with a four electrode system having highly-doped N-type silicon derivatized with vinyl ferrocene and at a lightly-doped p-type silicon derivatized with anthracene carboxaldehyde, in accordance with an embodiment of the invention.

A system was constructed having four electrodes comprising (i) a counter electrode, (ii) a reference electrode, (iii) a highly-doped N-type silicon wafer derivatized with vinyl ferrocene, and (iv) a lightly-doped P-type silicon wafer derivatized with anthracene carboxaldehyde. FIG. 20 illustrates the voltammograms obtained with the four electrode system consisting of a highly-doped N-type silicon wafer derivatized with vinyl ferrocene and a lightly-doped P-type silicon wafer derivatized with anthracene carboxaldehyde. The voltammograms were obtained in pH 7.03 solution and the peak potentials were stable over 200 consecutive scans (every 50th scan is shown).

Example 16

Working Electrodes Coated with Nafion Membranes

A Nafion membrane was applied to a working electrode having ferrocene. A 5 mil thick section of pre-formed Nafion membrane (N115) was pre-treated either by soaking in water or in an acid solution (about 5% HCl or 5M $HNO_3$) at about 100° C. for about 1 hr. The treated membrane was then cut to a size appropriate to cover the surface of the working electrode. The Nafion membrane was then coated with a liquid dispersion of Nafion 117 or Nafion 2020, and applied directly to the electrode surface. The membrane-coated electrode was then cured in a regular or vacuum oven at about 120° C. for about 1 hr. The electrode was then rehydrated and tested. Testing showed stability as to the peak position in SWV.

Example 17

Nafion-Plastic Composites

A porous plastic membrane (pore size 75-100 micron, 0.5 mm thick) is cut into a 1 cm disk. The disk is saturated with a Nafion dispersion and allowed to dry for 30 min at 50° C. After a second cycle of saturation and drying, the disk is placed in a 120° C. oven for about 1 hour. A single electrode is then wetted with the Nafion dispersion and placed on the smooth side of the disk. This assembly is then cured at 120° C. for about 1 hour. The backside of the electrode is then coated with a conductive epoxy and a wire is affixed. The assembly is potted into a waterproof fixture for electrochemical measurements.

Example 18

Light Sensitivity

Figure 30:
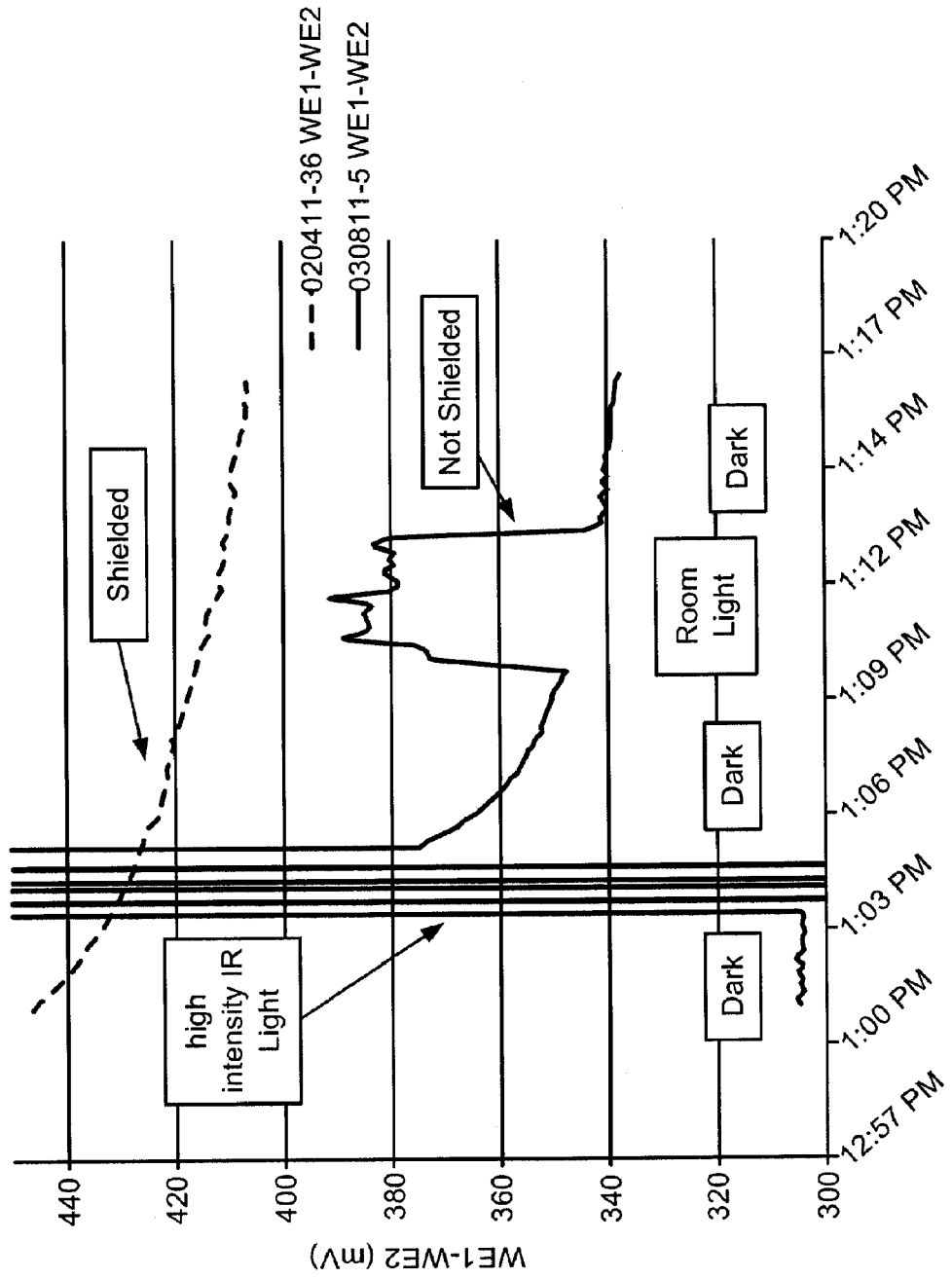
FIG. 30 shows sensor output (y-axis, mV) with time (x-axis) during pH measurements for a shielded (top) and unshielded (bottom) sensors.

A sensor has a first working electrode (WE1) and second working electrode (WE2) that are formed of silicon. WE1 includes a layer of ferrocene and WE2 includes a layer of anthracene. A first probe has WE1 and WE2 that are shielded from light with PES layers, and a second probe has WE1 and WE2 that are not shielded (or unshielded) from light. The first probe and second probe are inserted into a solution having a pH of about 4. Continuous pH measurements are made and plotted as the difference between the peak potentials of WE1 and WE2. Sensor outputs (y-axis, mV) as a function of time (x-axis) during pH measurements for both the shielded (dashed line, top) and unshielded (solid line, bottom) probes are shown in FIG. 30. The output of the shielded sensor upon exposure to light is different than the output of the unshielded sensor upon exposure to light. During pH measurements, the output of the unshielded sensor shows a sensor response that is coincident with exposure to light; the output of the shielded sensor does not exhibit such a behavior. Sensor output when the first and second working electrodes are shielded (top) does not display the light-sensitive behavior of the unshielded working electrodes (bottom). The figure also shows the effect of either infrared (IR) or room light for both shielded and unshielded probes. The shielded sensor is unresponsive to IR or room light.

Example 19

The Effect of Light on Sensor Output

Figure 31A:
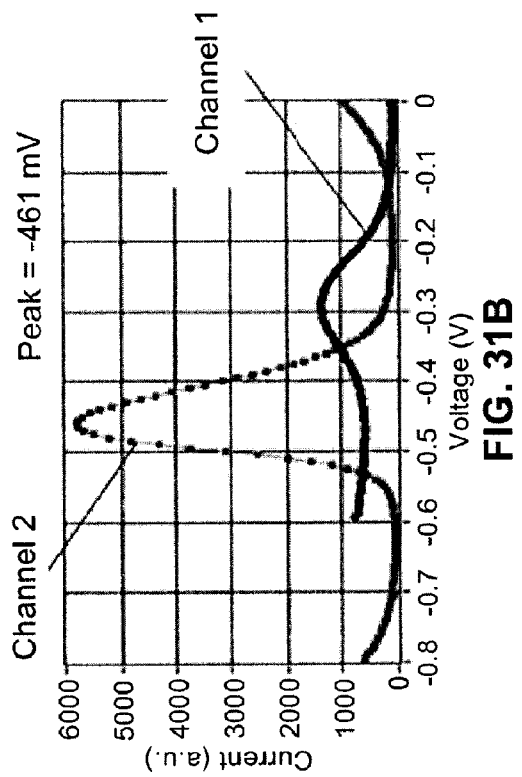
FIGS. 31A-31F show sensor output (y-axis; current, arbitrary units) at various pH's and under light and dark conditions as a function of voltage (mV)
Figure 31B:
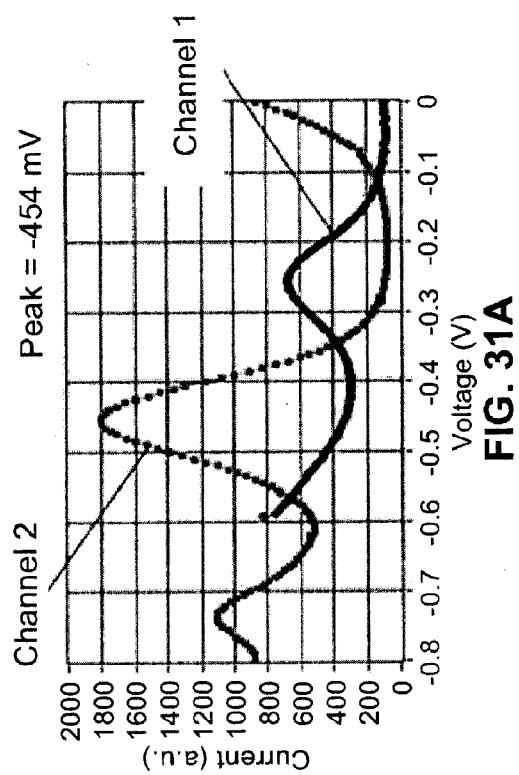
Figure 31C:
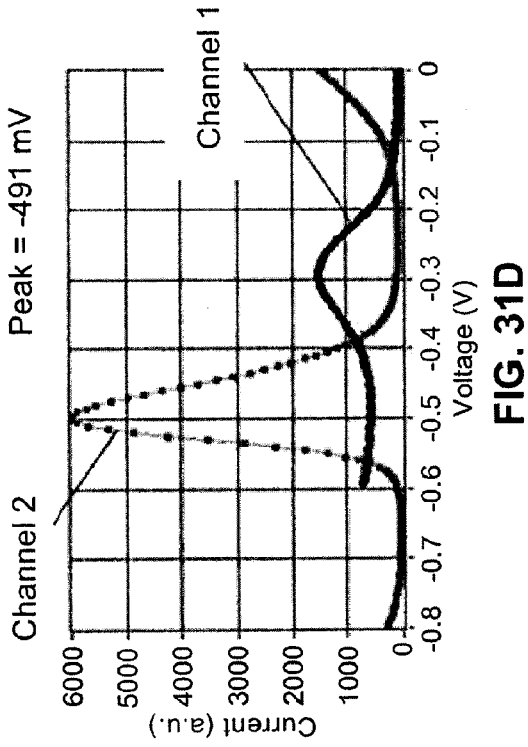
Figure 31D:
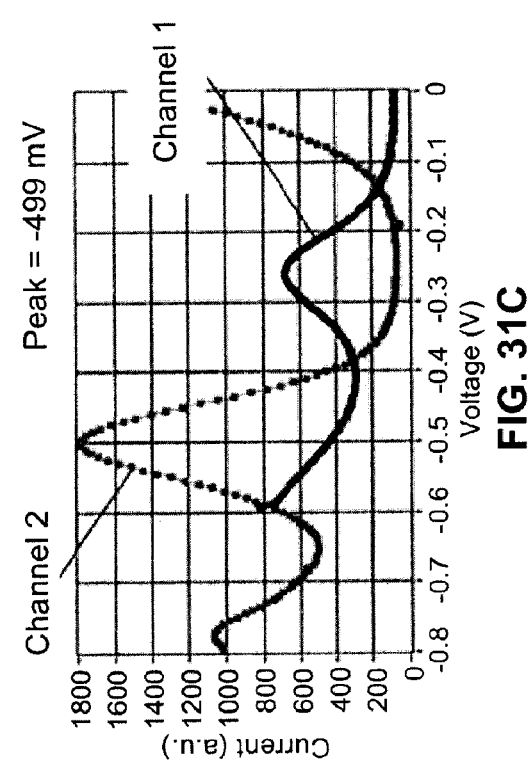
Figure 31E:
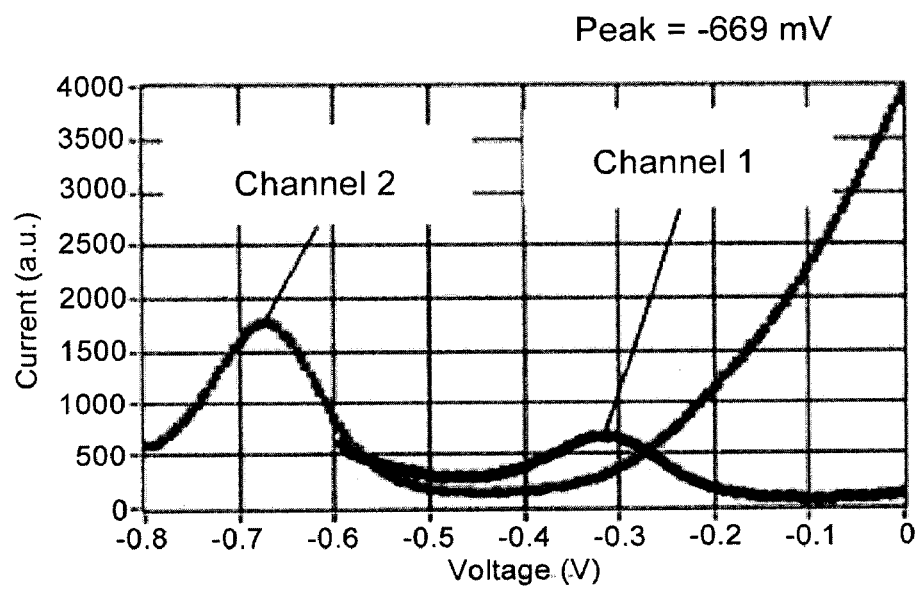
Figure 31F:
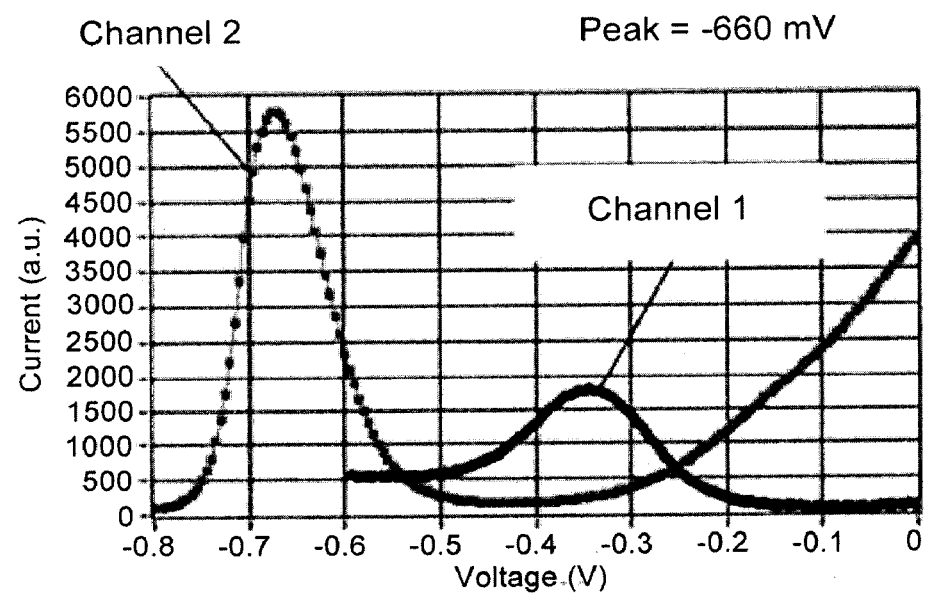

A sensor has a first working electrode (WE1) and second working electrode (WE2) that are formed of silicon. WE1 includes a layer of ferrocene and WE2 includes a layer of anthracene. The sensor is immersed in various solutions, each solution having a predetermined pH. Sensor output is recorded both with and without exposure of the sensor to light. FIGS. 31A-31F show sensor output (y-axis; current, arbitrary units) at various pH's and under light and dark conditions as a function of voltage (mV). Channel 2 corresponds to the sensor output for WE2. Also provided in the figures are Channel 2 peak positions (mV). FIG. 31A shows the sensor output at pH 5 without exposure to light (i.e., the sensor is in the dark). FIG. 31B shows the sensor output at pH 5 while the sensor is exposed to light. FIG. 31C shows the sensor output at pH 7 without exposure to light. FIG. 31D shows the sensor output at pH 7 while the sensor is exposed to light. FIG. 31E shows the sensor output at pH 10 without exposure to light. FIG. 31F shows the sensor output at pH 10 while the sensor is exposed to light. The Channel 2 signal (current) when the sensor is exposed to light is more intense than situations in which pH measurements are made without exposure to light. This indicates that, when the sensor is exposed to light, better signal to noise may be achieved.

Example 20

The Effect of Light on Sensor Output

A sensor has a first working electrode (WE1) and second working electrode (WE2) that are formed of silicon. WE1 includes a layer of ferrocene and WE2 includes a layer of anthracene. The sensor is immersed in a solution with a pH of 5. Sensor output is recorded both with and without exposure of the sensor (and WE1 and WE2) to light of fixed intensities and wavelengths. Light is exposed on sensor surfaces having the ferrocene and anthracene moieties. It is observed that peak shapes are sharper in the presence of light up to a certain intensity and wavelength. At higher intensities the signal is destroyed. Optimal responses are obtained in the IR or near-IR wavelength range, such as light having a wavelength greater than or equal to about 750 nm, or greater than or equal to about 850 nm.

Example 21

Doping Configurations

Multiple sensors are formed from silicon wafers having varying doping configurations. Each sensor has a first working electrode (WE1) and second working electrode (WE2) that are formed of silicon. WE1 includes a layer of ferrocene and WE2 includes a layer of anthracene. During pH measurements, electrochemical responses from anthracene-covered electrodes (WE2) are observed when anthracene is derivatized onto the following silicon surfaces: Si(100) wafer, p-type, resistivity between about 1 and 20 Ω-cm; Si(100) wafer, p-type, resistivity between about 1 and 90 Ω-cm; Si(111) wafer, p-type, resistivity between about 1 and 20

Ω-cm; and Si(111) wafer, p-type, resistivity between about 1 and 10 Ω-cm. An anthracene signal with an appreciable signal-to-noise ratio is not observed when derivatized on an n-type silicon substrate. An anthracene signal is not observed when derivatized on a p-type silicon substrate with resistivity less than about 1 Ω-cm. Electrochemical responses are observed for ferrocene on both p-type and n-type silicon (both Si(100) and Si(111)). Signals for Ferrocene on all resistivities of p-type silicon and on n-type silicon with resistivities<5 μΩ-cm are unstable over time (in some situations, it is observed that the signal degrades with continuous square wave voltammetric scanning). Ferrocene on n-type surfaces with resistivities between 1 and 90 Ω-cm are stable.

Example 22

Sensor Stability

Figure 33:
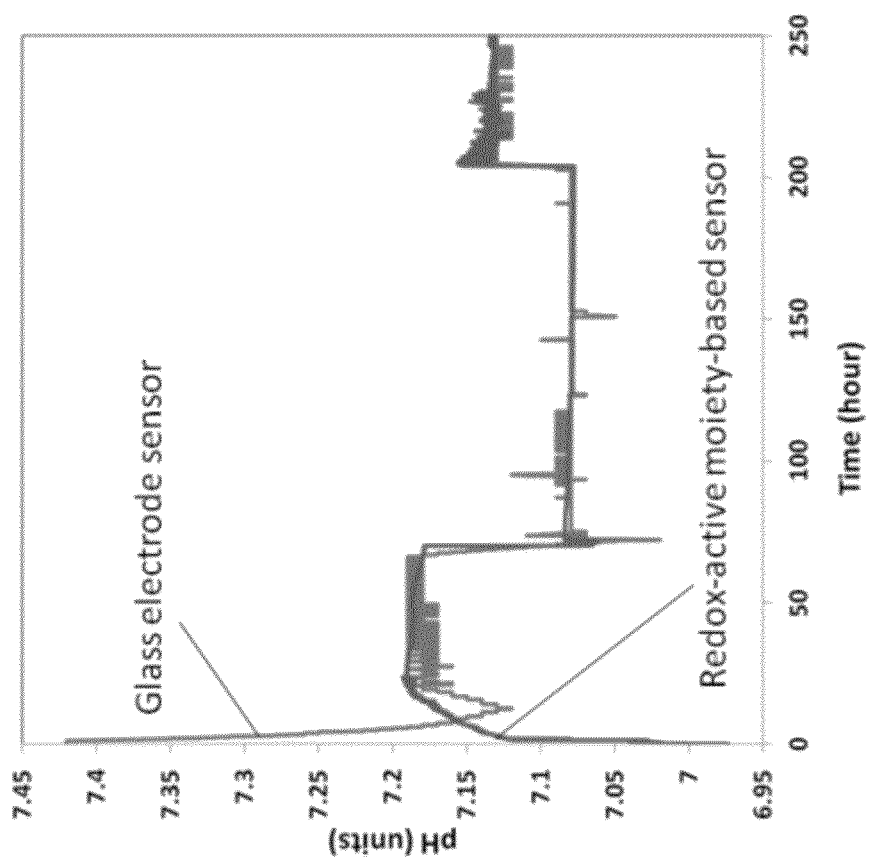
FIG. 33 shows the pH of a fermentation reactor as a function of time as measured by a glass electrode sensor and a redox-active moiety-based pH sensor.

A test was conducted to monitor fermentation in a fermentation reactor. The pH of the reactant (i.e., cell culture) and product content of the fermentation reactor was monitored over a 10-day period using both a redox-active moiety-based pH sensor (see above) and a conventional glass electrode sensor (Applikon Biotechnology). Both sensors were autoclaved within the bioreactor prior to the initiation of the cell culture. The redox-active moiety-based pH sensor was not recalibrated during the 10-day period. FIG. 33 shows the pH of the contents of the fermentation reactor over the 10-day period. The redox-active moiety-based pH sensor tracked the glass electrode sensor without any appreciable drift and without exhibiting any appreciable electronic background noise throughout the course of the 10-day period. In contrast, the glass electrode sensor exhibited electronic noise during the 10-day period.

Electrochemical sensor systems, devices and methods provided herein can be combined with or modified by other systems, devices and methods. For example, electrochemical sensors described herein, including methods for forming such sensors, can be combined with or modified by systems and methods described in U.S. patent application Ser. No. 12/049, 230 to Kahn et al. ("SILICON ELECTROCHEMICAL SENSORS") and PCT/US2008/066165 to Kahn et al. ("SEMICONDUCTOR ELECTROCHEMICAL SENSORS"), which applications are entirely incorporated herein by reference.

In some embodiments, sensors have been described as being used to detect the presence or absence of an analyte (e.g., H+). It will be appreciated, however, that detecting the presence or absence of an analyte can include detecting (or measuring) the concentration of an analyte. For example, detecting the presence or absence of H+ in a liquid sample using any of the sensors described herein can include detecting (or measuring) the concentration of H+.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A sensor for detecting the presence or absence of an analyte, comprising:
   a first solid state electrode having a surface having immobilized thereon a layer of a first redox-active moiety, wherein the first redox-active moiety has an oxidation potential and/or a reduction potential that is sensitive to the presence of the analyte; and
   a second solid state electrode having a surface having immobilized thereon a layer of a second redox-active moiety and a layer of a polymeric material adjacent to the layer of the second redox-active moiety, wherein the second redox-active moiety has an oxidation potential and/or reduction potential that is sensitive to the presence of the analyte.

2. The sensor of claim 1, wherein the layer of the polymeric material is a light blocking layer.

3. The sensor of claim 2, wherein the polymeric material comprises polyethersulphone.

4. The sensor of claim 1, further comprising a protective layer adjacent to the layer of the polymeric material.

5. The sensor of claim 4, wherein the protective layer comprises another polymeric material.

6. The sensor of claim 1, wherein the polymeric material has the formula $C_7HF_{13}O_5S*C_2F_4$.

7. The sensor of claim 1, wherein the layer of the polymeric material comprises a porous plastic.

8. The sensor of claim 1, wherein the first or second solid state electrode comprises carbon.

9. The sensor of claim 1, wherein the first or second solid state electrode comprises silicon.

10. The sensor of claim 1, wherein the layer of the polymeric material comprises pores.

11. The sensor of claim 10, wherein said pores have a pore size between about 0.1 micrometers and 1 micrometer.

12. The sensor of claim 1, wherein the analyte is hydrogen ion.

13. The sensor of claim 1, wherein the layer of the polymeric material is an ion selective layer.

14. A solid state sensor for detecting the presence or absence of an analyte, comprising (i) a solid state electrode having a surface having immobilized thereon a layer of a redox-active moiety, (ii) a layer of a polymeric material and (iii) a protective layer adjacent to the layer of the polymeric material, wherein the layer of the polymeric material is porous and covers the layer of the redox-active moiety, wherein the redox-active moiety has an oxidation potential and/or a reduction potential that is directly sensitive to the presence of the analyte, and wherein the redox-active moiety is immobilized on the surface through a covalent interaction with the solid state electrode.

15. The solid state sensor of claim 14, further comprising a light blocking layer adjacent to the layer of the polymeric material.

16. The solid state sensor of claim 15, wherein the light blocking layer transmits less than 10% of light incident on the light blocking layer.

17. The solid state sensor of claim 16, wherein the light blocking layer transmits less than 5% of light incident on the light blocking layer.

18. The solid state sensor of claim 17, wherein the light blocking layer transmits less than 1% of light incident on the light blocking layer.

19. The solid state sensor of claim 14, wherein the analyte is hydrogen ion.

20. The solid state sensor of claim 14, wherein the solid state electrode comprises silicon.

21. The solid state sensor of claim 14, wherein the layer of the polymeric material is an ion selective layer.

22. The solid state sensor of claim 1, wherein the solid state electrode is non-metallic.

23. The solid state sensor of claim 14, wherein the layer of the polymeric material selectively screens off anions and only allows the passage of cations.

* * * * *